US007064106B2

(12) United States Patent
Tojo et al.

(10) Patent No.: US 7,064,106 B2
(45) Date of Patent: *Jun. 20, 2006

(54) GENE AND USE THEREOF

(75) Inventors: Hideaki Tojo, Ibaraki (JP); Nozomi Katayama, Ibaraki (JP); Shigeya Kakimoto, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 351 days.

This patent is subject to a terminal disclaimer.

(21) Appl. No.: 10/168,067

(22) PCT Filed: Dec. 19, 2000

(86) PCT No.: PCT/JP00/08985

§ 371 (c)(1),
(2), (4) Date: Jun. 14, 2002

(87) PCT Pub. No.: WO01/46413

PCT Pub. Date: Jun. 28, 2001

(65) Prior Publication Data

US 2004/0072742 A1    Apr. 15, 2004

(30) Foreign Application Priority Data

Dec. 20, 1999 (JP) ............... 11-361679
Dec. 22, 1999 (JP) ............... 11-365176

(51) Int. Cl.
A61K 38/00    (2006.01)
C07K 1/00     (2006.01)
C07K 14/705   (2006.01)
C07K 16/28    (2006.01)
G01N 33/567   (2006.01)

(52) U.S. Cl. ............... 514/12; 530/350; 530/388.22; 536/23.5; 435/7.2; 435/69.1

(58) Field of Classification Search ............... 514/12; 530/350, 388.2; 536/23.5; 435/7.2, 69.1
See application file for complete search history.

(56) References Cited

FOREIGN PATENT DOCUMENTS

WO    WO 99/59560    11/1999
WO    WO 00/12544    3/2000

OTHER PUBLICATIONS

Westendorf, et al., "Identification and characterization of a protein containing formin homology (FH1/FH2) domains", Gene 232 (1999), 173-182.

(Continued)

Primary Examiner—Karen Cochrane Carlson
Assistant Examiner—Marsha Tsay
(74) Attorney, Agent, or Firm—Edwards Angell Palmer & Dodge LLP; David G. Conlin, Esq.; Gregory B. Butler, Esq.

(57) ABSTRACT

A protein and DNA encoding the same are useful as preventives/remedies for diseases such as hypoglycemia, etc. The protein of the present invention is also useful as a reagent for screening a compound that inhibits the binding of the protein of the present invention to IRAP (insulin responsive aminopeptidase) or to GLUT4 (glucose transporter 4). The compound that inhibits the binding of the protein of the present invention to IRAP or GLUT4 is useful as a preventive/remedy for diseases, e.g., hyperglycemia, diabetes mellitus, etc.

5 Claims, 22 Drawing Sheets

OTHER PUBLICATIONS

Wu-Wong, et al., "Endothelin Stimulates Glucose Uptake and GLUT4 Translocation via Activation of Endothelin $ET_A$ Receptor in 3T3-L1 Adipocytes*", The Journal of Biological Chemistry, vol. 274, No. 12, Mar. 19, 1999, pp. 8103-8110.

Thurmond, et al., "Regulation of Insulin-stimulated GLUT4 Translocation by Munc18c in 3T3L1 Adipocytes*", The Journal of Biological Chemistry, vol. 273, No. 50, Dec. 11, 1998, pp. 33876-33883.

Waters, et al., "The Amino Terminus of Insulin-responsive Aminopeptidase Causes Glut4 Translocation in 3T3-L1 Adipocytes*", The Journal of Biological Chemistry, vol. 272, No. 37, Sep. 12, 1997, pp. 23323-23327.

EPO Communication dated May 27, 2004.

Ross, Stuart A., "Increased Intracellular Sequestration of the Insulin-regulated Aminopeptides Upon Differentiation of 3T3-L1 Cells," *Biochemical Journal*, vol. 330, No. 2, pp. 1003-1008, XP-0021252805, 1998.

Fig. 1

```
         10        20        30        40        50        60        70        80        90
TGAGCCGGCCGCAGAGCCATGGCGGGCGGGGAAGACCGCGGGGACGGAGAGCCGGTATCAGTGGTGACCGTGAGGGTGCAGTACCTGGAA
                  MetAlaGlyGlyGluAspArgGlyAspGlyGluProValSerValValThrValArgValGlnTyrLeuGlu 100       110       120       130       140       150       160       170       180
GACACCGACCCCTTCGCATGTGCCAACTTTCCGGAGCCGCGCCGGGCCCCCACCTGCAGCCTGGACGGGGCGCTGCCCTTGGGCGCGCAG
AspThrAspProPheAlaCysAlaAsnPheProGluProArgArgAlaProThrCysSerLeuAspGlyAlaLeuProLeuGlyAlaGln 190       200       210       220       230       240       250       260       270
ATACCCGCGGTGCACCGCCTGCTGGGAGCGCCGCTCAAGTTGGAGGATTGTGCTCTGCAAGTGTCTCCCTCCGGATACTACCTGGACACC
IleProAlaValHisArgLeuLeuGlyAlaProLeuLysLeuGluAspCysAlaLeuGlnValSerProSerGlyTyrTyrLeuAspThr 280       290       300       310       320       330       340       350       360
GAGCTGTCCCTGGAAGAGCAGCGGGAGATGCTGGAGGGCTTCTATGAAGAGATCAGCAAAGGGCGGAAGCCCACGCTGATCCTTCGGACC
GluLeuSerLeuGluGluGlnArgGluMetLeuGluGlyPheTyrGluGluIleSerLysGlyArgLysProThrLeuIleLeuArgThr 370       380       390       400       410       420       430       440       450
CAGCTCTCTGTGAGGGTCAACGCTATCTTGGAAAAGCTGTATAGCTCCAGTGGTCCTGAGCTCCGCCGCTCCCTCTTCTCACTGAAGCAG
GlnLeuSerValArgValAsnAlaIleLeuGluLysLeuTyrSerSerSerGlyProGluLeuArgArgSerLeuPheSerLeuLysGln 460       470       480       490       500       510       520       530       540
ATCTTCCAGGAGGACAAAGACCTGGTGCCTGAATTTGTGCATTCAGAGGGGCTGAGCTGCCTGATCCGTGTGGGTGCTGCTGCCGACCAC
IlePheGlnGluAspLysAspLeuValProGluPheValHisSerGluGlyLeuSerCysLeuIleArgValGlyAlaAlaAlaAspHis 550       560       570       580       590       600       610       620       630
AACTACCAGAGCTACATCCTTAGAGCGCTCGGCCAGCTGATGCTCTTTGTGGATGGAATGCTGGGGGTGGTGGCCCACAGTGACACTATT
AsnTyrGlnSerTyrIleLeuArgAlaLeuGlyGlnLeuMetLeuPheValAspGlyMetLeuGlyValValAlaHisSerAspThrIle 640       650       660       670       680       690       700       710       720
CAGTGGCTGTACACATTGTGTGCCAGCCTGTCCCGCTTGGTGGTGAAGACAGCCCTGAAGCTGCTGTTGGTGTTTGTAGAATACTCCGAA
GlnTrpLeuTyrThrLeuCysAlaSerLeuSerArgLeuValValLysThrAlaLeuLysLeuLeuLeuValPheValGluTyrSerGlu 730       740       750       760       770       780       790       800       810
AACAACGCACCGCTGTTCATCCGTGCAGTGAACTCTGTGGCCAGCACCACCGGTGCTCCTCCCTGGGCCAATCTGGTGTCCATCCTGGAG
AsnAsnAlaProLeuPheIleArgAlaValAsnSerValAlaSerThrThrGlyAlaProProTrpAlaAsnLeuValSerIleLeuGlu
```

Fig.2

```
        820       830       840       850       860       870       880       890       900
GAGAAGAATGGCGCTGACCCTGAGTTGTTGGTGTACACGGTCACCCTCATCAACAAGACCCTGGCGGCGCTCCCGGACCAGGACTCCTTC
GluLysAsnGlyAlaAspProGluLeuLeuValTyrThrValThrLeuIleAsnLysThrLeuAlaAlaLeuProAspGlnAspSerPhe 910       920       930       940       950       960       970       980       990
TACGATGTGACGGATGCACTGGAGCAGCAGGGCATGGAAGCGCTGGTCCAGCGCCACCTGGGCACTGCGGGCACTGACGTCGACCTGCGC
TyrAspValThrAspAlaLeuGluGlnGlnGlyMetGluAlaLeuValGlnArgHisLeuGlyThrAlaGlyThrAspValAspLeuArg 1000      1010      1020      1030      1040      1050      1060      1070      1080
ACGCAGCTTGTGCTCTACGAGAACGCCCTGAAATTGGAGGATGGAGACATCGAAGAAGCCCCAGGCGCTGGTGGGCGGCGGGAACGACGA
ThrGlnLeuValLeuTyrGluAsnAlaLeuLysLeuGluAspGlyAspIleGluGluAlaProGlyAlaGlyGlyArgArgGluArgArg 1090      1100      1110      1120      1130      1140      1150      1160      1170
AAGCCTTCTTCTGAGGAGGGCAAGAGGAGCCGCCGTTCTCTGGAAGGCGGGGGCTGCCCCGCGCGTGCCCCGGAACCTGGCCCCACAGGC
LysProSerSerGluGluGlyLysArgSerArgArgSerLeuGluGlyGlyGlyCysProAlaArgAlaProGluProGlyProThrGly 1180      1190      1200      1210      1220      1230      1240      1250      1260
CCCGCCTCACCGGTAGGCCCCACCTCTTCCACCGGCCCCGCCCTGCTGACAGGCCCCGCCTCCAGCCCTGTGGGCCCTCCCTCCGGTCTC
ProAlaSerProValGlyProThrSerSerThrGlyProAlaLeuLeuThrGlyProAlaSerSerProValGlyProProSerGlyLeu 1270      1280      1290      1300      1310      1320      1330      1340      1350
CAAGCTTCAGTGAACCTTTTTCCTACCATCTCTGTGGCACCCTCAGCTGACACCTCCAGCGAGAGGAGCATCTACAAACTTCACCAAACT
GlnAlaSerValAsnLeuPheProThrIleSerValAlaProSerAlaAspThrSerSerGluArgSerIleTyrLysLeuHisGlnThr 1360      1370      1380      1390      1400      1410      1420      1430      1440
GCTTCCGTTTGGGCCCCTGAGAGCCCACCCGTCCCCCAGTCCCCTCCTGGGCAGGCCACGCTGGAAGCCCGGTTCCTGGAGAATGTGGCG
AlaSerValTrpAlaProGluSerProProValProGlnSerProProGlyGlnAlaArgLeuGluAlaArgPheLeuGluAsnValAla 1450      1460      1470      1480      1490      1500      1510      1520      1530
GCAGCAGAAACAGAGAAGCAGGTTGCGCTGGCCCAGGGCCGGGCAGAGACACTTGCCGGGGCCATGCCCAATGAGGCGGGTGGACACCCA
AlaAlaGluThrGluLysGlnValAlaLeuAlaGlnGlyArgAlaGluThrLeuAlaGlyAlaMetProAsnGluAlaGlyGlyHisPro 1540      1550      1560      1570      1580      1590      1600      1610      1620
GATGCCCGGCAACTCTGGGACTCCCCAGAGACAGCCCCTGCAGCCAGAACACCCCAGAGCCCTGCCCCCTGTGTCCTGCTCCGGGCCCAG
AspAlaArgGlnLeuTrpAspSerProGluThrAlaProAlaAlaArgThrProGlnSerProAlaProCysValLeuLeuArgAlaGln
```

Fig.3

```
          1630      1640      1650      1660      1670      1680      1690      1700      1710
CGAAGCCTTGCACCAGAGCCCAAGGAGCCACTGATACCAGCAAGCCCCAAGGCTGAGCCCATCTGGGAGCTCCCTACCCGTGCACCCAGG
ArgSerLeuAlaProGluProLysGluProLeuIleProAlaSerProLysAlaGluProIleTrpGluLeuProThrArgAlaProArg 1720      1730      1740      1750      1760      1770      1780      1790      1800
CTCTCTATTGGGCACCTGGACTTTTCAGATCTAGGGGAGGATGAAGACCAGGACATGCTGAATGTAGAGTCTGTGGAGGCTGGGAAAGAC
LeuSerIleGlyAspLeuAspPheSerAspLeuGlyGluAspGluAspGlnAspMetLeuAsnValGluSerValGluAlaGlyLysAsp 1810      1820      1830      1840      1850      1860      1870      1880      1890
ATCCCAGCTCCCTCACCCCCACTGCCCCTGCTCTCGGGAGTACCCCCCCCTCCCCCACTTCCACCTCCCCCACCCATCAAAGGCCCCTTC
IleProAlaProSerProProLeuProLeuLeuSerGlyValProProProProProLeuProProProProIleLysGlyProPhe 1900      1910      1920      1930      1940      1950      1960      1970      1980
CCACCACCTCCACCTCTACCTCTGGCTGCCCCTCTTCCCCATTCAGTGCCTGACAGCTCAGCCCTCCCCACTAAGAGGAAGACAGTAAAA
ProProProProProLeuProLeuAlaAlaProLeuProHisSerValProAspSerSerAlaLeuProThrLysArgLysThrValLys 1990      2000      2010      2020      2030      2040      2050      2060      2070
CTTTTCTGGCGTGAGCTGAAGCTGGCTGGGGGCCATGGAGTCTCTGCAAGCCGCTTTGGGCCCTGCGCCACCCTCTGGGCTTCACTGGAC
LeuPheTrpArgGluLeuLysLeuAlaGlyGlyHisGlyValSerAlaSerArgPheGlyProCysAlaThrLeuTrpAlaSerLeuAsp 2080      2090      2100      2110      2120      2130      2140      2150      2160
CCTGTCTCAGTGGACACGGCCCGACTGGAACACCTCTTTGAGTCTCGTGCCAAAGAGGTGCTGCCCTCCAAGAAAGCTGGAGAGGGCCGC
ProValSerValAspThrAlaArgLeuGluHisLeuPheGluSerArgAlaLysGluValLeuProSerLysLysAlaGlyGluGlyArg 2170      2180      2190      2200      2210      2220      2230      2240      2250
CGGACAATGACCACAGTGCTGGACCCCAAGCGCAGCAACGCCATCAACATCGGCCTAACCACACTGCCACCTGTGCATGTCATTAAGGCT
ArgThrMetThrThrValLeuAspProLysArgSerAsnAlaIleAsnIleGlyLeuThrThrLeuProProValHisValIleLysAla 2260      2270      2280      2290      2300      2310      2320      2330      2340
GCTCTGCTCAACTTTGATGAGTTTGCTGTCAGCAAGGATGGCATTGAGAAGCTACTGACCATGATGCCCACGGAGGAAGAGCGGCAGAAG
AlaLeuLeuAsnPheAspGluPheAlaValSerLysAspGlyIleGluLysLeuLeuThrMetMetProThrGluGluGluArgGlnLys 2350      2360      2370      2380      2390      2400      2410      2420      2430
ATTGAGGAAGCCCAGCTGGCCAACCCTGACATACCCCTGGGCCCAGCCGAGAACTTCCTGATGACTCTTGCCTCCATTGGCGGCCTCGCT
IleGluGluAlaGlnLeuAlaAsnProAspIleProLeuGlyProAlaGluAsnPheLeuMetThrLeuAlaSerIleGlyGlyLeuAla
```

Fig.4

```
        2440      2450      2460      2470      2480      2490      2500      2510      2520
GCTCGTCTACAACTCTGGGCCTTCAAGCTGGACTATGACAGCATGGAGCGGGAAATTGCTGAGCCACTGTTTGACCTGAAAGTGGGTATG
AlaArgLeuGlnLeuTrpAlaPheLysLeuAspTyrAspSerMetGluArgGluIleAlaGluProLeuPheAspLeuLysValGlyMet 2530      2540      2550      2560      2570      2580      2590      2600      2610
GAACAGCTGGTACAGAATGCCACCTTCCGCTGCATCCTGGCTACCCTCCTAGCGGTGGGCAACTTCCTCAATGGCTCCCAGAGCAGCGGC
GluGlnLeuValGlnAsnAlaThrPheArgCysIleLeuAlaThrLeuLeuAlaValGlyAsnPheLeuAsnGlySerGlnSerSerGly 2620      2630      2640      2650      2660      2670      2680      2690      2700
TTTGAGCTGAGCTACCTGGAGAAGGTGTCAGAGGTGAAGGACACGGTGCGTCGACAGTCACTGCTACACCATCTCTGCTCCCTAGTGCTC
PheGluLeuSerTyrLeuGluLysValSerGluValLysAspThrValArgArgGlnSerLeuLeuHisHisLeuCysSerLeuValLeu 2710      2720      2730      2740      2750      2760      2770      2780      2790
CAGACCCGGCCTGAGTCCTCTGACCTCTATTCAGAAATCCCTGCCCTGACCCGCTGTGCCAAGGTGGACTTTGAACAGCTGACTGAGAAC
GlnThrArgProGluSerSerAspLeuTyrSerGluIleProAlaLeuThrArgCysAlaLysValAspPheGluGlnLeuThrGluAsn 2800      2810      2820      2830      2840      2850      2860      2870      2880
CTCGGGCAGCTGGAGCGCCGGAGCCGGGCAGCCGAGGAGAGCCTGCGGAGCTTGGCCAAGCATGAGCTGGCCCCAGCCCTGCGTGCCCGC
LeuGlyGlnLeuGluArgArgSerArgAlaAlaGluGluSerLeuArgSerLeuAlaLysHisGluLeuAlaProAlaLeuArgAlaArg 2890      2900      2910      2920      2930      2940      2950      2960      2970
CTCACCCACTTCCTGGACCAGTGTGCCCGCCGTGTTGCCATGCTAAGGATAGTGCACCGCCGTGTCTGCAATAGGTTCCATGCCTTCCTG
LeuThrHisPheLeuAspGlnCysAlaArgArgValAlaMetLeuArgIleValHisArgArgValCysAsnArgPheHisAlaPheLeu 2980      2990      3000      3010      3020      3030      3040      3050      3060
CTCTACCTGGGCTACACCCCGCAGGCGGCCCGTGAAGTGCGCATCATGCAGTTCTGCCACACGCTGCGGGAATTTGCGCTTGAGTATCGG
LeuTyrLeuGlyTyrThrProGlnAlaAlaArgGluValArgIleMetGlnPheCysHisThrLeuArgGluPheAlaLeuGluTyrArg 3070      3080      3090      3100      3110      3120      3130      3140      3150
ACTTGCCGGGAACGAGTGCTACAGCAGCAGCAGAAGCAGGCCACATACCGTGAGCGCAACAAGACCCGGGGACGCATGATCACCGAGACA
ThrCysArgGluArgValLeuGlnGlnGlnGlnLysGlnAlaThrTyrArgGluArgAsnLysThrArgGlyArgMetIleThrGluThr 3160      3170      3180      3190      3200      3210      3220      3230      3240
GAGAAGTTCTCAGGTGTGGCTGGGGAAGCCCCCAGCAACCCCTCTGTCCCAGTAGCAGTGAGCAGCGGGCCAGCCCGGGGACATGCTGAC
GluLysPheSerGlyValAlaGlyGluAlaProSerAsnProSerValProValAlaValSerSerGlyProGlyArgGlyAspAlaAsp
```

Fig.5

```
         3250      3260      3270      3280      3290      3300      3310      3320      3330
AGTCATGCTAGTATGAAGACTCTCCTGACCAGCAGGCCTGAGGACACCACACACAATCGCCGCAGCAGAGGCATGGTCCAGAGCAGCTCC
SerHisAlaSerMetLysSerLeuLeuThrSerArgProGluAspThrThrHisAsnArgArgSerArgGlyMetValGlnSerSerSer 3340      3350      3360      3370      3380      3390      3400      3410      3420
CCAATCATGCCCACAGTGGGGCCCTCCACTGCATCCCCAGAAGAACCCCCAGGCTCCAGTTTACCCAGTGATACATCAGATGAGATCATG
ProIleMetProThrValGlyProSerThrAlaSerProGluGluProProGlySerSerLeuProSerAspThrSerAspGluIleMet 3430      3440      3450      3460      3470      3480      3490      3500      3510
GACCTTCTGGTGCAGTCAGTGACCAAGAGCAGTCCTCGTGCCTTAGCTGCTAGGGAACGCAAGCGTTCCCGCGGCAACCGCAAGTCTTTG
AspLeuLeuValGlnSerValThrLysSerSerProArgAlaLeuAlaAlaArgGluArgLysArgSerArgGlyAsnArgLysSerLeu 3520      3530      3540      3550      3560      3570      3580      3590      3600
AGAAGGACGTTGAAGAGTGGGCTCCGAGATGACCTGGTGCAGGCACTGGGACTAAGCAAGGGTCCTGGCCTGGAGGTGTGAAGGTGCTGT
ArgArgThrLeuLysSerGlyLeuGlyAspAspLeuValGlnAlaLeuGlyLeuSerLysGlyProGlyLeuGluVal***

3610      3620      3630      3640      3650      3660      3670      3680      3690
ATCCCGGAAATCTATCTGGACCCTGGACTGCAGTGCAGGAGATGACAGAGTGAGGAGGGCCCAGAGCAGAATTCTGGCCCCAGAACTCTG 3700      3710      3720      3730      3740      3750      3760      3770      3780
TGCCCAGGAGCCATGCCTTGAGCAGTATTAGCCGTGTGTGTATGCATGTGAGTGTGTGTGTATGTGTGTGTGCATGCATATGCATGTG 3790      3800      3810      3820      3830      3840      3850      3860
CATGTGTGTGAGCTCCTTGAACGCACGGAGCAAAATAAAATTTTCTTAGCTAATCCAAAAAAAAAAAAAAAAA
```

Fig.6

```
          10        20        30        40        50        60        70        80        90
TGACCCGCCCGCAGAGCCATGGCGGGCGGGGAAGACCGCGGGGACGGAGAGCCGGTATCAGTGGTGACCGTGAGGGTGCAGTACCTGGAA
                     MetAlaGlyGlyGluAspArgGlyAspGlyGluProValSerValValThrValArgValGlnTyrLeuGlu 100       110       120       130       140       150       160       170       180
GACACCGACCCCTTCGCATGTGCCAACTTTCCGGAGCCGCGCCGGGCCCCCACCTGCAGCCTGGACGGGGCGCTGCCCTTGGGCGCGCAG
AspThrAspProPheAlaCysAlaAsnPheProGluProArgArgAlaProThrCysSerLeuAspGlyAlaLeuProLeuGlyAlaGln 190       200       210       220       230       240       250       260       270
ATACCCGCGGTGCACCGCCTGCTGGGAGCGCCGCTCAAGTTGGAGGATTGTGCCTCTGCAAGTGTCTCCCTCCGGATACTACCTGGACACC
IleProAlaValHisArgLeuLeuGlyAlaProLeuLysLeuGluAspCysAlaLeuGlnValSerProSerGlyTyrTyrLeuAspThr 280       290       300       310       320       330       340       350       360
GAGCTGTCCCTGGAAGAGCACCGGGACATGCTGGAGGGCTTCTATGAAGAGATCAGCAAAGGGCGGAAGCCCACGCTGATCCTTCGGACC
GluLeuSerLeuGluGluGlnArgGluMetLeuGluGlyPheTyrGluGluIleSerLysGlyArgLysProThrLeuIleLeuArgThr 370       380       390       400       410       420       430       440       450
CACCTCTCTGTGAGGGTCAACGCTATCTTGGAAAAGCTGTATAGCTCCAGTGGTCCTGACCCTCCGCCGCTCCCTCTTCTCACTGAAGCAG
GlnLeuSerValArgValAsnAlaIleLeuGluLysLeuTyrSerSerSerGlyProGluLeuArgArgSerLeuPheSerLeuLysGln 460       470       480       490       500       510       520       530       540
ATCTTCCAGGAGGACAAAGACCTGGTGCCTGAATTTGTGCATTCAGAGGGGCTGAGCTGCCTGATCCGTGTGGGTGCTGCTGCCGACCAC
IlePheGlnGluAspLysAspLeuValProGluPheValHisSerGluGlyLeuSerCysLeuIleArgValGlyAlaAlaAlaAspHis 550       560       570       580       590       600       610       620       630
AACTACCAGAGCTACATCCTTAGAGCGCTCGGCCAGCTGATGCTCTTTGTGGATGGAATGCTGGGGGTGGTGGCCCACAGTGACACTATT
AsnTyrGlnSerTyrIleLeuArgAlaLeuGlyGlnLeuMetLeuPheValAspGlyMetLeuGlyValValAlaHisSerAspThrIle 640       650       660       670       680       690       700       710       720
CAGTGGCTGTACACATTGTGTGCCAGCCTGTCCCGCTTGGTGGTGAAGACAGCCCTGAAGCTGCTGTTGGTGTTTGTAGAATACTCCGAA
GlnTrpLeuTyrThrLeuCysAlaSerLeuSerArgLeuValValLysThrAlaLeuLysLeuLeuLeuValPheValGluTyrSerGlu 730       740       750       760       770       780       790       800       810
AACAACGCACCGCTGTTCATCCGTGCAGTGAACTCTGTGGCCAGCACCACCGGTGCTCCTCCCTGCCCAATCTGGTGTCCATCCTGGAG
AsnAsnAlaProLeuPheIleArgAlaValAsnSerValAlaSerThrThrGlyAlaProProTrpAlaAsnLeuValSerIleLeuGlu
```

Fig. 7

```
      820       830       840       850       860       870       880       890       900
GAGAAGAATGGCGCTGACCCTGAGTTGTTGGTGTACACGGTCACCCTCATCAACAAGACGCTGGCGGCGCTCCCGGACCAGGACTCCTTC
GluLysAsnGlyAlaAspProGluLeuLeuValTyrThrValThrLeuIleAsnLysThrLeuAlaAlaLeuProAspGlnAspSerPhe 910       920       930       940       950       960       970       980       990
TACGATGTGACGGATGCACTGGAGCAGCAGGGCATGGAAGCGCTGGTCCAGCGCCACCTGGGCACTGCGGGCACTGACGTCGACCTGCGC
TyrAspValThrAspAlaLeuGluGlnGlnGlyMetGluAlaLeuValGlnArgHisLeuGlyThrAlaGlyThrAspValAspLeuArg 1000      1010      1020      1030      1040      1050      1060      1070      1080
ACGCAGCTTGTGCTCTACGAGAACGCCCTGAAATTGGAGGATGGAGACATCGAAGAAGCCCCAGGCGCTGGTGGGCGGCGGGAACGACGA
ThrGlnLeuValLeuTyrGluAsnAlaLeuLysLeuGluAspGlyAspIleGluGluAlaProGlyAlaGlyGlyArgArgGluArgArg 1090      1100      1110      1120      1130      1140      1150      1160      1170
AAGCCTTCTTCTGAGGAGGGCAAGAGGAGCCGCCGTTCTCTGGAAGGCGGGGGCTGCCCCGCGCGTGCCCCGGAACCTGGCCCCACAGGC
LysProSerSerGluGluGlyLysArgSerArgArgSerLeuGluGlyGlyGlyCysProAlaArgAlaProGluProGlyProThrGly 1180      1190      1200      1210      1220      1230      1240      1250      1260
CCCGCCTCACCGGTAGGCCCCACCTCTTCCACCGGCCCCGCCCTGCTGACAGGCCCCGCCTCCAGCCCTGTGGGCCCTCCCTCCGGTCTC
ProAlaSerProValGlyProThrSerSerThrGlyProAlaLeuLeuThrGlyProAlaSerSerProValGlyProProSerGlyLeu 1270      1280      1290      1300      1310      1320      1330      1340      1350
CAAGCTTCAGTGAACCTTTTTCCTACCATCTCTGTGGCACCCTCAGCTGACACCTCCAGCGAGAGGAGCATCTACAAAGCCCGGTTCCTG
GlnAlaSerValAsnLeuPheProThrIleSerValAlaProSerAlaAspThrSerSerGluArgSerIleTyrLysAlaArgPheLeu 1360      1370      1380      1390      1400      1410      1420      1430      1440
GAGAATGTGGCGGCAGCAGAAACAGAGAAGCAGGTTGCGCTGGCCCAGGGCCGGGCAGAGACACTTGCCGGGGCCATGCCCAATGAGGCG
GluAsnValAlaAlaAlaGluThrGluLysGlnValAlaLeuAlaGlnGlyArgAlaGluThrLeuAlaGlyAlaMetProAsnGluAla 1450      1460      1470      1480      1490      1500      1510      1520      1530
GGTGGACACCCAGATGCCCGGCAACTCTGGGACTCCCCAGAGACAGCCCCTGCAGCCAGAACACCCCAGAGCCCTGCCCCCTGTGTCCTG
GlyGlyHisProAspAlaArgGlnLeuTrpAspSerProGluThrAlaProAlaAlaArgThrProGlnSerProAlaProCysValLeu 1540      1550      1560      1570      1580      1590      1600      1610      1620
CTCCGGGCCCAGCGAAGCCTTGCACCAGAGCCCAAGGAGCCACTGATACCAGCAAGCCCCAAGGCTGAGCCCATCTGGGAGCTCCCTACC
LeuArgAlaGlnArgSerLeuAlaProGluProLysGluProLeuIleProAlaSerProLysAlaGluProIleTrpGluLeuProThr
```

Fig.8

```
         1630      1640      1650      1660      1670      1680      1690      1700      1710
CGTGCACCCAGGCTCTCTATTGGGGACCTGGACTTTTCAGATCTAGCGGAGGATGAAGACCAGGACATGCTGAATGTAGAGTCTGTGGAG
ArgAlaProArgLeuSerIleGlyAspLeuAspPheSerAspLeuGlyGluAspGluAspGlnAspMetLeuAsnValGluSerValGlu 1720      1730      1740      1750      1760      1770      1780      1790      1800
GCTGGGAAAGACATCCCAGCTCCCTCACCCCCACTGCCCCTGCTCTCGGGAGTACCCCCCCCTCCCCCAGTTCCACCTCCCCCACCCATC
AlaGlyLysAspIleProAlaProSerProProLeuProLeuLeuSerGlyValProProProProLeuProProProProIle 1810      1820      1830      1840      1850      1860      1870      1880      1890
AAAGGCCCCTTCCCACCACCTCCACCTCTACCTCTGGCTGCCCCTCTTCCCCATTCAGTGCCTGACAGCTCAGCCCTCCCCACTAAGAGG
LysGlyProPheProProProProProLeuProLeuAlaAlaProLeuProHisSerValProAspSerSerAlaLeuProThrLysArg 1900      1910      1920      1930      1940      1950      1960      1970      1980
AAGACAGTAAAACTTTTCTGGCGTGAGCTGAAGCTGGCTGGGGGCCATGGAGTCTCTGCAAGCCGCTTTGGGCCCTGCGCCACCCTCTGG
LysThrValLysLeuPheTrpArgGluLeuLysLeuAlaGlyGlyHisGlyValSerAlaSerArgPheGlyProCysAlaThrLeuTrp 1990      2000      2010      2020      2030      2040      2050      2060      2070
GCTTCACTGGACCCTGTCTCAGTGGACACGGCCCGACTGGAACACCTCTTTGAGTCTCGTGCCAAAGAGGTGCTGCCCTCCAAGAAAGCT
AlaSerLeuAspProValSerValAspThrAlaArgLeuGluHisLeuPheGluSerArgAlaLysGluValLeuProSerLysLysAla 2080      2090      2100      2110      2120      2130      2140      2150      2160
GGAGAGGGCCGCCGGACAATGACCACAGTGCTGGACCCCAAGCGCAGCAACGCCATCAACATCGGCCTAACCACACTGCCACCTGTGCAT
GlyGluGlyArgArgThrMetThrThrValLeuAspProLysArgSerAsnAlaIleAsnIleGlyLeuThrThrLeuProProValHis 2170      2180      2190      2200      2210      2220      2230      2240      2250
GTCATTAAGGCTGCTCTGCTCAACTTTGATGAGTTTGCTGTCAGCAAGGATGGCATTGAGAAGCTACTGACCATGATGCCCACGGAGGAA
ValIleLysAlaAlaLeuLeuAsnPheAspGluPheAlaValSerLysAspGlyIleGluLysLeuLeuThrMetMetProThrGluGlu 2260      2270      2280      2290      2300      2310      2320      2330      2340
GAGCGGCAGAAGATTGAGGAAGCCCAGCTGGCCAACCCTGACATACCCCTGGGCCCAGCCGAGAACTTCCTGATGACTCTTGCCTCCATT
GluArgGlnLysIleGluGluAlaGlnLeuAlaAsnProAspIleProLeuGlyProAlaGluAsnPheLeuMetThrLeuAlaSerIle 2350      2360      2370      2380      2390      2400      2410      2420      2430
GGCCGCCTCGCTGCTCGTCTACAACTCTGGGCCTTCAAGCTGGACTATGACAGCATGGAGCGGGAAATTGCTGAGCCACTGTTTGACCTG
GlyGlyLeuAlaAlaArgLeuGlnLeuTrpAlaPheLysLeuAspTyrAspSerMetGluArgGluIleAlaGluProLeuPheAspLeu
```

Fig.9

```
      2440      2450      2460      2470      2480      2490      2500      2510      2520
AAAGTGGGTATGGAACAGCTGGTACAGAATGCCACCTTCCGCTGCATCCTGGCTACCCTCCTAGCGGTGGGCAACTTCCTCAATGGCTCC
LysValGlyMetGluGlnLeuValGlnAsnAlaThrPheArgCysIleLeuAlaThrLeuLeuAlaValGlyAsnPheLeuAsnGlySer 2530      2540      2550      2560      2570      2580      2590      2600      2610
CAGAGCAGCGGCTTTGAGCTGAGCTACCTGGAGAAGGTGTCAGAGGTGAAGGACACGGTGCGTCGACAGTCACTGCTACACCATCTCTGC
GlnSerSerGlyPheGluLeuSerTyrLeuGluLysValSerGluValLysAspThrValArgArgGlnSerLeuLeuHisHisLeuCys 2620      2630      2640      2650      2660      2670      2680      2690      2700
TCCCTAGTGCTCCAGACCCGGCCTGAGTCCTCTGACCTCTATTCAGAAATCCCTGCCCTGACCCGCTGTGCCAAGGTGGACTTTGAACAG
SerLeuValLeuGlnThrArgProGluSerSerAspLeuTyrSerGluIleProAlaLeuThrArgCysAlaLysValAspPheGluGln 2710      2720      2730      2740      2750      2760      2770      2780      2790
CTGACTGAGAACCTGGGGCAGCTGGAGCGCCGGAGCCGGGCAGCCGAGGAGAGCCTGCGGAGCTTGGCCAAGCATGAGCTGGCCCCAGCC
LeuThrGluAsnLeuGlyGlnLeuGluArgArgSerArgAlaAlaGluGluSerLeuArgSerLeuAlaLysHisGluLeuAlaProAla 2800      2810      2820      2830      2840      2850      2860      2870      2880
CTGCGTGCCCGCCTCACCCACTTCCTGGACCAGTGTGCCCGCCGTGTTGCCATGCTAAGGATAGTGCACCGCCGTGTCTGCAATAGGTTC
LeuArgAlaArgLeuThrHisPheLeuAspGlnCysAlaArgArgValAlaMetLeuArgIleValHisArgArgValCysAsnArgPhe 2890      2900      2910      2920      2930      2940      2950      2960      2970
CATGCCTTCCTGCTCTACCTGGGCTACACCCCGCAGGCGGCCCCGTGAAGTGCGCATCATGCAGTTCTGCCACACGCTGCGGGAATTTGCG
HisAlaPheLeuLeuTyrLeuGlyTyrThrProGlnAlaAlaArgGluValArgIleMetGlnPheCysHisThrLeuArgGluPheAla 2980      2990      3000      3010      3020      3030      3040      3050      3060
CTTGAGTATCGGACTTGCCGGGAACGAGTGCTACAGCAGCAGCAGAAGCAGGCCACATACCGTGAGCGCAACAAGACCCGGGGACGCATG
LeuGluTyrArgThrCysArgGluArgValLeuGlnGlnGlnGlnLysGlnAlaThrTyrArgGluArgAsnLysThrArgGlyArgMet 3070      3080      3090      3100      3110      3120      3130      3140      3150
ATCACCGAGACAGAGAAGTTCTCAGGTGTGGCTGGGGAAGCCCCCAGCAACCCCTCTGTCCCAGTAGCAGTGAGCAGCGGGCCAGGCCGG
IleThrGluThrGluLysPheSerGlyValAlaGlyGluAlaProSerAsnProSerValProValAlaValSerSerGlyProGlyArg 3160      3170      3180      3190      3200      3210      3220      3230      3240
GGAGATGCTGACAGTCATGCTAGTATGAAGAGTCTGCTGACCAGCAGGCCTGAGGACACCACACACAATCGCCGCAGCAGAGGCATGGTC
GlyAspAlaAspSerHisAlaSerMetLysSerLeuLeuThrSerArgProGluAspThrThrHisAsnArgArgSerArgGlyMetVal
```

Fig.10

```
          3250      3260      3270      3280      3290      3300      3310      3320      3330
CAGAGCAGCTCCCCAATCATGCCCACAGTGCGGCCCTCCACTGCATCCCCAGAAGAACCCCCAGGCTCCAGTTTACCCAGTGATACATCA
GlnSerSerSerProIleMetProThrValGlyProSerThrAlaSerProGluGluProProGlySerSerLeuProSerAspThrSer 3340      3350      3360      3370      3380      3390      3400      3410      3420
GATGAGATCATGGACCTTCTGGTGCAGTCAGTGACCAAGAGCAGTCCTCGTGCCTTAGCTGCTAGGGAACGCAAGCGTTCCCGCGGCAAC
AspGluIleMetAspLeuLeuValGlnSerValThrLysSerSerProArgAlaLeuAlaAlaArgGluArgLysArgSerArgGlyAsn 3430      3440      3450      3460      3470      3480      3490      3500      3510
CGCAAGTCTTTGAGAAGGACGTTGAAGAGTGGGCTCGGAGATGACCTGGTGCAGGCACTGGGACTAAGCAAGGGTCCTGGCCTGGAGGTG
ArgLysSerLeuArgArgThrLeuLysSerGlyLeuGlyAspAspLeuValGlnAlaLeuGlyLeuSerLysGlyProGlyLeuGluVal 3520      3530      3540      3550      3560      3570      3580      3590      3600
TGAAGGTGCTGTATCCCCGAAATCTATCTGGACCCTGGACTGCAGTGCAGGAGATGACAGAGTGAGGAGGGCCCAGAGCAGAATTCTGCC
***

3610      3620      3630      3640      3650      3660      3670      3680      3690
CCCAGAACTCTGTGCCCAGGAGCCATGCCTTGAGCAGTATTAGCCGTGTGTGTATGCATCTGAGTGTGTGTGTATGTGTGTGTGCCATG 3700      3710      3720      3730      3740      3750      3760      3770      3780
CATATGCATGTGCATGTGTGTGAGCTCCTTGAACGCACGGAGCAAAATAAAATTTTCTTAGCTAATCCAAAAAAAAAAAAAAAAAA
```

Fig.11

```
         10        20        30        40        50        60        70        80        90
TGAGCCGGCCGCAGAGCCATGGCGGCGGGGAAGACCCGCGGGGACGGACAGCCGGTATCAGTGGTGACCGTGAGGGTGCAGTACCTGGAA
                  MetAlaGlyGlyGluAspArgGlyAspGlyGluProValSerValValThrValArgValGlnTyrLeuGlu 100       110       120       130       140       150       160       170       180
GACACCGACCCCTTCGCATGTGCCAACTTTCCGGAGCCGCGCCGGGCCCCCACCTGCAGCCTGGACGGGGCGCTGCCCTTGGGCGCGCAG
AspThrAspProPheAlaCysAlaAsnPheProGluProArgArgAlaProThrCysSerLeuAspGlyAlaLeuProLeuGlyAlaGln 190       200       210       220       230       240       250       260       270
ATACCCGCGGTGCACCGCCTGCTGGGAGCGCCGCTCAAGTTGGAGGATTGTGCTCTGCAAGTGTCTCCCTCCGGATACTACCTGGACACC
IleProAlaValHisArgLeuLeuGlyAlaProLeuLysLeuGluAspCysAlaLeuGlnValSerProSerGlyTyrTyrLeuAspThr 280       290       300       310       320       330       340       350       360
GAGCTGTCCCTGGAAGAGCAGCGGGAGATGCTGGAGGGCTTCTATGAAGAGATCAGCAAAGGGCGGAAGCCCACGCTGATCCTTCGGACC
GluLeuSerLeuGluGluGlnArgGluMetLeuGluGlyPheTyrGluGluIleSerLysGlyArgLysProThrLeuIleLeuArgThr 370       380       390       400       410       420       430       440       450
CAGCTCTCTGTGAGGGTCAACGCTATCTTGGAAAAGCTGTATAGCTCCAGTGGTCCTGAGCTCCGCCGCTCCCTCTTCTCACTGAAGCAG
GlnLeuSerValArgValAsnAlaIleLeuGluLysLeuTyrSerSerSerGlyProGluLeuArgArgSerLeuPheSerLeuLysGln 460       470       480       490       500       510       520       530       540
ATCTTCCAGGAGGACAAAGACCTGGTGCCTGAATTTGTGCATTCAGAGGGGCTGAGCTGCCTGATCCGTGTGGGTGCTGCTGCCGACCAC
IlePheGlnGluAspLysAspLeuValProGluPheValHisSerGluGlyLeuSerCysLeuIleArgValGlyAlaAlaAlaAspHis 550       560       570       580       590       600       610       620       630
AACTACCAGAGCTACATCCTTAGAGCGCTCGGCCAGCTGATGCTCTTTGTGGATGGAATGCTGGGGGTGGTGGCCCACAGTGACACTATT
AsnTyrGlnSerTyrIleLeuArgAlaLeuGlyGlnLeuMetLeuPheValAspGlyMetLeuGlyValValAlaHisSerAspThrIle 640       650       660       670       680       690       700       710       720
CAGTGGCTGTACACATTGTGTGCCAGCCTGTCCCGCTTGGTGGTGAAGACAGCCCTGAAGCTGCTGTTGGTGTTTGTAGAATACTCCGAA
GlnTrpLeuTyrThrLeuCysAlaSerLeuSerArgLeuValValLysThrAlaLeuLysLeuLeuLeuValPheValGluTyrSerGlu 730       740       750       760       770       780       790       800       810
AACAACGCACCGCTGTTCATCCGTGCAGTGAACTCTGTGGCCAGCACCACCGGTGCTCCTCCCTGGGCCAATCTGGTGTCCATCCTGGAG
AsnAsnAlaProLeuPheIleArgAlaValAsnSerValAlaSerThrThrGlyAlaProProTrpAlaAsnLeuValSerIleLeuGlu
```

Fig. 12

```
       820       830       840       850       860       870       880       890       900
GAGAAGAATGGCGCTGACCCTGAGTTGTTGGTGTACACGGTCACCCTCATCAACAAGACGCTGGCCGCCGCTCCCGGACCAGGACTCCTTC
GluLysAsnGlyAlaAspProGluLeuLeuValTyrThrValThrLeuIleAsnLysThrLeuAlaAlaLeuProAspGlnAspSerPhe 910       920       930       940       950       960       970       980       990
TACGATGTGACGGATGCACTGGAGCAGCAGGGCATGGAACCGCTGGTCCAGCGCCACCTGGGCACTGCGGGCACTGACGTCGACCTGCGC
TyrAspValThrAspAlaLeuGluGlnGlnGlyMetGluAlaLeuValGlnArgHisLeuGlyThrAlaGlyThrAspValAspLeuArg 1000      1010      1020      1030      1040      1050      1060      1070      1080
ACGCAGCTTGTGCTCTACGAGAACGCCCTGAAATTGGAGGATGGAGACATCGAAGAAGCCCCAGGCGCTGGTGGGCGGCGGGAACGACGA
ThrGlnLeuValLeuTyrGluAsnAlaLeuLysLeuGluAspGlyAspIleGluGluAlaProGlyAlaGlyGlyArgArgGluArgArg 1090      1100      1110      1120      1130      1140      1150      1160      1170
AAGCCTTCTTCTGAGGAGGGCAAGAGGAGCCGCCGTTCTCTGGAAGGCGGGGGCTGCCCCGCGCGTGCCCCGGAACCTGGCCCCACAGGC
LysProSerSerGluGluGlyLysArgSerArgArgSerLeuGluGlyGlyGlyCysProAlaArgAlaProGluProGlyProThrGly 1180      1190      1200      1210      1220      1230      1240      1250      1260
CCCGCCTCACCGGTAGGCCCCACCTCTTCCACCGGCCCCGCCCTGCTGACAGGCCCCGCCTCCAGCCCTGTGGGCCCTCCCTCCGGTCTC
ProAlaSerProValGlyProThrSerSerThrGlyProAlaLeuLeuThrGlyProAlaSerSerProValGlyProProSerGlyLeu 1270      1280      1290      1300      1310      1320      1330      1340      1350
CAAGCTTCAGTGAACCTTTTTCCTACCATCTCTGTGGCACCCTCAGCTGACACCTCCAGCGAGAGGAGCATCTACAAACTTCACCAAACT
GlnAlaSerValAsnLeuPheProThrIleSerValAlaProSerAlaAspThrSerSerGluArgSerIleTyrLysLeuHisGlnThr 1360      1370      1380      1390      1400      1410      1420      1430      1440
GCTTCCGTTTGAGCCCGGTTCCTGGAGAATCTGGCGGCAGCAGAAACAGAGAAGCAGGTTGCGCTGGCCCAGGGCCGGGCAGAGACACTT
AlaSerVal***

1450      1460      1470      1480      1490      1500      1510      1520      1530
GCCCGGGCCATGCCCAATGAGGCGGGTGGACACCCAGATGCCCGGCAACTCTGGGACTCCCCAGAGACAGCCCCTGCAGCCAGAACACCC 1540      1550      1560      1570      1580      1590      1600      1610      1620
CAGAGCCCTGCCCCCTGTGTCCTGCTCCGGGCCCAGCGAAGCCTTGCACCAGAGCCCAAGGAGCCACTGATACCAGCAAGCCCCAAGGCT 1630      1640      1650      1660      1670      1680      1690      1700      1710
GAGCCCATCTGGGAGCTCCCTACCCGTGCACCCAGGCTCTCTATTGGGGACCTGGACTTTTCAGATCTAGGGGAGGATGAAGACCAGGAC
```

Fig.13

```
        1720      1730      1740      1750      1760      1770      1780      1790      1800
ATGCTGAATGTAGAGTCTGTGGAGGCTGGGAAAGACATCCCAGCTCCCTCACCCCCACTGCCCCTCCTCTCGGGAGTACCCCCCCCTCCC 1810      1820      1830      1840      1850      1860      1870      1880      1890
CCACTTCCACCTCCCCCACCCATCAAAGGCCCCTTCCCACCACCTCCACCTCTACCTCTGGCTGCCCCTCTTCCCCATTCAGTGCCTGAC 1900      1910      1920      1930      1940      1950      1960      1970      1980
AGCTCAGCCCTCCCCACTAAGAGGAAGACAGTAAAACTTTTCTGGCGTGAGCTGAAGCTGGCTGGGGGCCATGGAGTCTCTGCAAGCCGC 1990      2000      2010      2020      2030      2040      2050      2060      2070
TTTGGGCCCTGCGCCACCCTCTGGGCTTCACTGGACCCTGTCTCAGTGGACACGGCCCGACTGGAACACCTCTTTGAGTCTCGTGCCAAA 2080      2090      2100      2110      2120      2130      2140      2150      2160
GAGGTGCTGCCCTCCAAGAAAGCTGGAGAGGGCCGCCGGACAATGACCACAGTGCTGGACCCCAAGCGCAGCAACGCCATCAACATCGGC 2170      2180      2190      2200      2210      2220      2230      2240      2250
CTAACCACACTGCCACCTGTGCATGTCATTAAGGCTGCTCTGCTCAACTTTGATGAGTTTGCTGTCAGCAAGGATGGCATTGAGAAGCTA 2260      2270      2280      2290      2300      2310      2320      2330      2340
CTGACCATGATGCCCACGGAGGAAGAGCGGCAGAAGATTGAGGAAGCCCAGCTGGCCAACCCTGACATACCCCTGGGCCCAGCCGAGAAC 2350      2360      2370      2380      2390      2400      2410      2420      2430
TTCCTGATGACTCTTGCCTCCATTGGCGGCCTCGCTGCTCGTCTACAACTCTGGGCCTTCAAGCTGGACTATGACAGCATGGAGCGGGAA 2440      2450      2460      2470      2480      2490      2500      2510      2520
ATTGCTGAGCCACTGTTTGACCTGAAAGTGGGTATGGAACAGCTGGTACAGAATGCCACCTTCCGCTGCATCCTGGCTACCCTCCTAGCG 2530      2540      2550      2560      2570      2580      2590      2600      2610
CTGGGCAACTTCCTCAATGGCTCCCAGAGCAGCGGCTTTGAGCTCAGCTACCTGGAGAAGGTGTCAGAGGTGAAGGACACGGTGCGTCGA 2620      2630      2640      2650      2660      2670      2680      2690      2700
CAGTCACTGCTACACCATCTCTGCTCCCTAGTGCTCCAGACCCGGCCTGAGTCCTCTGACCTCTATTCAGAAATCCCTGCCCTGACCCGC 2710      2720      2730      2740      2750      2760      2770      2780      2790
TGTGCCAAGGTGGACTTTGAACAGCTGACTGAGAACCTGGGGCAGCTGGAGCGCCGGAGCCGGGCAGCCGAGGAGAGCCTGCGGAGCTTG
```

Fig.14

```
        2800      2810      2820      2830      2840      2850      2860      2870      2880
GCCAAGCATGAGCTGGCCCCAGCCCTGCGTGCCCGCCTCACCCACTTCCTGGACCAGTGTGCCCGCCGTGTTGCCATGCTAAGGATAGTG 2890      2900      2910      2920      2930      2940      2950      2960      2970
CACCGCCGTGTCTGCAATAGGTTCCATGCCTTCCTGCTCTACCTGGGCTACACCCCGCAGGCGGCCCGTGAAGTGCGCATCATGCAGTTC 2980      2990      3000      3010      3020      3030      3040      3050      3060
TGCCACACGCTGCGGGAATTTGCGCTTGAGTATCGGACTTGCCGGGAACGAGTGCTACAGCAGCAGCAGAAGCAGGCCACATACCGTGAG 3070      3080      3090      3100      3110      3120      3130      3140      3150
CGCAACAAGACCCGGGGACGCATGATCACCGAGACAGAGAAGTTCTCAGGTGTGGCTGGGGAAGCCCCCAGCAACCCCTCTGTCCCAGTA 3160      3170      3180      3190      3200      3210      3220      3230      3240
GCAGTGAGCAGCGGGCCAGGCCGGGGAGATGCTGACAGTCATGCTAGTATGAAGAGTCTGCTGACCAGCAGGCCTGAGGACACCACACAC 3250      3260      3270      3280      3290      3300      3310      3320      3330
AATCGCCGCAGCAGAGGCATGGTCCAGAGCAGCTCCCCAATCATGCCCACAGTGGGGCCCTCCACTGCATCCCCAGAAGAACCCCCAGGC 3340      3350      3360      3370      3380      3390      3400      3410      3420
TCCAGTTTACCCAGTGATACATCAGATGAGATCATGGACCTTCTGGTGCAGTCAGTGACCAAGAGCAGTCCTCGTGCCTTAGCTGCTAGG 3430      3440      3450      3460      3470      3480      3490      3500      3510
GAACGCAAGCGTTCCCGCGGCAACCGCAAGTCTTTGAGAAGGACGTTGAAGAGTGGGCTCGGAGATGACCTGGTGCAGGCACTGGGACTA 3520      3530      3540      3550      3560      3570      3580      3590      3600
AGCAAGGGTCCTGGCCTGGAGGTGTGAAGGTGCTGTATCCCGGAAATCTATCTGGACCCTGGACTGCAGTGCAGGAGATGACAGAGTGAG 3610      3620      3630      3640      3650      3660      3670      3680      3690
GAGGGCCCAGAGCAGAATTCTGGCCCCAGAACTCTGTGCCCAGGAGCCATGCCTTGAGCAGTATTAGCCGTGTGTGTATGCATGTCAGTG 3700      3710      3720      3730      3740      3750      3760      3770      3780
TGTGTGTATGTGTGTGTGTGCATGCATATGCATGTGCATGTGTGTGAGCTCCTTGAACGCACCGAGCAAAATAAAATTTTCTTAGCTAAT 3790      3800
CCAAAAAAAAAAAAAAAAAA
```

Fig. 18
FHOS (ubiquitous)
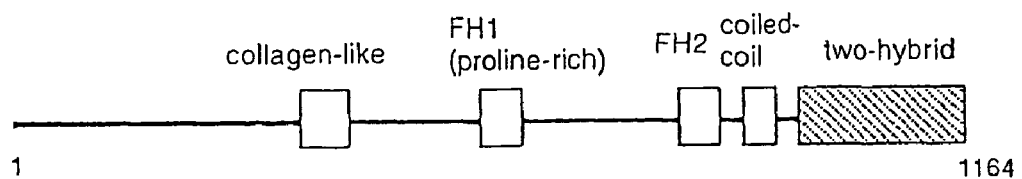
MD36 (skeletal muscle-specific)
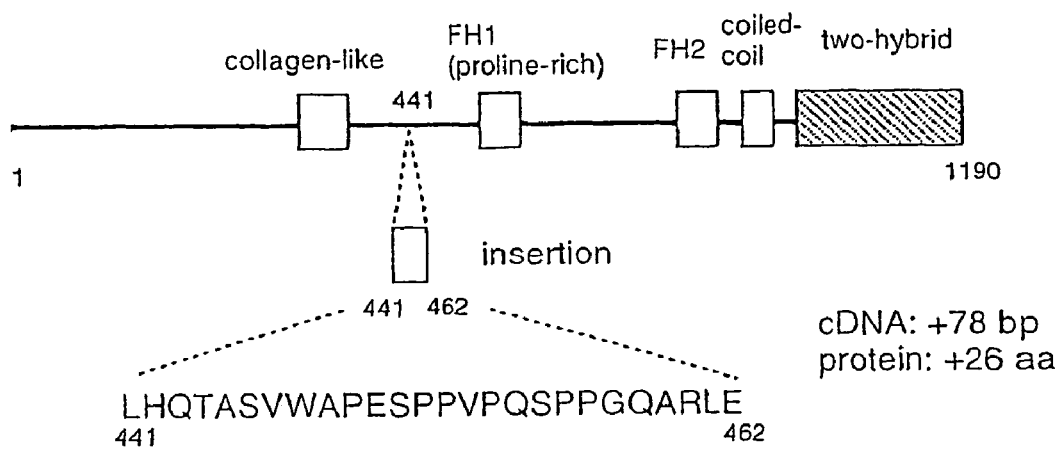
cDNA: +78 bp
protein: +26 aa
Truncated FHOS (ubiquitous)
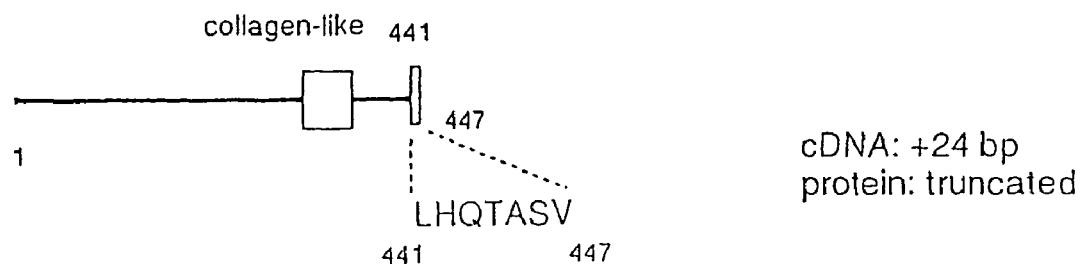
cDNA: +24 bp
protein: truncated

SEQUENCE LISTING

```
<160> NUMBER OF SEQ ID NOS: 35

<210> SEQ ID NO 1
<211> LENGTH: 1190
<212> TYPE: PRT
<213> ORGANISM: Homo sapiens

<400> SEQUENCE: 1

Met Ala Gly Gly Glu Asp Arg Gly Asp Gly Glu Pro Val Ser Val Val
 1               5                  10                  15

Thr Val Arg Val Gln Tyr Leu Glu Asp Thr Asp Pro Phe Ala Cys Ala
            20                  25                  30

Asn Phe Pro Glu Pro Arg Arg Ala Pro Thr Cys Ser Leu Asp Gly Ala
        35                  40                  45

Leu Pro Leu Gly Ala Gln Ile Pro Ala Val His Arg Leu Leu Gly Ala
    50                  55                  60

Pro Leu Lys Leu Glu Asp Cys Ala Leu Gln Val Ser Pro Ser Gly Tyr
65                  70                  75                  80

Tyr Leu Asp Thr Glu Leu Ser Leu Glu Glu Gln Arg Glu Met Leu Glu
                85                  90                  95

Gly Phe Tyr Glu Glu Ile Ser Lys Gly Arg Lys Pro Thr Leu Ile Leu
            100                 105                 110

Arg Thr Gln Leu Ser Val Arg Val Asn Ala Ile Leu Glu Lys Leu Tyr
        115                 120                 125

Ser Ser Ser Gly Pro Glu Leu Arg Arg Ser Leu Phe Ser Leu Lys Gln
    130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Asp Thr Ile Gln Trp Leu Tyr
        195                 200                 205
```

```
Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Arg Ala Val Asn Ser Val Ala Ser Thr Thr Gly Ala Pro Pro Trp
                245                 250                 255

Ala Asn Leu Val Ser Ile Leu Glu Glu Lys Asn Gly Ala Asp Pro Glu
                260                 265                 270

Leu Leu Val Tyr Thr Val Thr Leu Ile Asn Lys Thr Leu Ala Ala Leu
            275                 280                 285

Pro Asp Gln Asp Ser Phe Tyr Asp Val Thr Asp Ala Leu Glu Gln Gln
    290                 295                 300

Gly Met Glu Ala Leu Val Gln Arg His Leu Gly Thr Ala Gly Thr Asp
305                 310                 315                 320

Val Asp Leu Arg Thr Gln Leu Val Leu Tyr Glu Asn Ala Leu Lys Leu
                325                 330                 335

Glu Asp Gly Asp Ile Glu Glu Ala Pro Gly Ala Gly Gly Arg Arg Glu
                340                 345                 350

Arg Arg Lys Pro Ser Ser Glu Glu Gly Lys Arg Ser Arg Arg Ser Leu
            355                 360                 365

Glu Gly Gly Gly Cys Pro Ala Arg Ala Pro Glu Pro Gly Pro Thr Gly
    370                 375                 380

Pro Ala Ser Pro Val Gly Pro Thr Ser Ser Thr Gly Pro Ala Leu Leu
385                 390                 395                 400

Thr Gly Pro Ala Ser Ser Pro Val Gly Pro Pro Ser Gly Leu Gln Ala
                405                 410                 415

Ser Val Asn Leu Phe Pro Thr Ile Ser Val Ala Pro Ser Ala Asp Thr
                420                 425                 430

Ser Ser Glu Arg Ser Ile Tyr Lys Leu His Gln Thr Ala Ser Val Trp
            435                 440                 445

Ala Pro Glu Ser Pro Pro Val Pro Gln Ser Pro Pro Gly Gln Ala Arg
    450                 455                 460

Leu Glu Ala Arg Phe Leu Glu Asn Val Ala Ala Ala Glu Thr Glu Lys
465                 470                 475                 480

Gln Val Ala Leu Ala Gln Gly Arg Ala Glu Thr Leu Ala Gly Ala Met
                485                 490                 495

Pro Asn Glu Ala Gly Gly His Pro Asp Ala Arg Gln Leu Trp Asp Ser
            500                 505                 510

Pro Glu Thr Ala Pro Ala Ala Arg Thr Pro Gln Ser Pro Ala Pro Cys
    515                 520                 525

Val Leu Leu Arg Ala Gln Arg Ser Leu Ala Pro Glu Pro Lys Glu Pro
530                 535                 540

Leu Ile Pro Ala Ser Pro Lys Ala Glu Pro Ile Trp Glu Leu Pro Thr
545                 550                 555                 560

Arg Ala Pro Arg Leu Ser Ile Gly Asp Leu Asp Phe Ser Asp Leu Gly
                565                 570                 575

Glu Asp Glu Asp Gln Asp Met Leu Asn Val Glu Ser Val Glu Ala Gly
                580                 585                 590

Lys Asp Ile Pro Ala Pro Ser Pro Pro Leu Pro Leu Leu Ser Gly Val
            595                 600                 605

Pro Pro Pro Pro Pro Leu Pro Pro Pro Pro Ile Lys Gly Pro Phe
    610                 615                 620
```

-continued

```
Pro Pro Pro Pro Leu Pro Leu Ala Ala Pro Leu Pro His Ser Val
625                 630                 635                 640

Pro Asp Ser Ser Ala Leu Pro Thr Lys Arg Lys Thr Val Lys Leu Phe
            645                 650                 655

Trp Arg Glu Leu Lys Leu Ala Gly Gly His Gly Val Ser Ala Ser Arg
        660                 665                 670

Phe Gly Pro Cys Ala Thr Leu Trp Ala Ser Leu Asp Pro Val Ser Val
    675                 680                 685

Asp Thr Ala Arg Leu Glu His Leu Phe Glu Ser Arg Ala Lys Glu Val
690                 695                 700

Leu Pro Ser Lys Lys Ala Gly Glu Gly Arg Arg Thr Met Thr Thr Val
705                 710                 715                 720

Leu Asp Pro Lys Arg Ser Asn Ala Ile Asn Ile Gly Leu Thr Thr Leu
            725                 730                 735

Pro Pro Val His Val Ile Lys Ala Ala Leu Leu Asn Phe Asp Glu Phe
        740                 745                 750

Ala Val Ser Lys Asp Gly Ile Glu Lys Leu Leu Thr Met Met Pro Thr
    755                 760                 765

Glu Glu Glu Arg Gln Lys Ile Glu Glu Ala Gln Leu Ala Asn Pro Asp
770                 775                 780

Ile Pro Leu Gly Pro Ala Glu Asn Phe Leu Met Thr Leu Ala Ser Ile
785                 790                 795                 800

Gly Gly Leu Ala Ala Arg Leu Gln Leu Trp Ala Phe Lys Leu Asp Tyr
            805                 810                 815

Asp Ser Met Glu Arg Glu Ile Ala Glu Pro Leu Phe Asp Leu Lys Val
        820                 825                 830

Gly Met Glu Gln Leu Val Gln Asn Ala Thr Phe Arg Cys Ile Leu Ala
    835                 840                 845

Thr Leu Leu Ala Val Gly Asn Phe Leu Asn Gly Ser Gln Ser Ser Gly
850                 855                 860

Phe Glu Leu Ser Tyr Leu Glu Lys Val Ser Glu Val Lys Asp Thr Val
865                 870                 875                 880

Arg Arg Gln Ser Leu Leu His His Leu Cys Ser Leu Val Leu Gln Thr
            885                 890                 895

Arg Pro Glu Ser Ser Asp Leu Tyr Ser Glu Ile Pro Ala Leu Thr Arg
        900                 905                 910

Cys Ala Lys Val Asp Phe Glu Gln Leu Thr Glu Asn Leu Gly Gln Leu
    915                 920                 925

Glu Arg Arg Ser Arg Ala Ala Glu Glu Ser Leu Arg Ser Leu Ala Lys
930                 935                 940

His Glu Leu Ala Pro Ala Leu Arg Ala Arg Leu Thr His Phe Leu Asp
945                 950                 955                 960

Gln Cys Ala Arg Arg Val Ala Met Leu Arg Ile Val His Arg Arg Val
            965                 970                 975

Cys Asn Arg Phe His Ala Phe Leu Leu Tyr Leu Gly Tyr Thr Pro Gln
        980                 985                 990

Ala Ala Arg Glu Val Arg Ile Met Gln Phe Cys His Thr Leu Arg Glu
    995                 1000                1005

Phe Ala Leu Glu Tyr Arg Thr Cys Arg Glu Arg Val Leu Gln Gln Gln
    1010                1015                1020

Gln Lys Gln Ala Thr Tyr Arg Glu Arg Asn Lys Thr Arg Gly Arg Met
1025                1030                1035                1040
```

```
Ile Thr Glu Thr Glu Lys Phe Ser Gly Val Ala Gly Glu Ala Pro Ser
                1045                1050                1055

Asn Pro Ser Val Pro Val Ala Val Ser Ser Gly Pro Gly Arg Gly Asp
            1060                1065                1070

Ala Asp Ser His Ala Ser Met Lys Ser Leu Leu Thr Ser Arg Pro Glu
        1075                1080                1085

Asp Thr Thr His Asn Arg Arg Ser Arg Gly Met Val Gln Ser Ser Ser
    1090                1095                1100

Pro Ile Met Pro Thr Val Gly Pro Ser Thr Ala Ser Pro Glu Glu Pro
1105                1110                1115                1120

Pro Gly Ser Ser Leu Pro Ser Asp Thr Ser Asp Glu Ile Met Asp Leu
                1125                1130                1135

Leu Val Gln Ser Val Thr Lys Ser Ser Pro Arg Ala Leu Ala Ala Arg
                1140                1145                1150

Glu Arg Lys Arg Ser Arg Gly Asn Arg Lys Ser Leu Arg Arg Thr Leu
            1155                1160                1165

Lys Ser Gly Leu Gly Asp Asp Leu Val Gln Ala Leu Gly Leu Ser Lys
        1170                1175                1180

Gly Pro Gly Leu Glu Val
1185                1190

<210> SEQ ID NO 2
<211> LENGTH: 1164
<212> TYPE: PRT
<213> ORGANISM: Homo sapiens

<400> SEQUENCE: 2

Met Ala Gly Gly Glu Asp Arg Gly Asp Gly Glu Pro Val Ser Val Val
  1               5                  10                  15

Thr Val Arg Val Gln Tyr Leu Glu Asp Thr Asp Pro Phe Ala Cys Ala
                 20                  25                  30

Asn Phe Pro Glu Pro Arg Arg Ala Pro Thr Cys Ser Leu Asp Gly Ala
             35                  40                  45

Leu Pro Leu Gly Ala Gln Ile Pro Ala Val His Arg Leu Leu Gly Ala
         50                  55                  60

Pro Leu Lys Leu Glu Asp Cys Ala Leu Gln Val Ser Pro Ser Gly Tyr
 65                  70                  75                  80

Tyr Leu Asp Thr Glu Leu Ser Leu Glu Glu Arg Glu Met Leu Glu
                 85                  90                  95

Gly Phe Tyr Glu Glu Ile Ser Lys Gly Arg Lys Pro Thr Leu Ile Leu
                100                 105                 110

Arg Thr Gln Leu Ser Val Arg Val Asn Ala Ile Leu Glu Lys Leu Tyr
            115                 120                 125

Ser Ser Ser Gly Pro Glu Leu Arg Arg Ser Leu Phe Ser Leu Lys Gln
        130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Asp Thr Ile Gln Trp Leu Tyr
        195                 200                 205
```

```
Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Arg Ala Val Asn Ser Val Ala Ser Thr Thr Gly Ala Pro Pro Trp
                245                 250                 255

Ala Asn Leu Val Ser Ile Leu Glu Glu Lys Asn Gly Ala Asp Pro Glu
            260                 265                 270

Leu Leu Val Tyr Thr Val Thr Leu Ile Asn Lys Thr Leu Ala Ala Leu
        275                 280                 285

Pro Asp Gln Asp Ser Phe Tyr Asp Val Thr Asp Ala Leu Glu Gln Gln
    290                 295                 300

Gly Met Glu Ala Leu Val Gln Arg His Leu Gly Thr Ala Gly Thr Asp
305                 310                 315                 320

Val Asp Leu Arg Thr Gln Leu Val Leu Tyr Glu Asn Ala Leu Lys Leu
                325                 330                 335

Glu Asp Gly Asp Ile Glu Glu Ala Pro Gly Ala Gly Gly Arg Arg Glu
            340                 345                 350

Arg Arg Lys Pro Ser Ser Glu Glu Gly Lys Arg Ser Arg Arg Ser Leu
        355                 360                 365

Glu Gly Gly Gly Cys Pro Ala Arg Ala Pro Glu Pro Gly Pro Thr Gly
    370                 375                 380

Pro Ala Ser Pro Val Gly Pro Thr Ser Ser Thr Gly Pro Ala Leu Leu
385                 390                 395                 400

Thr Gly Pro Ala Ser Ser Pro Val Gly Pro Pro Ser Gly Leu Gln Ala
                405                 410                 415

Ser Val Asn Leu Phe Pro Thr Ile Ser Val Ala Pro Ser Ala Asp Thr
            420                 425                 430

Ser Ser Glu Arg Ser Ile Tyr Lys Ala Arg Phe Leu Glu Asn Val Ala
        435                 440                 445

Ala Ala Glu Thr Glu Lys Gln Val Ala Leu Ala Gln Gly Arg Ala Glu
    450                 455                 460

Thr Leu Ala Gly Ala Met Pro Asn Glu Ala Gly Gly His Pro Asp Ala
465                 470                 475                 480

Arg Gln Leu Trp Asp Ser Pro Glu Thr Ala Pro Ala Ala Arg Thr Pro
                485                 490                 495

Gln Ser Pro Ala Pro Cys Val Leu Leu Arg Ala Gln Arg Ser Leu Ala
            500                 505                 510

Pro Glu Pro Lys Glu Pro Leu Ile Pro Ala Ser Pro Lys Ala Glu Pro
        515                 520                 525

Ile Trp Glu Leu Pro Thr Arg Ala Pro Arg Leu Ser Ile Gly Asp Leu
    530                 535                 540

Asp Phe Ser Asp Leu Gly Glu Asp Glu Gln Asp Met Leu Asn Val
545                 550                 555                 560

Glu Ser Val Glu Ala Gly Lys Asp Ile Pro Ala Pro Ser Pro Leu
                565                 570                 575

Pro Leu Leu Ser Gly Val Pro Pro Pro Leu Pro Pro Pro
            580                 585                 590

Pro Ile Lys Gly Pro Phe Pro Pro Pro Pro Leu Pro Leu Ala Ala
        595                 600                 605

Pro Leu Pro His Ser Val Pro Asp Ser Ser Ala Leu Pro Thr Lys Arg
    610                 615                 620
```

```
                         -continued

Lys Thr Val Lys Leu Phe Trp Arg Glu Leu Lys Leu Ala Gly Gly His
625                 630                 635                 640

Gly Val Ser Ala Ser Arg Phe Gly Pro Cys Ala Thr Leu Trp Ala Ser
                645                 650                 655

Leu Asp Pro Val Ser Val Asp Thr Ala Arg Leu Glu His Leu Phe Glu
            660                 665                 670

Ser Arg Ala Lys Glu Val Leu Pro Ser Lys Lys Ala Gly Glu Gly Arg
        675                 680                 685

Arg Thr Met Thr Thr Val Leu Asp Pro Lys Arg Ser Asn Ala Ile Asn
    690                 695                 700

Ile Gly Leu Thr Thr Leu Pro Pro Val His Val Ile Lys Ala Ala Leu
705                 710                 715                 720

Leu Asn Phe Asp Glu Phe Ala Val Ser Lys Asp Gly Ile Glu Lys Leu
                725                 730                 735

Leu Thr Met Met Pro Thr Glu Glu Arg Gln Lys Ile Glu Glu Ala
            740                 745                 750

Gln Leu Ala Asn Pro Asp Ile Pro Leu Gly Pro Ala Glu Asn Phe Leu
        755                 760                 765

Met Thr Leu Ala Ser Ile Gly Gly Leu Ala Ala Arg Leu Gln Leu Trp
    770                 775                 780

Ala Phe Lys Leu Asp Tyr Asp Ser Met Glu Arg Glu Ile Ala Glu Pro
785                 790                 795                 800

Leu Phe Asp Leu Lys Val Gly Met Glu Gln Leu Val Gln Asn Ala Thr
                805                 810                 815

Phe Arg Cys Ile Leu Ala Thr Leu Leu Ala Val Gly Asn Phe Leu Asn
            820                 825                 830

Gly Ser Gln Ser Ser Gly Phe Glu Leu Ser Tyr Leu Glu Lys Val Ser
        835                 840                 845

Glu Val Lys Asp Thr Val Arg Arg Gln Ser Leu Leu His His Leu Cys
    850                 855                 860

Ser Leu Val Leu Gln Thr Arg Pro Glu Ser Ser Asp Leu Tyr Ser Glu
865                 870                 875                 880

Ile Pro Ala Leu Thr Arg Cys Ala Lys Val Asp Phe Glu Gln Leu Thr
                885                 890                 895

Glu Asn Leu Gly Gln Leu Glu Arg Arg Ser Arg Ala Ala Glu Glu Ser
            900                 905                 910

Leu Arg Ser Leu Ala Lys His Glu Leu Ala Pro Ala Leu Arg Ala Arg
        915                 920                 925

Leu Thr His Phe Leu Asp Gln Cys Ala Arg Arg Val Ala Met Leu Arg
    930                 935                 940

Ile Val His Arg Arg Val Cys Asn Arg Phe His Ala Phe Leu Leu Tyr
945                 950                 955                 960

Leu Gly Tyr Thr Pro Gln Ala Arg Glu Val Arg Ile Met Gln Phe
                965                 970                 975

Cys His Thr Leu Arg Glu Phe Ala Leu Glu Tyr Arg Thr Cys Arg Glu
            980                 985                 990

Arg Val Leu Gln Gln Gln Lys Gln Ala Thr Tyr Arg Glu Arg Asn
        995                 1000                1005

Lys Thr Arg Gly Arg Met Ile Thr Glu Thr Glu Lys Phe Ser Gly Val
    1010                1015                1020

Ala Gly Glu Ala Pro Ser Asn Pro Ser Val Pro Val Ala Val Ser Ser
1025                1030                1035                1040
```

-continued

```
Gly Pro Gly Arg Gly Asp Ala Asp Ser His Ala Ser Met Lys Ser Leu
            1045                1050                1055

Leu Thr Ser Arg Pro Glu Asp Thr Thr His Asn Arg Arg Ser Arg Gly
        1060                1065                1070

Met Val Gln Ser Ser Ser Pro Ile Met Pro Thr Val Gly Pro Ser Thr
    1075                1080                1085

Ala Ser Pro Glu Glu Pro Pro Gly Ser Ser Leu Pro Ser Asp Thr Ser
    1090                1095                1100

Asp Glu Ile Met Asp Leu Leu Val Gln Ser Val Thr Asn Ser Ser Pro
1105                1110                1115                1120

Arg Ala Leu Ala Ala Arg Glu Arg Lys Arg Ser Arg Gly Asn Arg Lys
                1125                1130                1135

Ser Leu Arg Arg Thr Leu Lys Ser Gly Leu Gly Asp Asp Leu Val Gln
            1140                1145                1150

Ala Leu Gly Leu Ser Lys Gly Pro Gly Leu Glu Val
            1155                1160

<210> SEQ ID NO 3
<211> LENGTH: 3853
<212> TYPE: DNA
<213> ORGANISM: Homo sapiens
<220> FEATURE:
<221> NAME/KEY: CDS
<222> LOCATION: (19)..(3588)

<400> SEQUENCE: 3
tgagccggcc gcagagcc atg gcg ggc ggg gaa gac cgc ggg gac gga gag       51
                   Met Ala Gly Gly Glu Asp Arg Gly Asp Gly Glu
                    1               5                   10 ccg gta tca gtg gtg acc gtg agg gtg cag tac ctg gaa gac acc gac       99
Pro Val Ser Val Val Thr Val Arg Val Gln Tyr Leu Glu Asp Thr Asp
         15                  20                  25 ccc ttc gca tgt gcc aac ttt ccg gag ccg cgc cgg gcc ccc acc tgc      147
Pro Phe Ala Cys Ala Asn Phe Pro Glu Pro Arg Arg Ala Pro Thr Cys
     30                  35                  40 agc ctg gac ggg gcg ctg ccc ttg ggc gcg cag ata ccc gcg gtg cac      195
Ser Leu Asp Gly Ala Leu Pro Leu Gly Ala Gln Ile Pro Ala Val His
 45                  50                  55 cgc ctg ctg gga gcg ccg ctc aag ttg gag gat tgt gct ctg caa gtg      243
Arg Leu Leu Gly Ala Pro Leu Lys Leu Glu Asp Cys Ala Leu Gln Val
 60                  65                  70                  75 tct ccc tcc gga tac tac ctg gac acc gag ctg tcc ctg gaa gag cag      291
Ser Pro Ser Gly Tyr Tyr Leu Asp Thr Glu Leu Ser Leu Glu Glu Gln
             80                  85                  90 cgg gag atg ctg gag ggc ttc tat gaa gag atc agc aaa ggg cgg aag      339
Arg Glu Met Leu Glu Gly Phe Tyr Glu Glu Ile Ser Lys Gly Arg Lys
         95                 100                 105 ccc acg ctg atc ctt cgg acc cag ctc tct gtg agg gtc aac gct atc      387
Pro Thr Leu Ile Leu Arg Thr Gln Leu Ser Val Arg Val Asn Ala Ile
     110                 115                 120 ttg gaa aag ctg tat agc tcc agt ggt cct gag ctc cgc cgc tcc ctc      435
Leu Glu Lys Leu Tyr Ser Ser Ser Gly Pro Glu Leu Arg Arg Ser Leu
 125                 130                 135 ttc tca ctg aag cag atc ttc cag gag gac aaa gac ctg gtg cct gaa      483
Phe Ser Leu Lys Gln Ile Phe Gln Glu Asp Lys Asp Leu Val Pro Glu
140                 145                 150                 155 ttt gtg cat tca gag ggg ctg agc tgc ctg atc cgt gtg ggt gct gct      531
Phe Val His Ser Glu Gly Leu Ser Cys Leu Ile Arg Val Gly Ala Ala
             160                 165                 170
```

-continued

```
gcc gac cac aac tac cag agc tac atc ctt aga gcg ctc ggc cag ctg        579
Ala Asp His Asn Tyr Gln Ser Tyr Ile Leu Arg Ala Leu Gly Gln Leu
            175                 180                 185 atg ctc ttt gtg gat gga atg ctg ggg gtg gtg gcc cac agt gac act        627
Met Leu Phe Val Asp Gly Met Leu Gly Val Val Ala His Ser Asp Thr
            190                 195                 200 att cag tgg ctg tac aca ttg tgt gcc agc ctg tcc cgc ttg gtg gtg        675
Ile Gln Trp Leu Tyr Thr Leu Cys Ala Ser Leu Ser Arg Leu Val Val
            205                 210                 215 aag aca gcc ctg aag ctg ctg ttg gtg ttt gta gaa tac tcc gaa aac        723
Lys Thr Ala Leu Lys Leu Leu Leu Val Phe Val Glu Tyr Ser Glu Asn
220                 225                 230                 235 aac gca ccg ctg ttc atc cgt gca gtg aac tct gtg gcc agc acc acc        771
Asn Ala Pro Leu Phe Ile Arg Ala Val Asn Ser Val Ala Ser Thr Thr
                240                 245                 250 ggt gct cct ccc tgg gcc aat ctg gtg tcc atc ctg gag gag aag aat        819
Gly Ala Pro Pro Trp Ala Asn Leu Val Ser Ile Leu Glu Glu Lys Asn
                255                 260                 265 ggc gct gac cct gag ttg ttg gtg tac acg gtc acc ctc atc aac aag        867
Gly Ala Asp Pro Glu Leu Leu Val Tyr Thr Val Thr Leu Ile Asn Lys
                270                 275                 280 acg ctg gcg gcg ctc ccg gac cag gac tcc ttc tac gat gtg acg gat        915
Thr Leu Ala Ala Leu Pro Asp Gln Asp Ser Phe Tyr Asp Val Thr Asp
285                 290                 295 gca ctg gag cag cag ggc atg gaa gcg ctg gtc cag cgc cac ctg ggc        963
Ala Leu Glu Gln Gln Gly Met Glu Ala Leu Val Gln Arg His Leu Gly
300                 305                 310                 315 act gcg ggc act gac gtc gac ctg cgc acg cag ctt gtg ctc tac gag       1011
Thr Ala Gly Thr Asp Val Asp Leu Arg Thr Gln Leu Val Leu Tyr Glu
                320                 325                 330 aac gcc ctg aaa ttg gag gat gga gac atc gaa gaa gcc cca ggc gct       1059
Asn Ala Leu Lys Leu Glu Asp Gly Asp Ile Glu Glu Ala Pro Gly Ala
                335                 340                 345 ggt ggg cgg cgg gaa cga cga aag cct tct tct gag gag ggc aag agg       1107
Gly Gly Arg Arg Glu Arg Arg Lys Pro Ser Ser Glu Glu Gly Lys Arg
                350                 355                 360 agc cgc cgt tct ctg gaa ggg ggc tgc ccc gcg cgt gcc ccg gaa           1155
Ser Arg Arg Ser Leu Glu Gly Gly Cys Pro Ala Arg Ala Pro Glu
365                 370                 375 cct ggc ccc aca ggc ccc gcc tca ccg gta ggc ccc acc tct tcc acc       1203
Pro Gly Pro Thr Gly Pro Ala Ser Pro Val Gly Pro Thr Ser Ser Thr
380                 385                 390                 395 ggc ccc gcc ctg ctg aca ggc ccc gcc tcc agc cct gtg ggc cct ccc       1251
Gly Pro Ala Leu Leu Thr Gly Pro Ala Ser Ser Pro Val Gly Pro Pro
                400                 405                 410 tcc ggt ctc caa gct tca gtg aac ctt ttt cct acc atc tct gtg gca       1299
Ser Gly Leu Gln Ala Ser Val Asn Leu Phe Pro Thr Ile Ser Val Ala
                415                 420                 425 ccc tca gct gac acc tcc agc gag agg agc atc tac aaa ctt cac caa       1347
Pro Ser Ala Asp Thr Ser Ser Glu Arg Ser Ile Tyr Lys Leu His Gln
                430                 435                 440 act gct tcc gtt tgg gcc cct gag agc cca ccc gtc ccc cag tcc cct       1395
Thr Ala Ser Val Trp Ala Pro Glu Ser Pro Pro Val Pro Gln Ser Pro
445                 450                 455 cct ggg cag gcc agg ctg gaa gcc cgg ttc ctg gag aat gtg gcg gca       1443
Pro Gly Gln Ala Arg Leu Glu Ala Arg Phe Leu Glu Asn Val Ala Ala
460                 465                 470                 475
```

```
gca gaa aca gag aag cag gtt gcg ctg gcc cag ggc cgg gca gag aca    1491
Ala Glu Thr Glu Lys Gln Val Ala Leu Ala Gln Gly Arg Ala Glu Thr
            480                 485                 490 ctt gcc ggg gcc atg ccc aat gag gcg ggt gga cac cca gat gcc cgg    1539
Leu Ala Gly Ala Met Pro Asn Glu Ala Gly Gly His Pro Asp Ala Arg
            495                 500                 505 caa ctc tgg gac tcc cca gag aca gcc cct gca gcc aga aca ccc cag    1587
Gln Leu Trp Asp Ser Pro Glu Thr Ala Pro Ala Ala Arg Thr Pro Gln
            510                 515                 520 agc cct gcc ccc tgt gtc ctg ctc cgg gcc cag cga agc ctt gca cca    1635
Ser Pro Ala Pro Cys Val Leu Leu Arg Ala Gln Arg Ser Leu Ala Pro
        525                 530                 535 gag ccc aag gag cca ctg ata cca gca agc ccc aag gct gag ccc atc    1683
Glu Pro Lys Glu Pro Leu Ile Pro Ala Ser Pro Lys Ala Glu Pro Ile
540                 545                 550                 555 tgg gag ctc cct acc cgt gca ccc agg ctc tct att ggg gac ctg gac    1731
Trp Glu Leu Pro Thr Arg Ala Pro Arg Leu Ser Ile Gly Asp Leu Asp
                560                 565                 570 ttt tca gat cta ggg gag gat gaa gac cag gac atg ctg aat gta gag    1779
Phe Ser Asp Leu Gly Glu Asp Glu Asp Gln Asp Met Leu Asn Val Glu
            575                 580                 585 tct gtg gag gct ggg aaa gac atc cca gct ccc tca ccc cca ctg ccc    1827
Ser Val Glu Ala Gly Lys Asp Ile Pro Ala Pro Ser Pro Pro Leu Pro
            590                 595                 600 ctg ctc tcg gga gta ccc ccc cct ccc cca ctt cca cct ccc cca ccc    1875
Leu Leu Ser Gly Val Pro Pro Pro Pro Pro Leu Pro Pro Pro Pro Pro
            605                 610                 615 atc aaa ggc ccc ttc cca cca cct cca cct cta cct ctg gct gcc cct    1923
Ile Lys Gly Pro Phe Pro Pro Pro Pro Leu Pro Leu Ala Ala Pro
620                 625                 630                 635 ctt ccc cat tca gtg cct gac agc tca gcc ctc ccc act aag agg aag    1971
Leu Pro His Ser Val Pro Asp Ser Ser Ala Leu Pro Thr Lys Arg Lys
                640                 645                 650 aca gta aaa ctt ttc tgg cgt gag ctg aag ctg gct ggg ggc cat gga    2019
Thr Val Lys Leu Phe Trp Arg Glu Leu Lys Leu Ala Gly Gly His Gly
            655                 660                 665 gtc tct gca agc cgc ttt ggg ccc tgc gcc acc ctc tgg gct tca ctg    2067
Val Ser Ala Ser Arg Phe Gly Pro Cys Ala Thr Leu Trp Ala Ser Leu
            670                 675                 680 gac cct gtc tca gtg gac acg gcc cga ctg gaa cac ctc ttt gag tct    2115
Asp Pro Val Ser Val Asp Thr Ala Arg Leu Glu His Leu Phe Glu Ser
685                 690                 695 cgt gcc aaa gag gtg ctg ccc tcc aag aaa gct gga gag ggc cgc cgg    2163
Arg Ala Lys Glu Val Leu Pro Ser Lys Lys Ala Gly Glu Gly Arg Arg
700                 705                 710                 715 aca atg acc aca gtg ctg gac ccc aag cgc agc aac gcc atc aac atc    2211
Thr Met Thr Thr Val Leu Asp Pro Lys Arg Ser Asn Ala Ile Asn Ile
                720                 725                 730 ggc cta acc aca ctg cca cct gtg cat gtc att aag gct gct ctg ctc    2259
Gly Leu Thr Thr Leu Pro Pro Val His Val Ile Lys Ala Ala Leu Leu
            735                 740                 745 aac ttt gat gag ttt gct gtc agc aag gat ggc att gag aag cta ctg    2307
Asn Phe Asp Glu Phe Ala Val Ser Lys Asp Gly Ile Glu Lys Leu Leu
            750                 755                 760 acc atg atg ccc acg gag gaa gag cgg cag aag att gag gaa gcc cag    2355
Thr Met Met Pro Thr Glu Glu Glu Arg Gln Lys Ile Glu Glu Ala Gln
765                 770                 775
```

```
ctg gcc aac cct gac ata ccc ctg ggc cca gcc gag aac ttc ctg atg    2403
Leu Ala Asn Pro Asp Ile Pro Leu Gly Pro Ala Glu Asn Phe Leu Met
780                 785                 790                 795 act ctt gcc tcc att ggc ggc ctc gct gct cgt cta caa ctc tgg gcc    2451
Thr Leu Ala Ser Ile Gly Gly Leu Ala Ala Arg Leu Gln Leu Trp Ala
                800                 805                 810 ttc aag ctg gac tat gac agc atg gag cgg gaa att gct gag cca ctg    2499
Phe Lys Leu Asp Tyr Asp Ser Met Glu Arg Glu Ile Ala Glu Pro Leu
        815                 820                 825 ttt gac ctg aaa gtg ggt atg gaa cag ctg gta cag aat gcc acc ttc    2547
Phe Asp Leu Lys Val Gly Met Glu Gln Leu Val Gln Asn Ala Thr Phe
    830                 835                 840 cgc tgc atc ctg gct acc ctc cta gcg gtg ggc aac ttc ctc aat ggc    2595
Arg Cys Ile Leu Ala Thr Leu Leu Ala Val Gly Asn Phe Leu Asn Gly
845                 850                 855 tcc cag agc agc ggc ttt gag ctg agc tac ctg gag aag gtg tca gag    2643
Ser Gln Ser Ser Gly Phe Glu Leu Ser Tyr Leu Glu Lys Val Ser Glu
860                 865                 870                 875 gtg aag gac acg gtg cgt cga cag tca ctg cta cac cat ctc tgc tcc    2691
Val Lys Asp Thr Val Arg Arg Gln Ser Leu Leu His His Leu Cys Ser
                880                 885                 890 cta gtg ctc cag acc cgg cct gag tcc tct gac ctc tat tca gaa atc    2739
Leu Val Leu Gln Thr Arg Pro Glu Ser Ser Asp Leu Tyr Ser Glu Ile
        895                 900                 905 cct gcc ctg acc cgc tgt gcc aag gtg gac ttt gaa cag ctg act gag    2787
Pro Ala Leu Thr Arg Cys Ala Lys Val Asp Phe Glu Gln Leu Thr Glu
    910                 915                 920 aac ctg ggg cag ctg gag cgc cgg agc cgg gca gcc gag gag agc ctg    2835
Asn Leu Gly Gln Leu Glu Arg Arg Ser Arg Ala Ala Glu Glu Ser Leu
925                 930                 935 cgg agc ttg gcc aag cat gag ctg gcc cca gcc ctg cgt gcc cgc ctc    2883
Arg Ser Leu Ala Lys His Glu Leu Ala Pro Ala Leu Arg Ala Arg Leu
940                 945                 950                 955 acc cac ttc ctg gac cag tgt gcc cgc cgt gtt gcc atg cta agg ata    2931
Thr His Phe Leu Asp Gln Cys Ala Arg Arg Val Ala Met Leu Arg Ile
                960                 965                 970 gtg cac cgc cgt gtc tgc aat agg ttc cat gcc ttc ctg ctc tac ctg    2979
Val His Arg Arg Val Cys Asn Arg Phe His Ala Phe Leu Leu Tyr Leu
        975                 980                 985 ggc tac acc ccg cag gcg gcc cgt gaa gtg cgc atc atg cag ttc tgc    3027
Gly Tyr Thr Pro Gln Ala Ala Arg Glu Val Arg Ile Met Gln Phe Cys
    990                 995                 1000 cac acg ctg cgg gaa ttt gcg ctt gag tat cgg act tgc cgg gaa cga    3075
His Thr Leu Arg Glu Phe Ala Leu Glu Tyr Arg Thr Cys Arg Glu Arg
    1005                1010                1015 gtg cta cag cag cag cag aag cag gcc aca tac cgt gag cgc aac aag    3123
Val Leu Gln Gln Gln Gln Lys Gln Ala Thr Tyr Arg Glu Arg Asn Lys
1020                1025                1030                1035 acc cgg gga cgc atg atc acc gag aca gag aag ttc tca ggt gtg gct    3171
Thr Arg Gly Arg Met Ile Thr Glu Thr Glu Lys Phe Ser Gly Val Ala
                1040                1045                1050 ggg gaa gcc ccc agc aac ccc tct gtc cca gta gca gtg agc agc ggg    3219
Gly Glu Ala Pro Ser Asn Pro Ser Val Pro Val Ala Val Ser Ser Gly
        1055                1060                1065 cca ggc cgg gga gat gct gac agt cat gct agt atg aag agt ctg ctg    3267
Pro Gly Arg Gly Asp Ala Asp Ser His Ala Ser Met Lys Ser Leu Leu
    1070                1075                1080
```

-continued

```
acc agc agg cct gag gac acc aca cac aat cgc cgc agc aga ggc atg     3315
Thr Ser Arg Pro Glu Asp Thr Thr His Asn Arg Arg Ser Arg Gly Met
    1085                1090                1095 gtc cag agc agc tcc cca atc atg ccc aca gtg ggg ccc tcc act gca     3363
Val Gln Ser Ser Ser Pro Ile Met Pro Thr Val Gly Pro Ser Thr Ala
1100                1105                1110                1115 tcc cca gaa gaa ccc cca ggc tcc agt tta ccc agt gat aca tca gat     3411
Ser Pro Glu Glu Pro Pro Gly Ser Ser Leu Pro Ser Asp Thr Ser Asp
                1120                1125                1130 gag atc atg gac ctt ctg gtg cag tca gtg acc aag agc agt cct cgt     3459
Glu Ile Met Asp Leu Leu Val Gln Ser Val Thr Lys Ser Ser Pro Arg
            1135                1140                1145 gcc tta gct gct agg gaa cgc aag cgt tcc cgc ggc aac cgc aag tct     3507
Ala Leu Ala Ala Arg Glu Arg Lys Arg Ser Arg Gly Asn Arg Lys Ser
        1150                1155                1160 ttg aga agg acg ttg aag agt ggg ctc gga gat gac ctg gtg cag gca     3555
Leu Arg Arg Thr Leu Lys Ser Gly Leu Gly Asp Asp Leu Val Gln Ala
    1165                1170                1175 ctg gga cta agc aag ggt cct ggc ctg gag gtg tgaaggtgct gtatcccgga   3608
Leu Gly Leu Ser Lys Gly Pro Gly Leu Glu Val
1180                1185                1190 aatctatctg gaccctggac tgcagtgcag gagatgacag agtgaggagg gcccagagca   3668
gaattctggc cccagaactc tgtgcccagg agccatgcct tgagcagtat tagccgtgtg   3728
tgtatgcatg tgagtgtgtg tgtatgtgtg tgtgtgcatg catatgcatg tgcatgtgtg   3788
tgagctcctt gaacgcacgg agcaaaataa aattttctta gctaatccaa aaaaaaaaaa   3848
aaaaa                                                               3853

<210> SEQ ID NO 4
<211> LENGTH: 3775
<212> TYPE: DNA
<213> ORGANISM: Homo sapiens
<220> FEATURE:
<221> NAME/KEY: CDS
<222> LOCATION: (19)..(3510)

<400> SEQUENCE: 4
tgagccggcc gcagagcc atg gcg ggc ggg gaa gac cgc ggg gac gga gag      51
                    Met Ala Gly Gly Glu Asp Arg Gly Asp Gly Glu
                      1               5                  10 ccg gta tca gtg gtg acc gtg agg gtg cag tac ctg gaa gac acc gac      99
Pro Val Ser Val Val Thr Val Arg Val Gln Tyr Leu Glu Asp Thr Asp
            15                  20                  25 ccc ttc gca tgt gcc aac ttt ccg gag ccg cgc cgg gcc ccc acc tgc     147
Pro Phe Ala Cys Ala Asn Phe Pro Glu Pro Arg Arg Ala Pro Thr Cys
        30                  35                  40 agc ctg gac ggg gcg ctg ccc ttg ggc gcg cag ata ccc gcg gtg cac     195
Ser Leu Asp Gly Ala Leu Pro Leu Gly Ala Gln Ile Pro Ala Val His
    45                  50                  55 cgc ctg ctg gga gcg ccg ctc aag ttg gag gat tgt gct ctg caa gtg     243
Arg Leu Leu Gly Ala Pro Leu Lys Leu Glu Asp Cys Ala Leu Gln Val
60                  65                  70                  75 tct ccc tcc gga tac tac ctg gac acc gag ctg tcc ctg gaa gag cag     291
Ser Pro Ser Gly Tyr Tyr Leu Asp Thr Glu Leu Ser Leu Glu Glu Gln
                80                  85                  90 cgg gag atg ctg gag ggc ttc tat gaa gag atc agc aaa ggg cgg aag     339
Arg Glu Met Leu Glu Gly Phe Tyr Glu Glu Ile Ser Lys Gly Arg Lys
            95                  100                 105
```

-continued

| | | |
|---|---|---|
| ccc acg ctg atc ctt cgg acc cag ctc tct gtg agg gtc aac gct atc<br>Pro Thr Leu Ile Leu Arg Thr Gln Leu Ser Val Arg Val Asn Ala Ile<br>    110             115                 120 | | 387 |
| ttg gaa aag ctg tat agc tcc agt ggt cct gag ctc cgc cgc tcc ctc<br>Leu Glu Lys Leu Tyr Ser Ser Ser Gly Pro Glu Leu Arg Arg Ser Leu<br>125             130                 135 | | 435 |
| ttc tca ctg aag cag atc ttc cag gag gac aaa gac ctg gtg cct gaa<br>Phe Ser Leu Lys Gln Ile Phe Gln Glu Asp Lys Asp Leu Val Pro Glu<br>140             145                 150             155 | | 483 |
| ttt gtg cat tca gag ggg ctg agc tgc ctg atc cgt gtg ggt gct gct<br>Phe Val His Ser Glu Gly Leu Ser Cys Leu Ile Arg Val Gly Ala Ala<br>                160             165                 170 | | 531 |
| gcc gac cac aac tac cag agc tac atc ctt aga gcg ctc ggc cag ctg<br>Ala Asp His Asn Tyr Gln Ser Tyr Ile Leu Arg Ala Leu Gly Gln Leu<br>            175             180             185 | | 579 |
| atg ctc ttt gtg gat gga atg ctg ggg gtg gtg gcc cac agt gac act<br>Met Leu Phe Val Asp Gly Met Leu Gly Val Val Ala His Ser Asp Thr<br>        190             195             200 | | 627 |
| att cag tgg ctg tac aca ttg tgt gcc agc ctg tcc cgc ttg gtg gtg<br>Ile Gln Trp Leu Tyr Thr Leu Cys Ala Ser Leu Ser Arg Leu Val Val<br>    205             210             215 | | 675 |
| aag aca gcc ctg aag ctg ctg ttg gtg ttt gta gaa tac tcc gaa aac<br>Lys Thr Ala Leu Lys Leu Leu Val Phe Val Glu Tyr Ser Glu Asn<br>220             225             230             235 | | 723 |
| aac gca ccg ctg ttc atc cgt gca gtg aac tct gtg gcc agc acc acc<br>Asn Ala Pro Leu Phe Ile Arg Ala Val Asn Ser Val Ala Ser Thr Thr<br>                240             245             250 | | 771 |
| ggt gct cct ccc tgg gcc aat ctg gtg tcc atc ctg gag gag aag aat<br>Gly Ala Pro Pro Trp Ala Asn Leu Val Ser Ile Leu Glu Glu Lys Asn<br>            255             260             265 | | 819 |
| ggc gct gac cct gag ttg ttg gtg tac acg gtc acc ctc atc aac aag<br>Gly Ala Asp Pro Glu Leu Leu Val Tyr Thr Val Thr Leu Ile Asn Lys<br>        270             275             280 | | 867 |
| acg ctg gcg gcg ctc ccg gac cag gac tcc ttc tac gat gtg acg gat<br>Thr Leu Ala Ala Leu Pro Asp Gln Asp Ser Phe Tyr Asp Val Thr Asp<br>    285             290             295 | | 915 |
| gca ctg gag cag cag ggc atg gaa gcg ctg gtc cag cgc cac ctg ggc<br>Ala Leu Glu Gln Gln Gly Met Glu Ala Leu Val Gln Arg His Leu Gly<br>300             305             310             315 | | 963 |
| act gcg ggc act gac gtc gac ctg cgc acg cag ctt gtg ctc tac gag<br>Thr Ala Gly Thr Asp Val Asp Leu Arg Thr Gln Leu Val Leu Tyr Glu<br>                320             325             330 | | 1011 |
| aac gcc ctg aaa ttg gag gat gga gac atc gaa gaa gcc cca ggc gct<br>Asn Ala Leu Lys Leu Glu Asp Gly Asp Ile Glu Glu Ala Pro Gly Ala<br>            335             340             345 | | 1059 |
| ggt ggg cgg cgg gaa cga cga aag cct tct tct gag gag ggc aag agg<br>Gly Gly Arg Arg Glu Arg Arg Lys Pro Ser Ser Glu Glu Gly Lys Arg<br>        350             355             360 | | 1107 |
| agc cgc cgt tct ctg gaa ggg ggc tgc ccc gcg cgt gcc ccg gaa<br>Ser Arg Arg Ser Leu Glu Gly Gly Cys Pro Ala Arg Ala Pro Glu<br>    365             370             375 | | 1155 |
| cct ggc ccc aca ggc ccc gcc tca ccg gta ggc ccc acc tct tcc acc<br>Pro Gly Pro Thr Gly Pro Ala Ser Pro Val Gly Pro Thr Ser Ser Thr<br>380             385             390             395 | | 1203 |
| ggc ccc gcc ctg ctg aca ggc ccc gcc tcc agc cct gtg ggc cct ccc<br>Gly Pro Ala Leu Leu Thr Gly Pro Ala Ser Ser Pro Val Gly Pro Pro<br>                400             405             410 | | 1251 |

-continued

| | |
|---|---|
| tcc ggt ctc caa gct tca gtg aac ctt ttt cct acc atc tct gtg gca<br>Ser Gly Leu Gln Ala Ser Val Asn Leu Phe Pro Thr Ile Ser Val Ala<br>                415                        420                      425 | 1299 |
| ccc tca gct gac acc tcc agc gag agg agc atc tac aaa gcc cgg ttc<br>Pro Ser Ala Asp Thr Ser Ser Glu Arg Ser Ile Tyr Lys Ala Arg Phe<br>                430                        435                      440 | 1347 |
| ctg gag aat gtg gcg gca gca gaa aca gag aag cag gtt gcg ctg gcc<br>Leu Glu Asn Val Ala Ala Ala Glu Thr Glu Lys Gln Val Ala Leu Ala<br>445                        450                        455 | 1395 |
| cag ggc cgg gca gag aca ctt gcc ggg gcc atg ccc aat gag gcg ggt<br>Gln Gly Arg Ala Glu Thr Leu Ala Gly Ala Met Pro Asn Glu Ala Gly<br>460                        465                        470                      475 | 1443 |
| gga cac cca gat gcc cgg caa ctc tgg gac tcc cca gag aca gcc cct<br>Gly His Pro Asp Ala Arg Gln Leu Trp Asp Ser Pro Glu Thr Ala Pro<br>                480                        485                      490 | 1491 |
| gca gcc aga aca ccc cag agc cct gcc ccc tgt gtc ctg ctc cgg gcc<br>Ala Ala Arg Thr Pro Gln Ser Pro Ala Pro Cys Val Leu Leu Arg Ala<br>                        495                        500                      505 | 1539 |
| cag cga agc ctt gca cca gag ccc aag gag cca ctg ata cca gca agc<br>Gln Arg Ser Leu Ala Pro Glu Pro Lys Glu Pro Leu Ile Pro Ala Ser<br>        510                        515                        520 | 1587 |
| ccc aag gct gag ccc atc tgg gag ctc cct acc cgt gca ccc agg ctc<br>Pro Lys Ala Glu Pro Ile Trp Glu Leu Pro Thr Arg Ala Pro Arg Leu<br>525                        530                        535 | 1635 |
| tct att ggg gac ctg gac ttt tca gat cta ggg gag gat gaa gac cag<br>Ser Ile Gly Asp Leu Asp Phe Ser Asp Leu Gly Glu Asp Glu Asp Gln<br>540                        545                        550                      555 | 1683 |
| gac atg ctg aat gta gag tct gtg gag gct ggg aaa gac atc cca gct<br>Asp Met Leu Asn Val Glu Ser Val Glu Ala Gly Lys Asp Ile Pro Ala<br>                560                        565                      570 | 1731 |
| ccc tca ccc cca ctg ccc ctg ctc tcg gga gta ccc ccc cct ccc cca<br>Pro Ser Pro Pro Leu Pro Leu Leu Ser Gly Val Pro Pro Pro Pro Pro<br>                        575                        580                      585 | 1779 |
| ctt cca cct ccc cca ccc atc aaa ggc ccc ttc cca cca cct cca cct<br>Leu Pro Pro Pro Pro Pro Ile Lys Gly Pro Phe Pro Pro Pro Pro Pro<br>        590                        595                        600 | 1827 |
| cta cct ctg gct gcc cct ctt ccc cat tca gtg cct gac agc tca gcc<br>Leu Pro Leu Ala Ala Pro Leu Pro His Ser Val Pro Asp Ser Ser Ala<br>605                        610                        615 | 1875 |
| ctc ccc act aag agg aag aca gta aaa ctt ttc tgg cgt gag ctg aag<br>Leu Pro Thr Lys Arg Lys Thr Val Lys Leu Phe Trp Arg Glu Leu Lys<br>620                        625                        630                      635 | 1923 |
| ctg gct ggg ggc cat gga gtc tct gca agc cgc ttt ggg ccc tgc gcc<br>Leu Ala Gly Gly His Gly Val Ser Ala Ser Arg Phe Gly Pro Cys Ala<br>                640                        645                      650 | 1971 |
| acc ctc tgg gct tca ctg gac cct gtc tca gtg gac acg gcc cga ctg<br>Thr Leu Trp Ala Ser Leu Asp Pro Val Ser Val Asp Thr Ala Arg Leu<br>                        655                        660                      665 | 2019 |
| gaa cac ctc ttt gag tct cgt gcc aaa gag gtg ctg ccc tcc aag aaa<br>Glu His Leu Phe Glu Ser Arg Ala Lys Glu Val Leu Pro Ser Lys Lys<br>        670                        675                        680 | 2067 |
| gct gga gag ggc cgc cgg aca atg acc aca gtg ctg gac ccc aag cgc<br>Ala Gly Glu Gly Arg Arg Thr Met Thr Thr Val Leu Asp Pro Lys Arg<br>685                        690                        695 | 2115 |
| agc aac gcc atc aac atc ggc cta acc aca ctg cca cct gtg cat gtc<br>Ser Asn Ala Ile Asn Ile Gly Leu Thr Thr Leu Pro Pro Val His Val<br>700                        705                        710                      715 | 2163 |

```
att aag gct gct ctg ctc aac ttt gat gag ttt gct gtc agc aag gat     2211
Ile Lys Ala Ala Leu Leu Asn Phe Asp Glu Phe Ala Val Ser Lys Asp
            720                 725                 730 ggc att gag aag cta ctg acc atg atg ccc acg gag gaa gag cgg cag     2259
Gly Ile Glu Lys Leu Leu Thr Met Met Pro Thr Glu Glu Glu Arg Gln
        735                 740                 745 aag att gag gaa gcc cag ctg gcc aac cct gac ata ccc ctg ggc cca     2307
Lys Ile Glu Glu Ala Gln Leu Ala Asn Pro Asp Ile Pro Leu Gly Pro
    750                 755                 760 gcc gag aac ttc ctg atg act ctt gcc tcc att ggc ggc ctc gct gct     2355
Ala Glu Asn Phe Leu Met Thr Leu Ala Ser Ile Gly Gly Leu Ala Ala
765                 770                 775 cgt cta caa ctc tgg gcc ttc aag ctg gac tat gac agc atg gag cgg     2403
Arg Leu Gln Leu Trp Ala Phe Lys Leu Asp Tyr Asp Ser Met Glu Arg
780                 785                 790                 795 gaa att gct gag cca ctg ttt gac ctg aaa gtg ggt atg gaa cag ctg     2451
Glu Ile Ala Glu Pro Leu Phe Asp Leu Lys Val Gly Met Glu Gln Leu
                800                 805                 810 gta cag aat gcc acc ttc cgc tgc atc ctg gct acc ctc cta gcg gtg     2499
Val Gln Asn Ala Thr Phe Arg Cys Ile Leu Ala Thr Leu Leu Ala Val
            815                 820                 825 ggc aac ttc ctc aat ggc tcc cag agc agc ggc ttt gag ctg agc tac     2547
Gly Asn Phe Leu Asn Gly Ser Gln Ser Ser Gly Phe Glu Leu Ser Tyr
        830                 835                 840 ctg gag aag gtg tca gag gtg aag gac acg gtg cgt cga cag tca ctg     2595
Leu Glu Lys Val Ser Glu Val Lys Asp Thr Val Arg Arg Gln Ser Leu
    845                 850                 855 cta cac cat ctc tgc tcc cta gtg ctc cag acc cgg cct gag tcc tct     2643
Leu His His Leu Cys Ser Leu Val Leu Gln Thr Arg Pro Glu Ser Ser
860                 865                 870                 875 gac ctc tat tca gaa atc cct gcc ctg acc cgc tgt gcc aag gtg gac     2691
Asp Leu Tyr Ser Glu Ile Pro Ala Leu Thr Arg Cys Ala Lys Val Asp
                880                 885                 890 ttt gaa cag ctg act gag aac ctg ggg cag ctg gag cgc cgg agc cgg     2739
Phe Glu Gln Leu Thr Glu Asn Leu Gly Gln Leu Glu Arg Arg Ser Arg
            895                 900                 905 gca gcc gag gag agc ctg cgg agc ttg gcc aag cat gag ctg gcc cca     2787
Ala Ala Glu Glu Ser Leu Arg Ser Leu Ala Lys His Glu Leu Ala Pro
        910                 915                 920 gcc ctg cgt gcc cgc ctc acc cac ttc ctg gac cag tgt gcc cgc cgt     2835
Ala Leu Arg Ala Arg Leu Thr His Phe Leu Asp Gln Cys Ala Arg Arg
    925                 930                 935 gtt gcc atg cta agg ata gtg cac cgc gtt gtc tgc aat agg ttc cat     2883
Val Ala Met Leu Arg Ile Val His Arg Val Val Cys Asn Arg Phe His
940                 945                 950                 955 gcc ttc ctg ctc tac ctg ggc tac acc ccg cag gcg gcc cgt gaa gtg     2931
Ala Phe Leu Leu Tyr Leu Gly Tyr Thr Pro Gln Ala Ala Arg Glu Val
                960                 965                 970 cgc atc atg cag ttc tgc cac acg ctg cgg gaa ttt gcg ctt gag tat     2979
Arg Ile Met Gln Phe Cys His Thr Leu Arg Glu Phe Ala Leu Glu Tyr
            975                 980                 985 cgg act tgc cgg gaa cga gtg cta cag cag cag cag aag cag gcc aca     3027
Arg Thr Cys Arg Glu Arg Val Leu Gln Gln Gln Gln Lys Gln Ala Thr
        990                 995                 1000 tac cgt gag cgc aac aag acc cgg gga cgc atg atc acc gag aca gag     3075
Tyr Arg Glu Arg Asn Lys Thr Arg Gly Arg Met Ile Thr Glu Thr Glu
    1005                1010                1015
```

|  |  |
|---|---|
| aag ttc tca ggt gtg gct ggg gaa gcc ccc agc aac ccc tct gtc cca<br>Lys Phe Ser Gly Val Ala Gly Glu Ala Pro Ser Asn Pro Ser Val Pro<br>1020                   1025               1030               1035 | 3123 |
| gta gca gtg agc agc ggg cca ggc cgg gga gat gct gac agt cat gct<br>Val Ala Val Ser Ser Gly Pro Gly Arg Gly Asp Ala Asp Ser His Ala<br>            1040               1045               1050 | 3171 |
| agt atg aag agt ctg ctg acc agc agg cct gag gac acc aca cac aat<br>Ser Met Lys Ser Leu Leu Thr Ser Arg Pro Glu Asp Thr Thr His Asn<br>1055                   1060               1065 | 3219 |
| cgc cgc agc aga ggc atg gtc cag agc agc tcc cca atc atg ccc aca<br>Arg Arg Ser Arg Gly Met Val Gln Ser Ser Ser Pro Ile Met Pro Thr<br>            1070               1075               1080 | 3267 |
| gtg ggg ccc tcc act gca tcc cca gaa gaa ccc cca ggc tcc agt tta<br>Val Gly Pro Ser Thr Ala Ser Pro Glu Glu Pro Pro Gly Ser Ser Leu<br>1085                   1090               1095 | 3315 |
| ccc agt gat aca tca gat gag atc atg gac ctt ctg gtg cag tca gtg<br>Pro Ser Asp Thr Ser Asp Glu Ile Met Asp Leu Leu Val Gln Ser Val<br>1100                   1105               1110               1115 | 3363 |
| acc aac agc agt cct cgt gcc tta gct gct agg gaa cgc aag cgt tcc<br>Thr Asn Ser Ser Pro Arg Ala Leu Ala Ala Arg Glu Arg Lys Arg Ser<br>            1120               1125               1130 | 3411 |
| cgc ggc aac cgc aag tct ttg aga agg acg ttg aag agt ggg ctc gga<br>Arg Gly Asn Arg Lys Ser Leu Arg Arg Thr Leu Lys Ser Gly Leu Gly<br>1135                   1140               1145 | 3459 |
| gat gac ctg gtg cag gca ctg gga cta agc aag ggt cct ggc ctg gag<br>Asp Asp Leu Val Gln Ala Leu Gly Leu Ser Lys Gly Pro Gly Leu Glu<br>1150                   1155               1160 | 3507 |
| gtg tgaaggtgct gtatcccgga aatctatctg daccctggac tgcagtgcag<br>Val | 3560 |
| gagatgacag agtgaggagg gcccagagca gaattctggc cccagaactc tgtgcccagg | 3620 |
| agccatgcct tgagcagtat tagccgtgtg tgtatgcatg tgagtgtgtg tgtatgtgtg | 3680 |
| tgtgtgcatg catatgcatg tgcatgtgtg tgagctcctt gaacgcacgg agcaaaataa | 3740 |
| aattttctta gctaatccaa aaaaaaaaaa aaaaa | 3775 |

<210> SEQ ID NO 5
<211> LENGTH: 447
<212> TYPE: PRT
<213> ORGANISM: Homo sapiens

<400> SEQUENCE: 5

Met Ala Gly Gly Glu Asp Arg Gly Asp Gly Glu Pro Val Ser Val Val
1               5                  10                15

Thr Val Arg Val Gln Tyr Leu Glu Asp Thr Asp Pro Phe Ala Cys Ala
                20                  25                30

Asn Phe Pro Glu Pro Arg Arg Ala Pro Thr Cys Ser Leu Asp Gly Ala
          35                  40                45

Leu Pro Leu Gly Ala Gln Ile Pro Ala Val His Arg Leu Leu Gly Ala
50                  55                  60

Pro Leu Lys Leu Glu Asp Cys Ala Leu Gln Val Ser Pro Ser Gly Tyr
65               70                  75                80

Tyr Leu Asp Thr Glu Leu Ser Leu Glu Glu Gln Arg Glu Met Leu Glu
                85                  90                95

Gly Phe Tyr Glu Glu Ile Ser Lys Gly Arg Lys Pro Thr Leu Ile Leu
               100              105              110

Arg Thr Gln Leu Ser Val Arg Val Asn Ala Ile Leu Glu Lys Leu Tyr
          115                120              125

```
Ser Ser Ser Gly Pro Glu Leu Arg Arg Ser Leu Phe Ser Leu Lys Gln
        130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Asp Thr Ile Gln Trp Leu Tyr
        195                 200                 205

Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Arg Ala Val Asn Ser Val Ala Ser Thr Thr Gly Ala Pro Pro Trp
                245                 250                 255

Ala Asn Leu Val Ser Ile Leu Glu Glu Lys Asn Gly Ala Asp Pro Glu
            260                 265                 270

Leu Leu Val Tyr Thr Val Thr Leu Ile Asn Lys Thr Leu Ala Ala Leu
        275                 280                 285

Pro Asp Gln Asp Ser Phe Tyr Asp Val Thr Asp Ala Leu Glu Gln Gln
    290                 295                 300

Gly Met Glu Ala Leu Val Gln Arg His Leu Gly Thr Ala Gly Thr Asp
305                 310                 315                 320

Val Asp Leu Arg Thr Gln Leu Val Leu Tyr Glu Asn Ala Leu Lys Leu
                325                 330                 335

Glu Asp Gly Asp Ile Glu Glu Ala Pro Gly Ala Gly Arg Arg Glu
            340                 345                 350

Arg Arg Lys Pro Ser Ser Glu Glu Gly Lys Arg Ser Arg Arg Ser Leu
        355                 360                 365

Glu Gly Gly Gly Cys Pro Ala Arg Ala Pro Glu Pro Gly Pro Thr Gly
    370                 375                 380

Pro Ala Ser Pro Val Gly Pro Thr Ser Ser Thr Gly Pro Ala Leu Leu
385                 390                 395                 400

Thr Gly Pro Ala Ser Ser Pro Val Gly Pro Pro Ser Gly Leu Gln Ala
                405                 410                 415

Ser Val Asn Leu Phe Pro Thr Ile Ser Val Ala Pro Ser Ala Asp Thr
            420                 425                 430

Ser Ser Glu Arg Ser Ile Tyr Lys Leu His Gln Thr Ala Ser Val
        435                 440                 445

<210> SEQ ID NO 6
<211> LENGTH: 3799
<212> TYPE: DNA
<213> ORGANISM: Homo sapiens
<220> FEATURE:
<221> NAME/KEY: CDS
<222> LOCATION: (19)..(1359)

<400> SEQUENCE: 6
tgagccggcc gcagagcc atg gcg ggc ggg gaa gac cgc ggg gac gga gag      51
                   Met Ala Gly Gly Glu Asp Arg Gly Asp Gly Glu
                     1               5                  10 ccg gta tca gtg gtg acc gtg agg gtg cag tac ctg gaa gac acc gac      99
Pro Val Ser Val Val Thr Val Arg Val Gln Tyr Leu Glu Asp Thr Asp
         15                  20                  25
```

```
ccc ttc gca tgt gcc aac ttt ccg gag ccg cgc cgg gcc ccc acc tgc    147
Pro Phe Ala Cys Ala Asn Phe Pro Glu Pro Arg Arg Ala Pro Thr Cys
         30                  35                  40 agc ctg gac ggg gcg ctg ccc ttg ggc gcg cag ata ccc gcg gtg cac    195
Ser Leu Asp Gly Ala Leu Pro Leu Gly Ala Gln Ile Pro Ala Val His
     45                  50                  55 cgc ctg ctg gga gcg ccg ctc aag ttg gag gat tgt gct ctg caa gtg    243
Arg Leu Leu Gly Ala Pro Leu Lys Leu Glu Asp Cys Ala Leu Gln Val
 60                  65                  70                  75 tct ccc tcc gga tac tac ctg gac acc gag ctg tcc ctg gaa gag cag    291
Ser Pro Ser Gly Tyr Tyr Leu Asp Thr Glu Leu Ser Leu Glu Glu Gln
                 80                  85                  90 cgg gag atg ctg gag ggc ttc tat gaa gag atc agc aaa ggg cgg aag    339
Arg Glu Met Leu Glu Gly Phe Tyr Glu Glu Ile Ser Lys Gly Arg Lys
             95                 100                 105 ccc acg ctg atc ctt cgg acc cag ctc tct gtg agg gtc aac gct atc    387
Pro Thr Leu Ile Leu Arg Thr Gln Leu Ser Val Arg Val Asn Ala Ile
        110                 115                 120 ttg gaa aag ctg tat agc tcc agt ggt cct gag ctc cgc cgc tcc ctc    435
Leu Glu Lys Leu Tyr Ser Ser Ser Gly Pro Glu Leu Arg Arg Ser Leu
    125                 130                 135 ttc tca ctg aag cag atc ttc cag gag gac aaa gac ctg gtg cct gaa    483
Phe Ser Leu Lys Gln Ile Phe Gln Glu Asp Lys Asp Leu Val Pro Glu
140                 145                 150                 155 ttt gtg cat tca gag ggg ctg agc tgc ctg atc cgt gtg ggt gct gct    531
Phe Val His Ser Glu Gly Leu Ser Cys Leu Ile Arg Val Gly Ala Ala
                160                 165                 170 gcc gac cac aac tac cag agc tac atc ctt aga gcg ctc ggc cag ctg    579
Ala Asp His Asn Tyr Gln Ser Tyr Ile Leu Arg Ala Leu Gly Gln Leu
            175                 180                 185 atg ctc ttt gtg gat gga atg ctg ggg gtg gtg gcc cac agt gac act    627
Met Leu Phe Val Asp Gly Met Leu Gly Val Val Ala His Ser Asp Thr
        190                 195                 200 att cag tgg ctg tac aca ttg tgt gcc agc ctg tcc cgc ttg gtg gtg    675
Ile Gln Trp Leu Tyr Thr Leu Cys Ala Ser Leu Ser Arg Leu Val Val
    205                 210                 215 aag aca gcc ctg aag ctg ctg ttg gtg ttt gta gaa tac tcc gaa aac    723
Lys Thr Ala Leu Lys Leu Leu Leu Val Phe Val Glu Tyr Ser Glu Asn
220                 225                 230                 235 aac gca ccg ctg ttc atc cgt gca gtg aac tct gtg gcc agc acc acc    771
Asn Ala Pro Leu Phe Ile Arg Ala Val Asn Ser Val Ala Ser Thr Thr
                240                 245                 250 ggt gct cct ccc tgg gcc aat ctg gtg tcc atc ctg gag gag aag aat    819
Gly Ala Pro Pro Trp Ala Asn Leu Val Ser Ile Leu Glu Glu Lys Asn
            255                 260                 265 ggc gct gac cct gag ttg ttg gtg tac acg gtc acc ctc atc aac aag    867
Gly Ala Asp Pro Glu Leu Leu Val Tyr Thr Val Thr Leu Ile Asn Lys
        270                 275                 280 acg ctg gcg gcg ctc ccg gac cag gac tcc ttc tac gat gtg acg gat    915
Thr Leu Ala Ala Leu Pro Asp Gln Asp Ser Phe Tyr Asp Val Thr Asp
    285                 290                 295 gca ctg gag cag cag ggc atg gaa gcg ctg gtc cag cgc cac ctg ggc    963
Ala Leu Glu Gln Gln Gly Met Glu Ala Leu Val Gln Arg His Leu Gly
300                 305                 310                 315 act gcg ggc act gac gtc gac ctg cgc acg cag ctt gtg ctc tac gag   1011
Thr Ala Gly Thr Asp Val Asp Leu Arg Thr Gln Leu Val Leu Tyr Glu
                320                 325                 330
```

-continued

| | | |
|---|---|---|
| aac gcc ctg aaa ttg gag gat gga gac atc gaa gaa gcc cca ggc gct<br>Asn Ala Leu Lys Leu Glu Asp Gly Asp Ile Glu Glu Ala Pro Gly Ala<br>          335                 340                 345 | | 1059 |
| ggt ggg cgg cgg gaa cga cga aag cct tct tct gag gag ggc aag agg<br>Gly Gly Arg Arg Glu Arg Arg Lys Pro Ser Ser Glu Glu Gly Lys Arg<br>     350                 355                 360 | | 1107 |
| agc cgc cgt tct ctg gaa ggc ggg ggc tgc ccc gcg cgt gcc ccg gaa<br>Ser Arg Arg Ser Leu Glu Gly Gly Gly Cys Pro Ala Arg Ala Pro Glu<br> 365                 370                 375 | | 1155 |
| cct ggc ccc aca ggc ccc gcc tca ccg gta ggc ccc acc tct tcc acc<br>Pro Gly Pro Thr Gly Pro Ala Ser Pro Val Gly Pro Thr Ser Ser Thr<br>380                 385                 390                 395 | | 1203 |
| ggc ccc gcc ctg ctg aca ggc ccc gcc tcc agc cct gtg ggc cct ccc<br>Gly Pro Ala Leu Leu Thr Gly Pro Ala Ser Ser Pro Val Gly Pro Pro<br>                 400                 405                 410 | | 1251 |
| tcc ggt ctc caa gct tca gtg aac ctt ttt cct acc atc tct gtg gca<br>Ser Gly Leu Gln Ala Ser Val Asn Leu Phe Pro Thr Ile Ser Val Ala<br>             415                 420                 425 | | 1299 |
| ccc tca gct gac acc tcc agc gag agg agc atc tac aaa ctt cac caa<br>Pro Ser Ala Asp Thr Ser Ser Glu Arg Ser Ile Tyr Lys Leu His Gln<br>         430                 435                 440 | | 1347 |
| act gct tcc gtt tgagcccggt tcctggagaa tgtggcggca gcagaaacag<br>Thr Ala Ser Val<br>     445 | | 1399 |
| agaagcaggt tgcgctggcc cagggccggg cagagacact tgccggggcc atgcccaatg | | 1459 |
| aggcgggtgg acacccagat gcccggcaac tctgggactc cccagagaca gccccctgcag | | 1519 |
| ccagaacacc ccagagccct gccccctgtg tcctgctccg ggcccagcga agccttgcac | | 1579 |
| cagagcccaa ggagccactg ataccagcaa gccccaaggc tgagcccatc tgggagctcc | | 1639 |
| ctacccgtgc acccaggctc tctattgggg acctggactt ttcagatcta ggggaggatg | | 1699 |
| aagaccagga catgctgaat gtagagtctg tggaggctgg gaaagacatc ccagctccct | | 1759 |
| cacccccact gcccctgctc tcgggagtac ccccccctcc cccacttcca cctcccccac | | 1819 |
| ccatcaaagg cccctcccca ccacctccac ctctacctct ggctgcccct cttcccatt | | 1879 |
| cagtgcctga cagctcagcc ctccccacta agaggaagac agtaaaactt ttctggcgtg | | 1939 |
| agctgaagct ggctggggc catggagtct ctgcaagccg cttgggccc tgcgccaccc | | 1999 |
| tctgggcttc actggaccct gtctcagtgg acacggcccg actggaacac ctctttgagt | | 2059 |
| ctcgtgccaa agaggtgctg ccctccaaga aagctggaga gggccgccgg acaatgacca | | 2119 |
| cagtgctgga ccccaagcgc agcaacgcca tcaacatcgg cctaaccaca ctgccacctg | | 2179 |
| tgcatgtcat taaggctgct ctgctcaact ttgatgagtt tgctgtcagc aaggatggca | | 2239 |
| ttgagaagct actgaccatg atgcccacgg aggaagagcg gcagaagatt gaggaagccc | | 2299 |
| agctggccaa ccctgacata cccctgggcc cagccgagaa cttcctgatg actcttgcct | | 2359 |
| ccattggcgg cctcgctgct cgtctacaac tctgggcctt caagctggac tatgacagca | | 2419 |
| tggagcggga aattgctgag ccactgtttt acctgaaagt gggtatggaa cagctggtac | | 2479 |
| agaatgccac cttccgctgc atcctggcta ccctcctagc ggtgggcaac ttcctcaatg | | 2539 |
| gctcccagag cagcggcttt gagctgagct acctggagaa ggtgtcagag gtgaaggaca | | 2599 |
| cggtgcgtcg acagtcactg ctacaccatc tctgctccct agtgctccag acccggcctg | | 2659 |
| agtcctctga cctctattca gaaatccctg ccctgacccg ctgtgccaag gtggactttg | | 2719 |
| aacagctgac tgagaacctg gggcagctgg agcgccggag ccgggcagcc gaggagagcc | | 2779 |

```
tgcggagctt ggccaagcat gagctggccc cagccctgcg tgcccgcctc acccacttcc    2839
tggaccagtg tgcccgccgt gttgccatgc taaggatagt gcaccgccgt gtctgcaata    2899
ggttccatgc cttcctgctc tacctgggct acaccccgca ggcggccgt gaagtgcgca     2959 tcatgcagtt ctgccacacg ctgcgggaat ttgcgcttga gtatcggact tgccgggaac    3019
gagtgctaca gcagcagcag aagcaggcca cataccgtga gcgcaacaag acccggggac    3079
gcatgatcac cgagacagag aagttctcag gtgtggctgg ggaagccccc agcaacccct    3139
ctgtcccagt agcagtgagc agcgggccag gccggggaga tgctgacagt catgctagta    3199
tgaagagtct gctgaccagc aggcctgagg acaccacaca caatcgccgc agcagaggca    3259
tggtccagag cagctcccca atcatgccca cagtggggcc ctccactgca tccccagaag    3319 aaccccagg ctccagttta cccagtgata catcagatga gatcatggac cttctggtgc     3379
agtcagtgac caagagcagt cctcgtgcct tagctgctag ggaacgcaag cgttcccgcg    3439
gcaaccgcaa gtctttgaga aggacgttga agagtgggct cggagatgac ctggtgcagg    3499
cactgggact aagcaagggt cctggcctgg aggtgtgaag gtgctgtatc ccggaaatct    3559
atctggaccc tggactgcag tgcaggagat gacagagtga ggagggccca gagcagaatt    3619
ctggccccag aactctgtgc ccaggagcca tgccttgagc agtattagcc gtgtgtgtat    3679
gcatgtgagt gtgtgtgtat gtgtgtgtgt gcatgcatat gcatgtgcat gtgtgtgagc    3739
tccttgaacg cacggagcaa aataaaattt tcttagctaa tccaaaaaaa aaaaaaaaa     3799
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
tgagccggcc gcagagccat gg                                              22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
tgctccgtgc gttcaaggag ctcac                                           25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
cctaccatct ctgtggcacc ctcagct                                         27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10

-continued ttggggcttg ctggtatcag tggctcc    27

<210> SEQ ID NO 11
<211> LENGTH: 109
<212> TYPE: PRT
<213> ORGANISM: Homo sapiens

<400> SEQUENCE: 11

Met Glu Thr Phe Thr Asn Asp Arg Leu Gln Leu Pro Arg Asn Met Ile
1               5                   10                  15

Glu Asn Ser Met Phe Glu Glu Pro Asp Val Val Asp Leu Ala Lys
            20                  25                  30

Glu Pro Cys Leu His Pro Leu Glu Pro Asp Glu Val Glu Tyr Glu Pro
        35                  40                  45

Arg Gly Ser Arg Leu Leu Val Arg Gly Leu Gly Glu His Glu Met Asp
    50                  55                  60

Glu Asp Glu Glu Asp Tyr Glu Ser Ser Ala Lys Leu Leu Gly Met Ser
65                  70                  75                  80

Phe Met Asn Arg Ser Ser Gly Leu Arg Asn Ser Ala Thr Gly Tyr Arg
                85                  90                  95

Gln Ser Pro Asp Gly Thr Cys Ser Val Pro Ser Ala Arg
            100                 105

<210> SEQ ID NO 12
<211> LENGTH: 327
<212> TYPE: DNA
<213> ORGANISM: Homo sapiens

<400> SEQUENCE: 12
atggagacct ttaccaatga tcgacttcag cttccaagga atatgattga aaacagcatg    60
tttgaagaag aaccagatgt ggtagattta gccaaagaac cttgtttaca tcctctggaa   120
cctgatgaag ttgaatatga gccccgaggt tcgaggcttc tggtgagagg tcttggtgag   180
catgagatgg atgaggatga agaggattat gagtcatctg ccaagctgct gggcatgtcc   240
ttcatgaaca gaagctcagg ccttcggaac agtgcaacag ctacaggca gagtccagat   300 gggacttgtt cagtaccctc tgccagg                                      327

<210> SEQ ID NO 13
<211> LENGTH: 43
<212> TYPE: PRT
<213> ORGANISM: Homo sapiens

<400> SEQUENCE: 13

Lys Val Pro Glu Thr Arg Gly Arg Thr Phe Asp Gln Ile Ser Ala Ala
1               5                   10                  15

Phe Arg Arg Thr Pro Ser Leu Leu Glu Gln Glu Val Lys Pro Ser Thr
            20                  25                  30

Glu Leu Glu Tyr Leu Gly Pro Asp Glu Asn Asp
        35                  40

<210> SEQ ID NO 14
<211> LENGTH: 129
<212> TYPE: DNA
<213> ORGANISM: Homo sapiens

<400> SEQUENCE: 14
aaagtgcctg aaaccagagg ccggacgttt gaccagatct cagctgcctt ccgacggaca    60 vccttcccttt tagagcagga ggtgaaaccc agtacagaac ttgaatactt agggccagat    120
gagaatgac                                                             129

<210> SEQ ID NO 15
<211> LENGTH: 1192
<212> TYPE: PRT
<213> ORGANISM: Mus sp.

<400> SEQUENCE: 15

```
Met Ala Gly Glu Glu Arg Gly Asp Gly Asp Pro Val Ser Val Val
  1               5                  10                  15

Thr Val Arg Val Gln Tyr Leu Glu Asp Thr Asp Pro Phe Ala Cys Ala
                 20                  25                  30

Asn Phe Pro Glu Pro Arg Arg Ala Pro Thr Cys Ser Leu Asp Gly Ala
             35                  40                  45

Leu Pro Leu Ser Ala Gln Ile Pro Ala Leu His Arg Leu Leu Gly Ala
         50                  55                  60

Pro Leu Lys Leu Glu Asp Cys Ala Leu Gln Val Ser Pro Ser Gly Tyr
 65                  70                  75                  80

Tyr Leu Asp Pro Glu Leu Ser Leu Glu Glu Gln Arg Glu Met Leu Glu
                 85                  90                  95

Gly Phe Tyr Glu Glu Ile Ser Lys Gly Arg Lys Pro Thr Leu Ile Leu
                100                 105                 110

Arg Thr Gln Leu Ser Val Arg Val Asn Ala Ile Leu Glu Lys Leu Tyr
            115                 120                 125

Gly Ser Ser Gly Pro Glu Leu Arg Arg Ser Leu Phe Ser Leu Lys Gln
        130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Glu Thr Val Gln Trp Leu Tyr
        195                 200                 205

Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Gln Ala Val Asn Ala Val Ala Ser Ala Thr Gly Thr Leu Pro Trp
                245                 250                 255

Ala Asn Leu Val Ser Ile Leu Glu Glu Lys Asn Gly Ala Asp Ala Glu
            260                 265                 270

Leu Leu Val Tyr Thr Val Thr Leu Ile Asn Lys Thr Leu Ala Ala Leu
        275                 280                 285

Pro Asp Gln Asp Ser Phe Tyr Asp Val Thr Asp Ala Leu Glu Gln Gln
    290                 295                 300

Gly Met Glu Ala Leu Val Gln Arg Phe Leu Gly Thr Ala Gly Thr Asp
305                 310                 315                 320

Val Asp Leu Arg Thr Gln Leu Thr Leu Tyr Glu Ser Ala Leu Arg Leu
                325                 330                 335

Glu Asp Gly Asp Met Glu Ala Ala Ala Ala Ala Ala Gly Gly
            340                 345                 350
```

-continued

```
Arg Arg Glu Arg Arg Lys Pro Ser Ser Glu Glu Gly Lys Arg Ser Arg
            355                 360                 365
Arg Ser Leu Glu Gly Gly Cys Pro Val Arg Ala Pro Glu Pro Gly
    370                 375                 380
Ser Thr Gly Ser Ala Ser Pro Val Gly Ser Thr Pro Ser Thr Gly Ser
385                 390                 395                 400
Ala Pro Pro Thr Asn Pro Ala Phe Ser Ser Thr Gly Pro Ala Ser Gly
                405                 410                 415
Leu Leu Arg Thr Ser Val Asn Leu Phe Pro Thr Ile Ser Val Gly Pro
            420                 425                 430
Ser Val Asp Ser Ser Cys Glu Arg Ser Val Tyr Lys Leu His Gln Thr
            435                 440                 445
Ala Pro Val Cys Ser Pro Glu Ser Pro Val Pro Gln Ser Leu Pro
    450                 455                 460
Gly Gln Ala Arg Leu Glu Ala Arg Phe Leu Glu Asn Val Ala Ala Ala
465                 470                 475                 480
Glu Thr Glu Lys Gln Ala Ala Leu Ala Gln Gly Arg Ala Glu Thr Leu
            485                 490                 495
Ala Gly Ala Thr Val Asp Asp Thr Asp Gly Ser Ser Gly Thr Arg Glu
            500                 505                 510
Leu Trp Asp Ser Pro Glu Pro Ala Ser Ala Pro Arg Thr Pro Gln Ser
            515                 520                 525
Pro Val Ser Arg Ile Leu Leu Arg Thr Gln Arg Ser Leu Glu Pro Glu
            530                 535                 540
Pro Lys Lys Pro Val Ser Pro Pro Ser Pro Lys Ala Glu Pro Ile Gln
545                 550                 555                 560
Glu Pro Pro Thr Cys Val Pro Lys Leu Cys Ile Gly Asp Leu Asp Phe
                565                 570                 575
Ser Asp Leu Gly Glu Asp Glu Asp Gln Asp Thr Leu Asn Val Glu Ser
            580                 585                 590
Val Glu Ala Gly Lys Ala Ser Pro Phe Leu Ser Ser Leu Ser Pro Ser
            595                 600                 605
Leu Ser Gly Gly Pro Pro Pro Pro Pro Pro Pro Pro Pro Pro Ile Thr
    610                 615                 620
Gly Ser Cys Pro Pro Pro Pro Leu Ala Ala Pro Phe Thr His Ser
625                 630                 635                 640
Ala Leu Asp Gly Pro Arg His Pro Thr Lys Arg Lys Thr Val Lys Leu
                645                 650                 655
Phe Trp Arg Glu Leu Lys Leu Thr Gly Gly Pro Gly Cys Ser Arg Ser
                660                 665                 670
Arg Phe Gly Pro Cys Pro Thr Leu Trp Ala Ser Leu Glu Pro Val Ser
            675                 680                 685
Val Asp Thr Ala Arg Leu Glu His Leu Phe Glu Ser Arg Ala Lys Asp
            690                 695                 700
Val Leu Pro Thr Lys Lys Ala Gly Gly Arg Arg Thr Met Thr Val
705                 710                 715                 720
Val Leu Asp Pro Lys Arg Ser Asn Ala Ile Asn Ile Gly Leu Thr Thr
                725                 730                 735
Leu Pro Pro Val His Val Ile Lys Ala Leu Leu Asn Phe Asp Glu
            740                 745                 750
Phe Ala Val Ser Lys Asp Gly Ile Glu Lys Leu Leu Thr Met Met Pro
            755                 760                 765
```

```
Thr Glu Glu Glu Arg Gln Lys Ile Glu Glu Ala Gln Leu Ala Asn Pro
    770                 775                 780

Asp Val Pro Leu Gly Pro Ala Glu Asn Phe Leu Met Thr Leu Ala Ser
785                 790                 795                 800

Ile Gly Gly Leu Ala Ala Arg Leu Gln Leu Trp Ala Phe Lys Leu Asp
                805                 810                 815

Tyr Glu Ser Met Glu Arg Glu Ile Ala Glu Pro Leu Phe Asp Leu Lys
            820                 825                 830

Val Gly Met Glu Gln Leu Val His Asn Ala Thr Phe Arg Cys Ile Leu
        835                 840                 845

Ala Thr Leu Leu Ala Val Gly Asn Phe Leu Asn Gly Ser Gln Ser Ser
    850                 855                 860

Gly Phe Glu Leu Ser Tyr Leu Glu Lys Val Ser Glu Val Lys Asp Thr
865                 870                 875                 880

Val Arg Arg Gln Ser Leu Leu Tyr His Leu Cys Ser Leu Val Leu Gln
                885                 890                 895

Thr Arg Pro Asp Ser Ser Asp Leu Tyr Ser Glu Ile Pro Ala Leu Thr
            900                 905                 910

Arg Cys Ala Lys Val Asp Phe Glu Gln Leu Thr Glu Asn Leu Gly Gln
        915                 920                 925

Leu Glu Cys Arg Ser Gln Ala Ala Glu Asp Ser Leu Arg Ser Leu Ala
    930                 935                 940

Lys His Glu Leu Ser Pro Ala Leu Arg Ala Arg Leu Thr His Phe Leu
945                 950                 955                 960

Ala Gln Cys Thr Arg Arg Val Ala Met Leu Arg Val Val His Arg Arg
                965                 970                 975

Val Cys Asn Arg Phe His Ala Phe Leu Leu Tyr Leu Gly Tyr Thr Pro
            980                 985                 990

Gln Ala Ala Arg Asp Val Arg Ile Met Gln Phe Cys His Thr Leu Arg
        995                 1000                1005

Glu Phe Ala Leu Glu Tyr Arg Thr Cys Arg Glu Arg Val Leu Gln Gln
   1010                1015                1020

Gln Gln Lys Arg Ala Thr Tyr Arg Glu Arg Asn Lys Thr Arg Gly Arg
1025                1030                1035                1040

Met Ile Thr Glu Thr Glu Lys Phe Ser Gly Val Ala Gly Glu Ala Pro
                1045                1050                1055

Asn Asn Leu Ser Val Pro Val Ala Val Gly Ser Gly Pro Gly Gln Gly
            1060                1065                1070

Asp Thr Asp Asn His Ala Ser Met Lys Ser Leu Leu Thr Ser Arg Pro
        1075                1080                1085

Glu Asp Ala Thr His Ser Arg Arg Ser Arg Gly Met Val Gln Ser Ser
    1090                1095                1100

Ser Pro Val Ser His Thr Ala Val Gly Pro Ser Ala Ala Ser Pro Glu
1105                1110                1115                1120

Glu Thr Ala Ala Ser Gly Leu Pro Thr Asp Thr Ser Asp Glu Ile Met
                1125                1130                1135

Asp Leu Leu Val Gln Ser Val Thr Lys Ser Gly Pro Arg Ala Leu Ala
            1140                1145                1150

Ala Arg Glu Arg Lys Arg Ser Arg Gly Asn Arg Lys Ser Leu Arg Arg
        1155                1160                1165

Thr Leu Lys Ser Gly Leu Gly Asp Asp Leu Val Gln Ala Leu Gly Leu
    1170                1175                1180
```

Ser Lys Ala Pro Gly Leu Glu Val
1185              1190

<210> SEQ ID NO 16
<211> LENGTH: 3576
<212> TYPE: DNA
<213> ORGANISM: Mus sp.

<400> SEQUENCE: 16

| | | | | | | |
|---|---|---|---|---|---|---|
| atggcgggcg | aggaagagcg | cggggatggg | gacccagtat | ccgtggtaac | tgtgagagtg | 60 |
| cagtacctgg | aagacaccga | ccctttcgct | tgtgccaact | cccggaacc | acgccgggcc | 120 |
| cccacctgca | gcctggacgg | ggctctgccc | ctgagtgcgc | agatccctgc | tctgcaccga | 180 |
| ctcctggggg | cgcctcttaa | gctggaggac | tgtgcattgc | aagtgtctcc | ctccggatac | 240 |
| tacctggacc | cggagctgtc | cctagaagaa | cagcgggaga | tgctggaggg | tttctatgaa | 300 |
| gagatcagca | aaggcggaa | gcccacgtta | atcctgcgga | cccagctctc | cgtgagggtc | 360 |
| aatgctatct | tggaaaagct | gtatggctcc | agtggccccg | agctccgccg | atctctcttc | 420 |
| tcattaaagc | agatattcca | ggaagacaag | gacctggtgc | ccgaattcgt | gcactcggag | 480 |
| ggtctgagtt | gcctgatccg | cgtgggtgct | gctgcagacc | acaactacca | gagctacatc | 540 |
| cttcgagccc | tgggccagct | gatgctgttt | gtggatggga | tgctgggggt | ggtggcccac | 600 |
| agcgagaccg | tgcagtggct | gtataccctg | tgtgctagcc | tgtcccgctt | ggtggtaaag | 660 |
| acagccctga | gctgctgct | ggtgtttgtg | gagtattccg | agaacaacgc | gccgctgttc | 720 |
| atccaggcag | tcaacgcagt | agccagtgcc | accggtactc | ttccctgggc | caacttggtg | 780 |
| tccatcctgg | aggagaagaa | tggagctgat | gcagagttgt | tggtgtacac | tgtcactctc | 840 |
| attaacaaga | cgctggcggc | actcccagac | caggactcct | tctatgatgt | gacagatgct | 900 |
| ctggagcagc | agggcatgga | agcgctggtc | aacgtttct | tgggcaccgc | tggcactgat | 960 |
| gttgacctgc | gaacccagct | aacgctctat | gagagtgccc | ttcggttaga | ggatggagat | 1020 |
| atggaagagc | tgcagccgc | cgctgctgca | ggtggccggc | gagagcggcg | gaagccatcc | 1080 |
| tcggaggagg | gcaaaaggag | ccgaagatca | ctagaaggtg | gaggctgccc | tgtgcgtgcc | 1140 |
| ccagaacctg | gctctacagg | ctccgcctca | ccagtaggct | ccaccccctc | cactggctcc | 1200 |
| gccccgccta | caaatccagc | cttcagctct | actggcccag | cctctggcct | tcttcgaacc | 1260 |
| tcagtgaacc | tctttcctac | catttccgtg | gggccgtcag | tggacagttc | ctgtgagaga | 1320 |
| agcgtctaca | aacttcacca | aactgctccc | gtttgctccc | ctgagagtcc | acctgtcccc | 1380 |
| cagtcccttc | ctgggcaggc | caggctagaa | gcccggttcc | tggagaatgt | ggcggcagca | 1440 |
| gagacggaga | agcaggctgc | tctggcccaa | ggccgagcgg | agacgctggc | tggagccacg | 1500 |
| gtagatgaca | ctgatggatc | atcaggcaca | agggaactgt | gggactcccc | agagccagcc | 1560 |
| tctgcaccca | ggacaccca | gagccctgtt | tcccgaatcc | tgctgcgcac | ccagcggagt | 1620 |
| cttgagccag | agcccaagaa | gccagtgtca | ccaccaagcc | ctaaggctga | gcctatccag | 1680 |
| gagcctccca | cctgtgtccc | caagctctgc | attgggact | ggacttctc | agacctaggg | 1740 |
| gaggatgaag | accaggacac | actgaatgtg | gaatctgtgg | aggctggaaa | agcatctccc | 1800 |
| ttcctgtcat | ctctatcgcc | ctcactctct | ggggtcccc | ctcctccgcc | cccacctcct | 1860 |
| ccacccatca | caggctcctg | cccaccgcct | ccaccctgg | ctgctccttt | acccactca | 1920 |
| gcacttgacg | gccaaggca | ccccaccaaa | aggaagacga | taaaactttt | ctggcgggaa | 1980 |
| ctaaagctga | ctgggggccc | tgggtgctct | agaagccgct | ttgggccttg | tcctaccctg | 2040 |

-continued

```
tgggcctcgc tggaacccgt ctcggtggac acagcccgcc tggaacacct atttgagtcc    2100
agagccaagg atgtgctacc aaccaagaaa gctggtgagg ccgccggac aatgaccgta     2160
gtgctggacc ccaagcgcag caatgccatc aacattggcc taaccactct gccacccgtg    2220
cacgtcatca aggctgccct gctcaacttc gatgagtttg ctgtcagcaa agatggcatt    2280
gagaaactgc tgacaatgat gcccacggag aagagcggc agaagattga ggaagcccag     2340
ctggctaacc ccgatgtacc cctcggcccc gctgagaatt tcctgatgac gcttgcttcc    2400
attggaggcc tggctgcgcg cctacagctc tgggctttca agctggacta tgaaagcatg    2460
gagcgggaaa ttgcagagcc actgtttgat ctgaaagtgg gcatggaaca gctggtacac    2520
aatgccacct tccgctgtat tctggctacc cttttggctg tgggcaactt cctcaatggt    2580
tcccagagca gtggctttga gctgagctac ctggagaagg tgtcagaagt gaaggacaca    2640
gtgcgacggc agtcattgct ctatcatctc tgctccctgg tgctccagac ccgacctgat    2700
tcctctgacc tctactcaga aattcctgcc ctcacccgct gtgccaaggt ggactttgaa    2760
cagctgactg agaacctagg gcagctggag tgccggagcc aggctgccga ggacagcctc    2820
cggagcttgg ctaagcacga gctctcccca gctctgcgtg ctcgcctcac ccacttcttg    2880
gcccagtgta cccgccgggt agccatgtta agagtagtgc atcgccgagt ctgcaatagg    2940
ttccatgcct tcctgctcta cctgggctac accccacagg cagcaaggga tgtacgcatc    3000
atgcagttct gccacacact gagagagttt gcccttgagt atcggacttg tcgggaacgg    3060
gtactgcagc agcagcagaa gcgggctaca taccgtgagc gcaacaagac ccgtggtcgc    3120
atgattaccg agacagagaa gttctcaggt gtggctgggg aggcccccaa taacctgtct    3180
gtcccagtgg ctgtgggcag cgggccaggt cagggtgata ctgacaatca tgccagcatg    3240
aagagcctgc ttaccagcag gccggaagat gccacacaca gccgacgcag cagaggtatg    3300
gtccagagca gttcccccgt ctcacacaca gcagtggggc cctccgctgc atcccctgag    3360
gagactgcag cctccggctt acccaccgac acgtcagatg agataatgga cctgctggtg    3420
cagtcagtta ccaagagcgg tcctagagcc ttagctgctc gggagaggaa gcgctctcgt    3480
ggcaaccgaa agtccttgag acggacactg aagagtggac ttggagatga cctggtgcag    3540
gcactgggac taagcaaagc tcctggtcta gaggtg                              3576
```

<210> SEQ ID NO 17
<211> LENGTH: 1166
<212> TYPE: PRT
<213> ORGANISM: Mus sp.

<400> SEQUENCE: 17

Met Ala Gly Glu Glu Arg Gly Asp Gly Asp Pro Val Ser Val Val
1               5                   10                  15

Thr Val Arg Val Gln Tyr Leu Glu Asp Thr Asp Pro Phe Ala Cys Ala
                20                  25                  30

Asn Phe Pro Glu Pro Arg Arg Ala Pro Thr Cys Ser Leu Asp Gly Ala
            35                  40                  45

Leu Pro Leu Ser Ala Gln Ile Pro Ala Leu His Arg Leu Leu Gly Ala
        50                  55                  60

Pro Leu Lys Leu Glu Asp Cys Ala Leu Gln Val Ser Pro Ser Gly Tyr
65                  70                  75                  80

Tyr Leu Asp Pro Glu Leu Ser Leu Glu Glu Gln Arg Glu Met Leu Glu
                85                  90                  95

```
Gly Phe Tyr Glu Glu Ile Ser Lys Gly Arg Lys Pro Thr Leu Ile Leu
            100                 105                 110

Arg Thr Gln Leu Ser Val Arg Val Asn Ala Ile Leu Glu Lys Leu Tyr
        115                 120                 125

Gly Ser Ser Gly Pro Glu Leu Arg Arg Ser Leu Phe Ser Leu Lys Gln
    130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Glu Thr Val Gln Trp Leu Tyr
        195                 200                 205

Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Gln Ala Val Asn Ala Val Ala Ser Ala Thr Gly Thr Leu Pro Trp
                245                 250                 255

Ala Asn Leu Val Ser Ile Leu Glu Glu Lys Asn Gly Ala Asp Ala Glu
            260                 265                 270

Leu Leu Val Tyr Thr Val Thr Leu Ile Asn Lys Thr Leu Ala Ala Leu
        275                 280                 285

Pro Asp Gln Asp Ser Phe Tyr Asp Val Thr Asp Ala Leu Glu Gln Gln
    290                 295                 300

Gly Met Glu Ala Leu Val Gln Arg Phe Leu Gly Thr Ala Gly Thr Asp
305                 310                 315                 320

Val Asp Leu Arg Thr Gln Leu Thr Leu Tyr Glu Ser Ala Leu Arg Leu
                325                 330                 335

Glu Asp Gly Asp Met Glu Glu Ala Ala Ala Ala Ala Gly Gly
            340                 345                 350

Arg Arg Glu Arg Arg Lys Pro Ser Ser Glu Glu Gly Lys Arg Ser Arg
        355                 360                 365

Arg Ser Leu Glu Gly Gly Cys Pro Val Arg Ala Pro Glu Pro Gly
    370                 375                 380

Ser Thr Gly Ser Ala Ser Pro Val Gly Ser Thr Pro Ser Thr Gly Ser
385                 390                 395                 400

Ala Pro Pro Thr Asn Pro Ala Phe Ser Ser Thr Gly Pro Ala Ser Gly
                405                 410                 415

Leu Leu Arg Thr Ser Val Asn Leu Phe Pro Thr Ile Ser Val Gly Pro
            420                 425                 430

Ser Val Asp Ser Ser Cys Glu Arg Ser Val Tyr Lys Ala Arg Phe Leu
        435                 440                 445

Glu Asn Val Ala Ala Ala Glu Thr Glu Lys Gln Ala Ala Leu Ala Gln
    450                 455                 460

Gly Arg Ala Glu Thr Leu Ala Gly Ala Thr Val Asp Asp Thr Asp Gly
465                 470                 475                 480

Ser Ser Gly Thr Arg Glu Leu Trp Asp Ser Pro Glu Pro Ala Ser Ala
                485                 490                 495

Pro Arg Thr Pro Gln Ser Pro Val Ser Arg Ile Leu Leu Arg Thr Gln
            500                 505                 510
```

```
Arg Ser Leu Glu Pro Glu Pro Lys Lys Pro Val Ser Pro Pro Ser Pro
        515                 520                 525

Lys Ala Glu Pro Ile Gln Glu Pro Pro Thr Cys Val Pro Lys Leu Cys
        530                 535                 540

Ile Gly Asp Leu Asp Phe Ser Asp Leu Gly Glu Asp Glu Asp Gln Asp
545                 550                 555                 560

Thr Leu Asn Val Glu Ser Val Glu Ala Gly Lys Ala Ser Pro Phe Leu
                565                 570                 575

Ser Ser Leu Ser Pro Ser Leu Ser Gly Gly Pro Pro Pro Pro Pro Pro
                580                 585                 590

Pro Pro Pro Pro Ile Thr Gly Ser Cys Pro Pro Pro Pro Pro Leu Ala
        595                 600                 605

Ala Pro Phe Thr His Ser Ala Leu Asp Gly Pro Arg His Pro Thr Lys
        610                 615                 620

Arg Lys Thr Val Lys Leu Phe Trp Arg Glu Leu Lys Leu Thr Gly Gly
625                 630                 635                 640

Pro Gly Cys Ser Arg Ser Arg Phe Gly Pro Cys Pro Thr Leu Trp Ala
                645                 650                 655

Ser Leu Glu Pro Val Ser Val Asp Thr Ala Arg Leu Glu His Leu Phe
                660                 665                 670

Glu Ser Arg Ala Lys Asp Val Leu Pro Thr Lys Ala Gly Glu Gly
        675                 680                 685

Arg Arg Thr Met Thr Val Val Leu Asp Pro Lys Arg Ser Asn Ala Ile
        690                 695                 700

Asn Ile Gly Leu Thr Thr Leu Pro Pro Val His Val Ile Lys Ala Ala
705                 710                 715                 720

Leu Leu Asn Phe Asp Glu Phe Ala Val Ser Lys Asp Gly Ile Glu Lys
                725                 730                 735

Leu Leu Thr Met Met Pro Thr Glu Glu Glu Arg Gln Lys Ile Glu Glu
            740                 745                 750

Ala Gln Leu Ala Asn Pro Asp Val Pro Leu Gly Pro Ala Glu Asn Phe
        755                 760                 765

Leu Met Thr Leu Ala Ser Ile Gly Gly Leu Ala Ala Arg Leu Gln Leu
        770                 775                 780

Trp Ala Phe Lys Leu Asp Tyr Glu Ser Met Glu Arg Glu Ile Ala Glu
785                 790                 795                 800

Pro Leu Phe Asp Leu Lys Val Gly Met Glu Gln Leu Val His Asn Ala
                805                 810                 815

Thr Phe Arg Cys Ile Leu Ala Thr Leu Leu Ala Val Gly Asn Phe Leu
        820                 825                 830

Asn Gly Ser Gln Ser Ser Gly Phe Glu Leu Ser Tyr Leu Glu Lys Val
        835                 840                 845

Ser Glu Val Lys Asp Thr Val Arg Arg Gln Ser Leu Leu Tyr His Leu
        850                 855                 860

Cys Ser Leu Val Leu Gln Thr Arg Pro Asp Ser Ser Asp Leu Tyr Ser
865                 870                 875                 880

Glu Ile Pro Ala Leu Thr Arg Cys Ala Lys Val Asp Phe Glu Gln Leu
                885                 890                 895

Thr Glu Asn Leu Gly Gln Leu Glu Cys Arg Ser Gln Ala Ala Glu Asp
            900                 905                 910

Ser Leu Arg Ser Leu Ala Lys His Glu Leu Ser Pro Ala Leu Arg Ala
        915                 920                 925
```

```
Arg Leu Thr His Phe Leu Ala Gln Cys Thr Arg Arg Val Ala Met Leu
    930                 935                 940

Arg Val Val His Arg Arg Val Cys Asn Arg Phe His Ala Phe Leu Leu
945                 950                 955                 960

Tyr Leu Gly Tyr Thr Pro Gln Ala Ala Arg Asp Val Arg Ile Met Gln
                965                 970                 975

Phe Cys His Thr Leu Arg Glu Phe Ala Leu Glu Tyr Arg Thr Cys Arg
            980                 985                 990

Glu Arg Val Leu Gln Gln Gln Lys Arg Ala Thr Tyr Arg Glu Arg
        995                1000               1005

Asn Lys Thr Arg Gly Arg Met Ile Thr Glu Thr Glu Lys Phe Ser Gly
1010                1015                1020

Val Ala Gly Glu Ala Pro Asn Asn Leu Ser Val Pro Val Ala Val Gly
1025                1030                1035               1040

Ser Gly Pro Gly Gln Gly Asp Thr Asp Asn His Ala Ser Met Lys Ser
                1045                1050               1055

Leu Leu Thr Ser Arg Pro Glu Asp Ala Thr His Ser Arg Arg Ser Arg
            1060                1065               1070

Gly Met Val Gln Ser Ser Pro Val Ser His Thr Ala Val Gly Pro
        1075                1080               1085

Ser Ala Ala Ser Pro Glu Glu Thr Ala Ala Ser Gly Leu Pro Thr Asp
    1090                1095               1100

Thr Ser Asp Glu Ile Met Asp Leu Leu Val Gln Ser Val Thr Lys Ser
1105                1110                1115               1120

Gly Pro Arg Ala Leu Ala Arg Glu Arg Lys Arg Ser Arg Gly Asn
                1125                1130               1135

Arg Lys Ser Leu Arg Arg Thr Leu Lys Ser Gly Leu Gly Asp Asp Leu
            1140                1145               1150

Val Gln Ala Leu Gly Leu Ser Lys Ala Pro Gly Leu Glu Val
        1155                1160               1165

<210> SEQ ID NO 18
<211> LENGTH: 3498
<212> TYPE: DNA
<213> ORGANISM: Mus sp.

<400> SEQUENCE: 18
atggcgggcg aggaagagcg cggggatggg gacccagtat ccgtggtaac tgtgagagtg     60
cagtacctgg aagacaccga cccttcgct tgtgccaact tcccggaacc acgccgggcc    120
cccacctgca gcctggacgg ggctctgccc ctgagtgcgc agatccctgc tctgcaccga    180
ctcctggggg cgcctcttaa gctggaggac tgtgcattgc aagtgtctcc ctccggatac    240
tacctggacc cggagctgtc cctagaagaa cagcgggaga tgctggaggg tttctatgaa    300
gagatcagca aaggcggaa gcccacgtta atcctgcgga cccagctctc cgtgagggtc    360
aatgctatct ggaaaagct gtatggctcc agtggccccg agctccgccg atctctcttc    420
tcattaaagc agatattcca ggaagacaag gacctggtgc ccgaattcgt gcactcggag    480
ggtctgagtt gcctgatccg cgtgggtgct gctgcagacc acaactacca gagctacatc    540
cttcgagccc tgggccagct gatgctgttt gtggatggga tgctgggggt ggtggcccac    600
agcgagaccg tgcagtggct gtatacctg tgtgctagcc tgtcccgctt ggtggtaaag    660
acagccctga gctgctgct ggtgtttgtg gagtattccg agaacaacgc gccgctgttc    720
atccaggcag tcaacgcagt agccagtgcc accggtactc ttccctgggc caacttggtg    780
```

-continued

```
tccatcctgg aggagaagaa tggagctgat gcagagttgt tggtgtacac tgtcactctc    840
attaacaaga cgctggcggc actcccagac caggactcct tctatgatgt gacagatgct    900
ctggagcagc agggcatgga agcgctggtc aacgtttct tgggcaccgc tggcactgat     960
gttgacctgc gaacccagct aacgctctat gagagtgccc ttcgttaga ggatggagat    1020
atggaagagg ctgcagccgc cgctgctgca ggtggccggc gagagcggcg gaagccatcc   1080
tcggaggagg gcaaaaggag ccgaagatca ctagaaggtg gaggctgccc tgtgcgtgcc   1140
ccagaacctg gctctacagg ctccgcctca ccagtaggct ccaccccctc cactggctcc   1200
gccccgccta caaatccagc cttcagctct actgggccag cctctggcct tcttcgaacc   1260
tcagtgaacc tctttcctac catttccgtg gggccgtcag tggacagttc ctgtgagaga   1320
agcgtctaca aagcccggtt cctggagaat gtggcggcag cagagacgga gaagcaggct   1380
gctctggccc aaggccgagc ggagacgctg gctggagcca cggtagatga cactgatgga   1440
tcatcaggca aagggaact gtgggactcc ccagagccag cctctgcacc caggacaccc    1500
cagagccctg tttccgaat cctgctgcgc acccagcgga gtcttgagcc agagcccaag    1560
aagccagtgt caccaccaag ccctaaggct gagcctatcc aggagcctcc cacctgtgtc   1620
cccaagctct gcattgggga cttggacttc tcagacctag gggaggatga agaccaggac   1680
acactgaatg tggaatctgt ggaggctgga aaagcatctc ccttcctgtc atctctatcg   1740
ccctcactct ctgggggtcc ccctcctccg ccccacctc ctccacccat acaggctcc     1800
tgcccaccgc ctccacccct ggctgctcct tttacccact cagcacttga cggcccaagg   1860
caccccacca aaaggaagac agtaaaactt ttctggcggg aactaaagct gactgggggc   1920
cctgggtgct ctagaagccg ctttgggcct tgtcctaccc tgtgggcctc gctggaaccc   1980
gtctcggtgg acacagcccg cctggaacac ctatttgagt ccagagccaa ggatgtgcta   2040
ccaaccaaga aagctggtga gggccgccgg acaatgaccg tagtgctgga ccccaagcgc   2100
agcaatgcca tcaacattgg cctaaccact ctgccacccg tgcacgtcat caaggctgcc   2160
ctgctcaact tcgatgagtt tgctgtcagc aaagatggca ttgagaaact gctgacaatg   2220
atgcccacgg aggaagagcg gcagaagatt gaggaagccc agctggctaa ccccgatgta   2280
cccctcggcc ccgctgagaa tttcctgatg acgcttgctt ccattggagg cctggctgcg   2340
cgcctacagc tctgggcttt caagctggac tatgaaagca tggagcggga aattgcagag   2400
ccactgtttg atctgaaagt gggcatggaa cagctggtac acaatgccac cttccgctgt   2460
attctggcta cccttttggc tgtgggcaac ttcctcaatg gttcccagag cagtggcttt   2520
gagctgagct acctggagaa ggtgtcagaa gtgaaggaca cagtgcgacg gcagtcattg   2580
ctctatcatc tctgctccct ggtgctccag acccgacctg attcctctga cctctactca   2640
gaaattcctg ccctcacccg ctgtgccaag gtggactttg aacagctgac tgagaaccta   2700
gggcagctgg agtgccggag ccaggctgcc gaggacagcc tccggagctt ggctaagcac   2760
gagctctccc cagctctgcg tgctcgcctc acccacttct ggcccagtg tacccgccgg   2820
gtagccatgt taagagtagt gcatcgccga gtctgcaata ggttccatgc cttcctgctc   2880
tacctgggct acacccccaca ggcagcaagg gatgtacgca tcatgcagtt ctgccacaca   2940
ctgagagagt ttgcccttga gtatcggact tgtcgggaac gggtactgca gcagcagcag   3000
aagcgggcta catacccgtga gcgcaacaag acccgtggtc gcatgattac cgagacagag   3060
aagttctcag gtgtggctgg ggaggccccc aataacctgt ctgtcccagt ggctgtgggc   3120
agcgggccag gtcagggtga tactgacaat catgccagca tgaagagcct gcttaccagc   3180
```

```
aggccggaag atgccacaca cagccgacgc agcagaggta tggtccagag cagttccccc    3240
gtctcacaca cagcagtggg gccctccgct gcatcccctg aggagactgc agcctccggc    3300
ttacccaccg acacgtcaga tgagataatg gacctgctgg tgcagtcagt taccaagagc    3360
ggtcctagag ccttagctgc tcgggagagg aagcgctctc gtggcaaccg aaagtccttg    3420
agacggacac tgaagagtgg acttggagat gacctggtgc aggcactggg actaagcaaa    3480
gctcctggtc tagaggtg                                                  3498
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19

```
gagtttgctg tcagcaaaga tggcattgag                                     30
```

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 20

```
ttgcttagtc ccagtgcctg caccaggtca tctcc                               35
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 21

```
tgaagttgca gcatttgcag gggacac                                        27
```

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22

```
agctgggctt cctcaatctt ctgccgctct                                     30
```

<210> SEQ ID NO 23
<211> LENGTH: 3853
<212> TYPE: DNA
<213> ORGANISM: Homo sapiens

<400> SEQUENCE: 23

```
tgagccggcc gcagagccat ggcgggcggg aagaccgcg gggacggaga gccggtatca     60
gtggtgaccg tgagggtgca gtacctggaa gacaccgacc ccttcgcatg tgccaacttt    120
ccggagccgc gccgggcccc cacctgcagc ctggacgggg cgctgccctt gggcgcgcag    180
atacccgcgg tgcaccgcct gctgggagcg ccgctcaagt tggaggattg tgctctgcaa    240
gtgtctccct ccggatacta cctggacacc gagctgtccc tggaagagca gcgggagatg    300
```

```
ctggagggct tctatgaaga gatcagcaaa gggcggaagc ccacgctgat ccttcggacc     360
cagctctctg tgagggtcaa cgctatcttg gaaaagctgt atagctccag tggtcctgag     420
ctccgccgct ccctcttctc actgaagcag atcttccagg aggacaaaga cctggtgcct     480
gaatttgtgc attcagaggg gctgagctgc ctgatccgtg tgggtgctgc tgccgaccac     540
aactaccaga gctacatcct tagagcgctc ggccagctga tgctctttgt ggatggaatg     600 ctggggtgg tggcccacag tgacactatt cagtggctgt acacattgtg tgccagcctg      660
tcccgcttgg tggtgaagac agccctgaag ctgctgttgg tgtttgtaga atactccgaa     720
aacaacgcac cgctgttcat ccgtgcagtc aactctgtgg ccagcaccag cggtgctcct     780
ccctgggcca atctggtgtc catcctggag gagaagaatg gcgctgaccc tgagttgttg     840
gtgtacacgt caccctcat caacaagacg ctggcggcgc tcccggacca ggactccttc      900
tacgatgtga cggatgcact ggagcagcag ggcatggaag cgctggtcca gcgccacctg     960
ggcactgcgg gcactgacgt cgacctgcgc acgcagcttg tgctctacga gaacgccctg    1020
aaattggagg atggagacat cgaagaagcc caggcgctg gtgggcggcg ggaacgacga     1080
aagccttctt ctgaggaggg caagaggagc cgccgttctc tggaaggcgg gggctgcccc    1140
gcgcgtgccc cggaacctgg ccccacaggc cccgcctcac cggtaggccc cacctcttcc    1200 accgccccg ccctgctgac aggccccgcc tccagccctg tgggcccctcc ctccggtctc    1260 caagcttcag tgaaccttt tcctaccatc tctgtggcac cctcagctga cacctccagc     1320
gagaggagca tctacaaact tcaccaaact gcttccgttt gggcccctga gcccaccc      1380 gtcccccagt ccctcctgg gcaggccagg ctggaagccc ggttcctgga aatgtggcg      1440 gcagcagaaa cagagaagca ggttgcgctg gcccagggcc gggcagagac acttgccggg    1500
gccatgccca atgaggcggg tggacaccca gatgcccggc aactctggga ctccccagag    1560
acagcccctg cagccagaac accccagagc cctgcccct gtgtcctgct ccgggcccag     1620
cgaagccttg caccagagcc caaggagcca ctgataccag caagcccca ggctgagccc     1680 atctgggagc tccctacccg tgcacccagg ctctctattg ggacctgga cttttcagat     1740 ctaggggagg atgaagacca ggacatgctg aatgtagagt ctgtggaggc tgggaaagac    1800
atcccagctc cctcacccc actgcccctg ctctcgggag taccccccc tccccactt       1860 ccacctcccc cacccatcaa aggccccttc ccaccacctc cacctctacc tctggctgcc    1920
cctcttcccc attcagtgcc tgacagctca gccctcccca ctaagaggaa gacagtaaaa    1980
cttttctggc gtgagctgaa gctggctggg ggccatggag tctctgcaag ccgctttggg    2040
ccctgcgcca ccctctggc ttcactggac cctgtctcag tggacacggc ccgactggaa     2100
cacctctttg agtctcgtgc caaagaggtg ctgccctcca agaaagctgg agagggccgc    2160
cggacaatga ccacagtgct ggaccccaag cgcagcaacg ccatcaacat cggcctaacc    2220
acactgccac ctgtgcatgt cattaaggct gctctgctca actttgatga gtttgctgtc    2280
agcaaggatg gcattgagaa gctactgacc atgatgccca cggaggaaga gcggcagaag    2340
attgaggaag cccagctggc caaccctgac atacccctgg gccagccga gaacttcctg     2400 atgactcttg cctccattgg cggcctcgct gctcgtctac aactctgggc cttcaagctg    2460
gactatgaca gcatggagcg ggaaattgct gagccactgt tgacctgaa agtgggtatg     2520 gaacagctgg tacagaatgc caccttccgc tgcatcctgg ctaccctcct agcggtgggc    2580
aacttcctca atggctccca gagcagcggc tttgagctga gctacctgga gaaggtgtca    2640
gaggtgaagg acacggtgcg tcgacagtca ctgctacacc atctctgctc cctagtgctc    2700
```

```
cagacccggc ctgagtcctc tgacctctat tcagaaatcc ctgccctgac ccgctgtgcc    2760
aaggtggact ttgaacagct gactgagaac ctggggcagc tggagcgccg gagccgggca    2820
gccgaggaga gcctgcggag cttggccaag catgagctgg ccccagccct gcgtgcccgc    2880
ctcacccact tcctggacca gtgtgcccgc cgtgttgcca tgctaaggat agtgcaccgc    2940
cgtgtctgca ataggttcca tgccttcctg ctctacctgg ctacacccc gcaggcggcc    3000 cgtgaagtgc gcatcatgca gttctgccac acgctgcggg aatttgcgct tgagtatcgg    3060
acttgccggg aacgagtgct acagcagcag cagaagcagg ccacataccg tgagcgcaac    3120
aagacccggg gacgcatgat caccgagaca gagaagttct caggtgtggc tggggaagcc    3180
cccagcaacc cctctgtccc agtagcagtg agcagcgggc caggccgggg agatgctgac    3240
agtcatgcta gtatgaagag tctgctgacc agcaggcctg aggacaccac acacaatcgc    3300
cgcagcagag gcatggtcca gagcagctcc ccaatcatgc ccacagtggg gccctccact    3360
gcatccccag aagaaccccc aggctccagt ttacccagtg atacatcaga tgagatcatg    3420
gaccttctgg tgcagtcagt gaccaagagc agtcctcgtg ccttagctgc tagggaacgc    3480
aagcgttccc gcggcaaccg caagtctttg agaaggacgt tgaagagtgg gctcggagat    3540
gacctggtgc aggcactggg actaagcaag ggtcctggcc tggaggtgtg aaggtgctgt    3600
atcccggaaa tctatctgga ccctggactg cagtgcagga gatgacagag tgaggagggc    3660
ccagagcaga attctggccc cagaactctg tgcccaggag ccatgccttg agcagtatta    3720
gccgtgtgtg tatgcatgtg agtgtgtgtg tatgtgtgtg tgtgcatgca tatgcatgtg    3780
catgtgtgtg agctccttga acgcacggag caaaataaaa ttttcttagc taatccaaaa    3840
aaaaaaaaaa aaa                                                      3853

<210> SEQ ID NO 24
<211> LENGTH: 3775
<212> TYPE: DNA
<213> ORGANISM: Homo sapiens

<400> SEQUENCE: 24
tgagccggcc gcagagccat ggcgggcggg aagaccgcg gggacggaga gccggtatca      60
gtggtgaccg tgagggtgca gtacctggaa gacaccgacc ccttcgcatg tgccaacttt    120
ccggagccgc gccgggcccc cacctgcagc ctggacgggg cgctgccctt gggcgcgcag    180
atacccgcgg tgcaccgcct gctggagcg ccgctcaagt tggaggattg tgctctgcaa    240
gtgtctccct ccggatacta cctggacacc gagctgtccc tggaagagca gcgggagatg    300
ctggagggct tctatgaaga gatcagcaaa gggcggaagc ccacgctgat ccttcggacc    360
cagctctctg tgagggtcaa cgctatcttg aaaagctgt atagctccag tggtcctgag    420
ctccgccgct ccctcttctc actgaagcag atcttccagg aggacaaaga cctggtgcct    480
gaatttgtgc attcagaggg gctgagctgc ctgatccgtg tgggtgctgc tgccgaccac    540
aactaccaga gctacatcct tagagcgctc ggccagctga tgctctttgt ggatggaatg    600
ctgggggtgg tggcccacag tgacactatt cagtggctgt acacattgtg tgccagcctg    660
tcccgcttgg tggtgaagac agccctgaag ctgctgttgg tgtttgtaga atactccgaa    720
aacaacgcac cgctgttcat ccgtgcagtg aactctgtgg ccagcaccac cggtgctcct    780
ccctgggcca atctggtgtc catcctggag gagaagaatg cgctgaccc tgagttgttg    840 gtgtacacgg tcaccctcat caacaagacg ctggcggcgc tcccggacca ggactccttc    900
```

```
tacgatgtga cggatgcact ggagcagcag ggcatggaag cgctggtcca gcgccacctg    960
ggcactgcgg gcactgacgt cgacctgcgc acgcagcttg tgctctacga gaacgccctg   1020
aaattggagg atggagacat cgaagaagcc ccaggcgctg gtgggcggcg gaacgacga    1080
aagccttctt ctgaggaggg caagaggagc cgccgttctc tggaaggcgg gggctgcccc   1140
gcgcgtgccc cggaacctgg ccccacaggc cccgcctcac cggtaggccc cacctcttcc   1200
accggccccg ccctgctgac aggccccgcc tccagccctg tgggccctcc ctccggtctc   1260
caagcttcag tgaaccttt tcctaccatc tctgtggcac cctcagctga cacctccagc    1320
gagaggagca tctacaaagc ccggttcctg agaatgtgg cggcagcaga acagagaag    1380
caggttgcgc tggcccaggg ccgggcagag acacttgccg ggccatgcc caatgaggcg    1440
ggtggacacc cagatgcccg gcaactctgg gactccccag agacagcccc tgcagccaga   1500
acacccagat gccctgcccc ctgtgtcctg ctccgggccc agcgaagcct tgcaccagag   1560
cccaaggagc cactgatacc agcaagcccc aaggctgagc ccatctggga gctccctacc   1620
cgtgcaccca ggctctctat tggggacctg acttttcag atctagggga ggatgaagac    1680
caggacatgc tgaatgtaga gtctgtggag gctgggaaag acatcccagc tccctcaccc   1740
ccactgcccc tgctctcggg agtaccccc cctccccac ttccacctcc cccacccatc     1800
aaaggcccct tcccaccacc tccacctcta cctctggctg cccctcttcc ccattcagtg   1860
cctgacagct cagccctccc cactaagagg aagacagtaa aacttttctg cgtgagctg    1920
aagctggctg ggggccatgg agtctctgca agccgctttg ggcctgcgc cacctctgg    1980
gcttcactgg accctgtctc agtggacacg gcccgactgg aacacctctt tgagtctcgt   2040
gccaaagagg tgctgccctc caagaaagct ggagagggcc gccggacaat gaccacagtg   2100
ctggaccca agcgcagcaa cgccatcaac atcggcctaa ccacactgcc acctgtgcat    2160
gtcattaagg ctgctctgct caactttgat gagtttgctg tcagcaagga tggcattgag   2220
aagctactga ccatgatgcc cacggaggaa gagcggcaga agattgagga agcccagctg   2280
gccaaccctg acatacccct gggcccagcc gagaacttcc tgatgactct tgcctccatt   2340
ggcggcctcg ctgctcgtct acaactctgg gccttcaagc tggactatga cagcatggag   2400
cgggaaattg ctgagccact gttgacctg aaagtgggta tggaacagct ggtacagaat    2460
gccaccttcc gctgcatcct ggctaccctc ctagcggtgg gcaacttcct caatggctcc   2520
cagagcagcg gctttgagct gagctacctg gagaaggtgt cagaggtgaa ggacacggtg   2580
cgtcgacagt cactgctaca ccatctctgc tccctagtgc tccagacccg gcctgagtcc   2640
tctgacctct attcagaaat ccctgccctg accgctgtg ccaaggtgga ctttgaacag    2700
ctgactgaga acctgggggca gctggagcgc ggagccggg cagccgagga gagcctgcgg   2760
agcttggcca agcatgagct ggccccagcc ctgcgtgccc gcctcaccca cttcctggac   2820
cagtgtgccc gccgtgttgc catgctaagg atagtgcacc gccgtgtctg caataggttc   2880
catgccttcc tgctctacct gggctacacc ccgcaggcgg cccgtgaagt gcgcatcatg   2940
cagttctgcc acacgctgcg ggaatttgcg cttgagtatc ggacttgccg ggaacgagtg   3000
ctacagcagc agcagaagca ggccacatac cgtgagcgca caagacccg gggacgcatg   3060
atcaccgaga cagagaagtt ctcaggtgtg ctggggaag cccccagcaa ccctctgtc    3120
ccagtagcag tgagcagcgg gccaggccgg ggagatgctg acagtcatgc tagtatgaag   3180
agtctgctga ccagcaggcc tgaggacacc acacacaatc gccgcagcag aggcatggtc   3240
cagagcagct ccccaatcat gcccacagtg gggccctcca ctgcatcccc agaagaaccc   3300
```

-continued

| | |
|---|---|
| ccaggctcca gtttacccag tgatacatca gatgagatca tggaccttct ggtgcagtca | 3360 |
| gtgaccaaga gcagtcctcg tgccttagct gctagggaac gcaagcgttc ccgcggcaac | 3420 |
| cgcaagtctt tgagaaggac gttgaagagt gggctcggag atgacctggt gcaggcactg | 3480 |
| ggactaagca agggtcctgg cctggaggtg tgaaggtgct gtatcccgga atctatctg | 3540 |
| gaccctggac tgcagtgcag agatgacag agtgaggagg gcccagagca gaattctggc | 3600 |
| cccagaactc tgtgcccagg agccatgcct tgagcagtat tagccgtgtg tgtatgcatg | 3660 |
| tgagtgtgtg tgtatgtgtg tgtgtgcatg catatgcatg tgcatgtgtg tgagctcctt | 3720 |
| gaacgcacgg agcaaaataa aattttctta gctaatccaa aaaaaaaaa aaaaa | 3775 |

<210> SEQ ID NO 25
<211> LENGTH: 3799
<212> TYPE: DNA
<213> ORGANISM: Homo sapiens

<400> SEQUENCE: 25

| | |
|---|---|
| tgagccggcc gcagagccat ggcgggcggg aagaccgcg gggacggaga gccggtatca | 60 |
| gtggtgaccg tgagggtgca gtacctggaa gacaccgacc ccttcgcatg tgccaacttt | 120 |
| ccggagccgc gccgggcccc cacctgcagc ctggacgggg cgctgccctt gggcgcgcag | 180 |
| atacccgcgg tgcaccgcct gctgggagcg ccgctcaagt tggaggattg tgctctgcaa | 240 |
| gtgtctccct ccggatacta cctggacacc gagctgtccc tggaagagca gcggagatg | 300 |
| ctggagggct tctatgaaga gatcagcaaa gggcggaagc ccacgctgat ccttcggacc | 360 |
| cagctctctg tgagggtcaa cgctatcttg gaaaagctgt atagctccag tggtcctgag | 420 |
| ctccgccgct ccctcttctc actgaagcag atcttccagg aggacaaaga cctggtgcct | 480 |
| gaatttgtgc attcagaggg gctgagctgc ctgatccgtg tgggtgctgc tgccgaccac | 540 |
| aactaccaga gctacatcct tagagcgctc ggccagctga tgctctttgt ggatggaatg | 600 |
| ctggggtgg tggcccacag tgacactatt cagtggctgt acacattgtg tgccagcctg | 660 |
| tcccgcttgg tggtgaagac agccctgaag ctgctgttgg tgtttgtaga atactccgaa | 720 |
| aacaacgcac cgctgttcat ccgtgcagtg aactctgtgg ccagcaccac cggtgctcct | 780 |
| ccctgggcca atctggtgtc catcctggag gagaagaatg cgctgaccc tgagttgttg | 840 |
| gtgtacacgg tcaccctcat caacaagacg ctggcggcgc tccggaccca ggactccttc | 900 |
| tacgatgtga cggatgcact ggagcagcag ggcatggaag cgctggtcca cgccacctg | 960 |
| ggcactgcgg gcactgacgt cgacctgcgc acgcagcttg tgctctacga gaacgccctg | 1020 |
| aaattggagg atgagacat cgaagaagcc ccaggcgctg gtgggcggcg ggaacgacga | 1080 |
| aagccttctt ctgaggaggg caagaggagc cgccgttctc tggaaggcgg gggctgcccc | 1140 |
| gcgcgtgccc cggaacctgg ccccacaggc ccgcctcac cggtaggccc cacctcttcc | 1200 |
| accggccccg ccctgctgac aggccccgcc tccagccctg tgggccctcc ctccggtctc | 1260 |
| caagcttcag tgaaccttt tcctaccatc tctgtggcac cctcagctga cacctccagc | 1320 |
| gagaggagca tctacaaact tcaccaaact gcttccgttt gagcccggtt cctggagaat | 1380 |
| gtggcggcag cagaaacaga gaagcaggtt gcgctggccc agggccgggc agagacactt | 1440 |
| gccgggggcca tgcccaatga ggcgggtgga cacccagatg cccggcaact ctgggactcc | 1500 |
| ccagagacag cccctgcagc cagaacaccc cagagccctg cccctgtgt cctgctccgg | 1560 |
| gcccagcgaa gccttgcacc agagcccaag gagccactga taccagcaag ccccaaggct | 1620 |

-continued

```
gagcccatct gggagctccc tacccgtgca cccaggctct ctattgggga cctggacttt    1680
tcagatctag gggaggatga agaccaggac atgctgaatg tagagtctgt ggaggctggg    1740
aaagacatcc cagctccctc accccactg cccctgctct cgggagtacc cccccctccc    1800
ccacttccac ctcccccacc catcaaaggc cccttcccac cacctccacc tctacctctg    1860
gctgccccctc ttccccattc agtgcctgac agctcagccc tccccactaa gaggaagaca    1920
gtaaaactt tctggcgtga gctgaagctg gctgggggcc atggagtctc tgcaagccgc    1980
tttgggccct cgccacccct ctgggcttca ctggaccctg tctcagtgga cacggcccga    2040
ctggaacacc tctttgagtc tcgtgccaaa gaggtgctgc cctccaagaa agctggagag    2100
ggccgccgga caatgaccac agtgctggac cccaagcgca gcaacgccat caacatcggc    2160
ctaaccacac tgccacctgt gcatgtcatt aaggctgctc tgctcaactt tgatgagttt    2220
gctgtcagca aggatggcat tgagaagcta ctgaccatga tgcccacgga ggaagagcgg    2280
cagaagattg aggaagccca gctggccaac cctgacatac ccctgggccc agccgagaac    2340
ttcctgatga ctcttgcctc cattggcggc ctcgctgctc gtctacaact ctgggccttc    2400
aagctggact atgacagcat ggagcgggaa attgctgagc cactgttttga cctgaaagtg    2460
ggtatggaac agctggtaca gaatgccacc ttccgctgca tcctggctac cctcctagcg    2520
gtgggcaact tcctcaatgg ctcccagagc agcggctttg agctgagcta cctggagaag    2580
gtgtcagagg tgaaggacac ggtgcgtcga cagtcactgc tacaccatct ctgctcccta    2640
gtgctccaga cccggcctga gtcctctgac ctctattcag aaatccctgc cctgacccgc    2700
tgtgccaagg tggactttga acagctgact gagaacctgg ggcagctgga gcgccggagc    2760
cgggcagccg aggagagcct gcggagcttg gccaagcatg agctggcccc agccctgcgt    2820
gcccgcctca cccacttcct ggaccagtgt gcccgccgtg ttgccatgct aaggatagtg    2880
caccgccgtg tctgcaatag gttccatgcc ttcctgctct acctgggcta caccccgcag    2940
gcggcccgtg aagtgcgcat catgcagttc tgccacacgc tgcgggaatt tgcgcttgag    3000
tatcggactt gccgggaacg agtgctacag cagcagcaga agcaggccac ataccgtgag    3060
cgcaacaaga cccggggacg catgatcacc gagacagaga agttctcagg tgtggctggg    3120
gaagccccca gcaaccccct tgtcccagta gcagtgagca gcgggccagg ccggggagat    3180
gctgacagtc atgctagtat gaagagtctg ctgaccagca ggcctgagga caccacacac    3240
aatcgccgca gcagaggcat ggtccagagc agctccccaa tcatgcccac agtggggccc    3300
tccactgcat ccccagaaga accccaggc tccagtttac ccagtgatac atcagatgag    3360
atcatggacc ttctggtgca gtcagtgacc aagagcagtc ctcgtgcctt agctgctagg    3420
gaacgcaagc gttcccgcgg caaccgcaag tctttgagaa ggacgttgaa gagtgggctc    3480
ggagatgacc tggtgcaggc actgggacta agcaagggtc ctggcctgga ggtgtgaagg    3540
tgctgtatcc cggaaatcta tctggaccct ggactgcagt gcaggagatg acagagtgag    3600
gagggcccag agcagaattc tggccccaga actctgtgcc caggagccat gccttgagca    3660
gtattagccg tgtgtgtatg catgtgagtg tgtgtgtatg tgtgtgtgtg catgcatatg    3720
catgtgcatg tgtgtgagct ccttgaacgc acggagcaaa ataaaatttt cttagctaat    3780
ccaaaaaaaa aaaaaaaa                                                   3799
```

<210> SEQ ID NO 26
<211> LENGTH: 3636
<212> TYPE: DNA
<213> ORGANISM: Mus sp.

<400> SEQUENCE: 26

```
tgaagttgca gcatttgcag gggacacaag aggcgtccag cggtagccgg tggcagagcc        60
atggcgggcg aggaagagcg cggggatggg gacccagtat ccgtggtaac tgtgagagtg       120
cagtacctgg aagacaccga ccctttcgct tgtgccaact tcccggaacc acgccgggcc       180
cccacctgca gcctggacgg ggctctgccc ctgagtgcgc agatccctgc tctgcaccga       240
ctcctggggg cgcctcttaa gctggaggac tgtgcattgc aagtgtctcc ctccggatac       300
tacctggacc cggagctgtc cctagaagaa cagcgggaga tgctggaggg tttctatgaa       360
gagatcagca aagggcggaa gcccacgtta atcctgcgga cccagctctc cgtgagggtc       420
aatgctatct tggaaaagct gtatggctcc agtggcccg agctccgccg atctctcttc        480
tcattaaagc agatattcca ggaagacaag gacctggtgc ccgaattcgt gcactcggag       540
ggtctgagtt gcctgatccg cgtgggtgct gctgcagacc acaactacca gagctacatc       600
cttcgagccc tgggccagct gatgctgttt gtggatggga tgctgggggt ggtggcccac       660
agcgagaccg tgcagtggct gtataccctg tgtgctagcc tgtcccgctt ggtggtaaag       720
acagccctga gctgctgct ggtgtttgtg gagtattccg agaacaacgc gccgctgttc        780
atccaggcag tcaacgcagt agccagtgcc accggtactc ttccctgggc caacttggtg       840
tccatcctgg aggagaagaa tggagctgat gcagagttgt tggtgtacac tgtcactctc       900
attaacaaga cgctggcggc actcccagac caggactcct tctatgatgt gacagatgct       960
ctggagcagc agggcatgga agcgctggtc caacgtttct tgggcaccgc tggcactgat      1020
gttgacctgc gaacccagct aacgctctat gagagtgccc ttcggttaga ggatggagat      1080
atggaagagg ctgcagccgc cgctgctgca ggtggccggc gagagcggcg gaagccatcc      1140
tcggaggagg gcaaaaggag ccgaagatca ctagaaggtg gaggctgccc tgtgcgtgcc      1200
ccagaacctg gctctacagg ctccgcctca ccagtaggct ccaccccctc cactggctcc      1260
gccccgccta caaatccagc cttcagctct actggcccag cctctggcct tcttcgaacc      1320
tcagtgaacc tctttcctac catttccgtg gggccgtcag tggacagttc ctgtgagaga      1380
agcgtctaca aacttcacca aactgctccc gtttgctccc ctgagagtcc acctgtcccc      1440
cagtcccttc ctgggcaggc caggctagaa gcccggttcc tggagaatgt ggcggcagca      1500
gagacggaga agcaggctgc tctggcccaa ggccgagcgg agacgctggc tggagccacg      1560
gtagatgaca ctgatggatc atcaggcaca agggaactgt gggactcccc agagccagcc      1620
tctgcaccca ggacaccca gagccctgtt cccgaatcc tgctgcgcac ccagcggagt        1680
cttgagccag agcccaagaa gccagtgtca ccaccaagcc ctaaggctga gcctatccag      1740
gagcctccca cctgtgtccc caagctctgc attggggact tggacttctc agacctaggg      1800
gaggatgaag accaggacac actgaatgtg gaatctgtgg aggctggaaa agcatctccc      1860
ttcctgtcat ctctatcgcc ctcactctct gggggtcccc ctcctccgcc ccacctcct       1920
ccacccatca caggctcctg cccaccgcct ccacccctgg ctgctccttt tacccactca      1980
gcacttgacg gcccaaggca ccccaccaaa aggaagacag taaaactttt ctggcgggaa      2040
ctaaagctga ctgggggccc tgggtgctct agaagccgct ttgggccttg tcctaccctg      2100
tgggcctcgc tggaacccgt ctcggtggac acagcccgc tggaacacct atttgagtcc       2160
agagccaagg atgtgctacc aaccaagaaa gctggtgagg gccgccggac aatgaccgta      2220
gtgctggacc ccaagcgcag caatgccatc aacattggcc taaccactct gccacccgtg      2280
```

```
cacgtcatca aggctgccct gctcaacttc gatgagtttg ctgtcagcaa agatggcatt    2340
gagaaactgc tgacaatgat gcccacggag gaagagcggc agaagattga ggaagcccag    2400
ctggctaacc ccgatgtacc cctcggcccc gctgagaatt tcctgatgac gcttgcttcc    2460
attggaggcc tggctgcgcg cctacagctc tgggctttca agctggacta tgaaagcatg    2520
gagcgggaaa ttgcagagcc actgtttgat ctgaaagtgg gcatggaaca gctggtacac    2580
aatgccacct tccgctgtat tctggctacc cttttggctg tgggcaactt cctcaatggt    2640
tcccagagca gtggctttga gctgagctac ctggagaagg tgtcagaagt gaaggacaca    2700
gtgcgacggc agtcattgct ctatcatctc tgctccctgg tgctccagac ccgacctgat    2760
tcctctgacc tctactcaga aattcctgcc ctcacccgct gtgccaaggt ggactttgaa    2820
cagctgactg agaacctagg gcagctggag tgccggagcc aggctgccga ggacagcctc    2880
cggagcttgg ctaagcacga gctctcccca gctctgcgtg ctcgcctcac ccacttcttg    2940
gcccagtgta cccgccgggt agccatgtta agagtagtgc atcgccgagt ctgcaatagg    3000
ttccatgcct tcctgctcta cctgggctac accccacagg cagcaaggga tgtacgcatc    3060
atgcagttct gccacacact gagagagttt gcccttgagt atcggacttg tcgggaacgg    3120
gtactgcagc agcagcagaa gcgggctaca taccgtgagc gcaacaagac ccgtggtcgc    3180
atgattaccg agacagagaa gttctcaggt gtggctgggg aggcccccaa taacctgtct    3240
gtcccagtgg ctgtgggcag cgggccaggt cagggtgata ctgacaatca tgccagcatg    3300
aagagcctgc ttaccagcag gccggaagat gccacacaca gccgacgcag cagaggtatg    3360
gtccagagca gttcccccgt ctcacacaca gcagtggggc cctccgctgc atcccctgag    3420
gagactgcag cctccggctt acccaccgac acgtcagatg agataatgga cctgctggtg    3480
cagtcagtta ccaagagcgg tcctagagcc ttagctgctc gggagaggaa gcgctctcgt    3540
ggcaaccgaa agtccttgag acggacactg aagagtggac ttggagatga cctggtgcag    3600
gcactgggac taagcaaagc tcctggtcta gaggtg                               3636

<210> SEQ ID NO 27
<211> LENGTH: 3558
<212> TYPE: DNA
<213> ORGANISM: Mus sp.

<400> SEQUENCE: 27
tgaagttgca gcatttgcag gggacacaag aggcgtccag cggtagccgg tggcagagcc      60
atggcgggcg aggaagagcg cggggatggg gacccagtat ccgtggtaac tgtgagagtg     120
cagtacctgg aagacaccga ccctttcgct tgtgccaact tcccggaacc acgccgggcc     180
cccacctgca gcctggacgg ggctctgccc ctgagtgcgc agatccctgc tctgcaccga     240
ctcctggggg cgcctcttaa gctggaggac tgtgcattgc aagtgtctcc ctccggatac     300
tacctggacc cggagctgtc cctagaagaa cagcgggaga tgctggaggg tttctatgaa     360
gagatcagca aagggcggaa gcccacgtta atcctgcgga cccagctctc cgtgagggtc     420
aatgctatct tggaaaagct gtatggctcc agtggcccca gctccgccga atctctcttc     480
tcattaaagc agatattcca ggaagacaag gacctggtgc ccgaattcgt gcactcggag     540
ggtctgagtt gcctgatccg cgtgggtgct gctgcagacc acaactacca gagctacatc     600
cttcgagccc tgggccagct gatgctgttt gtggatggga tgctgggggt ggtggcccac     660
agcgagaccg tgcagtggct gtatacccctg tgtgctagcc tgtcccgctt ggtggtaaag     720
acagccctga agctgctgct ggtgtttgtg gagtattccg agaacaacgc gccgctgttc     780
```

-continued

```
atccaggcag tcaacgcagt agccagtgcc accggtactc ttccctgggc caacttggtg       840
tccatcctgg aggagaagaa tggagctgat gcagagttgt tggtgtacac tgtcactctc       900
attaacaaga cgctggcggc actcccagac caggactcct tctatgatgt gacagatgct       960
ctggagcagc agggcatgga agcgctggtc aacgtttct tgggcaccgc tggcactgat       1020
gttgacctgc gaacccagct aacgctctat gagagtgccc ttcggttaga ggatggagat       1080
atggaagagg ctgcagccgc cgctgctgca gtggccggc gagagcggcg aagccatcc        1140
tcggaggagg gcaaaaggag ccgaagatca ctagaaggtg gaggctgccc tgtgcgtgcc       1200
ccagaacctg gctctacagg ctccgcctca ccagtaggct ccacccctc cactggctcc        1260
gcccgcccta caaatccagc cttcagtctc actggcccag cctctggcct tcttcgaacc       1320
tcagtgaacc tctttcctac catttccgtg gggccgtcag tggacagttc ctgtgagaga       1380
agcgtctaca aagcccggtt cctggagaat gtggcggcag cagagacgga gaagcaggct       1440
gctctggccc aaggccgagc ggagacgctg gctggagcca cggtagatga cactgatgga       1500
tcatcaggca aaggggaact gtgggactcc ccagagccag cctctgcacc caggacaccc       1560
cagagccctg tttcccgaat cctgctgcgc acccagcgga gtcttgagcc agagcccaag       1620
aagccagtgt caccaccaag ccctaaggct gagcctatcc aggagcctcc cacctgtgtc       1680
cccaagctct gcattgggga cttggacttc tcagacctag ggaggatga agaccaggac       1740
acactgaatg tggaatctgt ggaggctgga aaagcatctc ccttcctgtc atctctatcg       1800
ccctcactct ctgggggtcc ccctcctccg ccccacctc ctccacccat acaggctcc        1860
tgcccaccgc ctccacccct ggctgctcct tttacccact cagcacttga cggcccaagg       1920
caccccacca aaaggaagac agtaaaactt tctggcgggg aactaaagct gactgggggc       1980
cctgggtgct ctagaagccg ctttgggcct tgtcctaccc tgtgggcctc gctggaaccc       2040
gtctcggtgg acacagcccg cctggaacac ctatttgagt ccagagccaa ggatgtgcta       2100
ccaaccaaga agctggtga gggccgccgg acaatgaccg tagtgctgga ccccaagcgc       2160
agcaatgcca tcaacattgg cctaaccact ctgccaccg tgcacgtcat caaggctgcc       2220
ctgctcaact tcgatgagtt tgctgtcagc aaagatggca ttgagaaact gctgacaatg       2280
atgcccacgg aggaagagcg gcagaagatt gaggaagccc agctggctaa ccccgatgta       2340
cccctcggcc ccgctgagaa tttcctgatg acgcttgctt ccattggagg cctggctgcg       2400
cgcctacagc tctgggcttt caagctggac tatgaaagca tggagcggga aattgcagag       2460
ccactgtttg atctgaaagt gggcatggaa cagctggtac acaatgccac cttccgctgt       2520
attctggcta ccctttttggc tgtgggcaac ttcctcaatg gttcccagag cagtggcttt       2580
gagctgagct acctggagaa ggtgtcagaa gtgaaggaca cagtgcgacg gcagtcattg       2640
ctctatcatc tctgctccct ggtgctccag acccgacctg attcctctga cctctactca       2700
gaaattcctg ccctcacccg ctgtgccaag gtggactttg aacagctgac tgagaaccta       2760
gggcagctgg agtgccggag ccaggctgcc gaggacagcc tccggagctt ggctaagcac       2820
gagctctccc cagctctgcg tgctcgcctc acccacttct ggcccagtg tacccgccgg       2880
gtagccatgt taagagtagt gcatcgccga gtctgcaata ggttccatgc cttcctgctc       2940
tacctgggct acacccccaca ggcagcaagg gatgtacgca tcatgcagtt ctgccacaca       3000
ctgagagagt ttgcccttga gtatcggact tgtcgggaac gggtactgca gcagcagcag       3060
aagcgggcta cataccgtga gcgcaacaag acccgtggtc gcatgattac cgagacagag       3120
```

| aagttctcag gtgtggctgg ggaggccccc aataacctgt ctgtcccagt ggctgtgggc | 3180 |
| agcgggccag gtcagggtga tactgacaat catgccagca tgaagagcct gcttaccagc | 3240 |
| aggccggaag atgccacaca cagccgacgc agcagaggta tggtccagag cagttccccc | 3300 |
| gtctcacaca cagcagtggg gccctccgct gcatcccctg aggagactgc agcctccggc | 3360 |
| ttacccaccg acacgtcaga tgagataatg gacctgctgg tgcagtcagt taccaagagc | 3420 |
| ggtcctagag ccttagctgc tcgggagagg aagcgctctc gtggcaaccg aaagtccttg | 3480 |
| agacggacac tgaagagtgg acttggagat gacctggtgc aggcactggg actaagcaaa | 3540 |
| gctcctggtc tagaggtg | 3558 |

```
<210> SEQ ID NO 28
<211> LENGTH: 140
<212> TYPE: PRT
<213> ORGANISM: Homo sapiens

<400> SEQUENCE: 28

Met Ala Gly Trp Gln Ser Tyr Val Asp Asn Leu Met Cys Asp Gly Cys
  1               5                  10                  15

Cys Gln Glu Ala Ala Ile Val Gly Tyr Cys Asp Ala Lys Tyr Val Trp
             20                  25                  30

Ala Ala Thr Ala Gly Gly Val Phe Gln Ser Ile Thr Pro Ile Glu Ile
         35                  40                  45

Asp Met Ile Val Gly Lys Asp Arg Glu Gly Phe Phe Thr Asn Gly Leu
     50                  55                  60

Thr Leu Gly Ala Lys Lys Cys Ser Val Ile Arg Asp Ser Leu Tyr Val
 65                  70                  75                  80

Asp Gly Asp Cys Thr Met Asp Ile Arg Thr Lys Ser Gln Gly Gly Glu
                 85                  90                  95

Pro Thr Tyr Asn Val Ala Val Gly Arg Ala Gly Arg Val Leu Val Phe
            100                 105                 110

Val Met Gly Lys Glu Gly Val His Gly Gly Leu Asn Lys Lys Ala
        115                 120                 125

Tyr Ser Met Ala Lys Tyr Leu Arg Asp Ser Gly Phe
    130                 135                 140

<210> SEQ ID NO 29
<211> LENGTH: 420
<212> TYPE: DNA
<213> ORGANISM: Homo sapiens

<400> SEQUENCE: 29
```

| atggccggtt gggagagcta cgtggataac ctgatgtgcg atggctgctg ccaggaggcc | 60 |
| gccattgtcg gctactgcga cgccaaatac gtctgggcag ccacggccgg gggcgtcttt | 120 |
| cagagcatta cgccaataga aatagatatg attgtaggaa agaccgggga aggtttcttt | 180 |
| accaacggtt tgactcttgg cgcgaagaaa tgctcagtga tcagagatag tctatacgtc | 240 |
| gatggtgact gcacaatgga catccggaca aagagtcaag gtggggagcc aacatacaat | 300 |
| gtggctgtcg gcagagctgg tagagtcttg gtctttgtaa tgggaaaaga aggggtccat | 360 |
| ggaggcggat tgaataagaa ggcatactca atggcaaaat acttgagaga ctctgggttc | 420 |

```
<210> SEQ ID NO 30
<211> LENGTH: 420
<212> TYPE: DNA
<213> ORGANISM: Homo sapiens
```

```
<400> SEQUENCE: 30
atggccggtt ggcagagcta cgtggataac ctgatgtgcg atggctgctg ccaggaggcc      60
gccattgtcg gctactgcga cgccaaatac gtctgggcag ccacggccgg gggcgtcttt     120
cagagcatta cgccaataga aatagatatg attgtaggaa aagaccggga aggtttcttt     180
accaacggtt tgactcttgg cgcgaagaaa tgctcagtga tcagagatag tctatacgtc     240
gatggtgact gcacaatgga catccggaca aagagtcaag gtggggagcc aacatacaat     300
gtggctgtcg gcagagctgg tagagcattg gttatagtca tgggaaagga aggtgtccac     360
ggaggcacac ttaacaagaa agcatatgaa ctcgctttat acctgaggag gtctgatgtg     420
```

```
<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 31
atggccggtt ggcagagcta cgtggat                                          27
```

```
<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 32
ttacacatca gacctcctca ggtataaagc                                       30
```

```
<210> SEQ ID NO 33
<211> LENGTH: 666
<212> TYPE: PRT
<213> ORGANISM: Homo sapiens

<400> SEQUENCE: 33
```

| | | | | | | | | | | | | | | | |
|---|---|---|---|---|---|---|---|---|---|---|---|---|---|---|---|
| Met | Ala | Gly | Gly | Glu | Asp | Arg | Gly | Asp | Gly | Glu | Pro | Val | Ser | Val | Val |
| 1 | | | | 5 | | | | | 10 | | | | | 15 | |
| Thr | Val | Arg | Val | Gln | Tyr | Leu | Glu | Asp | Thr | Asp | Pro | Phe | Ala | Cys | Ala |
| | | | 20 | | | | | 25 | | | | | 30 | | |
| Asn | Phe | Pro | Glu | Pro | Arg | Arg | Ala | Pro | Thr | Cys | Ser | Leu | Asp | Gly | Ala |
| | | 35 | | | | | 40 | | | | | 45 | | | |
| Leu | Pro | Leu | Gly | Ala | Gln | Ile | Pro | Ala | Val | His | Arg | Leu | Leu | Gly | Ala |
| | 50 | | | | | 55 | | | | | 60 | | | | |
| Pro | Leu | Lys | Leu | Glu | Asp | Cys | Ala | Leu | Gln | Val | Ser | Pro | Ser | Gly | Tyr |
| 65 | | | | | 70 | | | | | 75 | | | | | 80 |
| Tyr | Leu | Asp | Thr | Glu | Leu | Ser | Leu | Glu | Glu | Gln | Arg | Glu | Met | Leu | Glu |
| | | | | 85 | | | | | 90 | | | | | 95 | |
| Gly | Phe | Tyr | Glu | Glu | Ile | Ser | Lys | Gly | Arg | Lys | Pro | Thr | Leu | Ile | Leu |
| | | | 100 | | | | | 105 | | | | | 110 | | |
| Arg | Thr | Gln | Leu | Ser | Val | Arg | Val | Asn | Ala | Ile | Leu | Glu | Lys | Leu | Tyr |
| | | | 115 | | | | | 120 | | | | | 125 | | |
| Ser | Ser | Ser | Gly | Pro | Glu | Leu | Arg | Arg | Ser | Leu | Phe | Ser | Leu | Lys | Gln |
| | 130 | | | | | 135 | | | | | 140 | | | | |
| Ile | Phe | Gln | Glu | Asp | Lys | Asp | Leu | Val | Pro | Glu | Phe | Val | His | Ser | Glu |
| 145 | | | | | 150 | | | | | 155 | | | | | 160 |

-continued

```
Gly Leu Ser Cys Leu Ile Arg Val Gly Ala Ala Asp His Asn Tyr
                165                 170                 175
Gln Ser Tyr Ile Leu Arg Ala Leu Gly Gln Leu Met Leu Phe Val Asp
            180                 185                 190
Gly Met Leu Gly Val Val Ala His Ser Asp Thr Ile Gln Trp Leu Tyr
            195                 200                 205
Thr Leu Cys Ala Ser Leu Ser Arg Leu Val Val Lys Thr Ala Leu Lys
        210                 215                 220
Leu Leu Leu Val Phe Val Glu Tyr Ser Glu Asn Asn Ala Pro Leu Phe
225                 230                 235                 240
Ile Arg Ala Val Asn Ser Val Ala Ser Thr Thr Gly Ala Pro Pro Trp
                245                 250                 255
Ala Asn Leu Val Ser Ile Leu Glu Glu Lys Asn Gly Ala Asp Pro Glu
            260                 265                 270
Leu Leu Val Tyr Thr Val Thr Leu Ile Asn Lys Thr Leu Ala Ala Leu
            275                 280                 285
Pro Asp Gln Asp Ser Phe Tyr Asp Val Thr Asp Ala Leu Glu Gln Gln
290                 295                 300
Gly Met Glu Ala Leu Val Gln Arg His Leu Gly Thr Ala Gly Thr Asp
305                 310                 315                 320
Val Asp Leu Arg Thr Gln Leu Val Leu Tyr Glu Asn Ala Leu Lys Leu
                325                 330                 335
Glu Asp Gly Asp Ile Glu Glu Ala Pro Gly Ala Gly Gly Arg Arg Glu
            340                 345                 350
Arg Arg Lys Pro Ser Ser Glu Glu Gly Lys Arg Ser Arg Arg Ser Leu
        355                 360                 365
Glu Gly Gly Gly Cys Pro Ala Arg Ala Pro Glu Pro Gly Pro Thr Gly
            370                 375                 380
Pro Ala Ser Pro Val Gly Pro Thr Ser Ser Thr Gly Pro Ala Leu Leu
385                 390                 395                 400
Thr Gly Pro Ala Ser Ser Pro Val Gly Pro Pro Ser Gly Leu Gln Ala
                405                 410                 415
Ser Val Asn Leu Phe Pro Thr Ile Ser Val Ala Pro Ser Ala Asp Thr
            420                 425                 430
Ser Ser Glu Arg Ser Ile Tyr Lys Leu His Gln Thr Ala Ser Val Trp
        435                 440                 445
Ala Pro Glu Ser Pro Val Pro Gln Ser Pro Pro Gly Gln Ala Arg
    450                 455                 460
Leu Glu Ala Arg Phe Leu Glu Asn Val Ala Ala Ala Glu Thr Glu Lys
465                 470                 475                 480
Gln Val Ala Leu Ala Gln Gly Arg Ala Glu Thr Leu Ala Gly Ala Met
                485                 490                 495
Pro Asn Glu Ala Gly His Pro Asp Ala Arg Gln Leu Trp Asp Ser
            500                 505                 510
Pro Glu Thr Ala Pro Ala Ala Arg Thr Pro Gln Ser Pro Ala Pro Cys
        515                 520                 525
Val Leu Leu Arg Ala Gln Arg Ser Leu Ala Pro Glu Pro Lys Glu Pro
530                 535                 540
Leu Ile Pro Ala Ser Pro Lys Ala Glu Pro Ile Trp Glu Leu Pro Thr
545                 550                 555                 560
Arg Ala Pro Arg Leu Ser Ile Gly Asp Leu Asp Phe Ser Asp Leu Gly
                565                 570                 575
```

-continued

```
Glu Asp Glu Asp Gln Asp Met Leu Asn Val Glu Ser Val Glu Ala Gly
            580                 585                 590

Lys Asp Ile Pro Ala Pro Ser Pro Pro Leu Pro Leu Leu Ser Gly Val
        595                 600                 605

Pro Pro Pro Pro Leu Pro Pro Pro Pro Ile Lys Gly Pro Phe
    610                 615                 620

Pro Pro Pro Pro Leu Pro Leu Ala Ala Pro Leu Pro His Ser Val
625                 630                 635                 640

Pro Asp Ser Ser Ala Leu Pro Thr Lys Arg Lys Thr Val Lys Leu Phe
                645                 650                 655

Trp Arg Glu Leu Lys Leu Ala Gly Gly His
            660                 665
```

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 34
agctcctggt ctagaggtgt ga                                        22

<210> SEQ ID NO 35
<211> LENGTH: 1164
<212> TYPE: PRT
<213> ORGANISM: Homo sapiens

<400> SEQUENCE: 35

```
Met Ala Gly Gly Glu Asp Arg Gly Asp Gly Pro Val Ser Val Val
 1               5                  10                  15

Thr Val Arg Val Gln Tyr Leu Glu Asp Thr Asp Pro Phe Ala Cys Ala
             20                  25                  30

Asn Phe Pro Glu Pro Arg Arg Ala Pro Thr Cys Ser Leu Asp Gly Ala
         35                  40                  45

Leu Pro Leu Gly Ala Gln Ile Pro Ala Val His Arg Leu Leu Gly Ala
     50                  55                  60

Pro Leu Lys Leu Glu Asp Cys Ala Leu Gln Val Ser Pro Ser Gly Tyr
 65                  70                  75                  80

Tyr Leu Asp Thr Glu Leu Ser Leu Glu Glu Gln Arg Glu Met Leu Glu
                 85                  90                  95

Gly Phe Tyr Glu Glu Ile Ser Lys Gly Arg Lys Pro Thr Leu Ile Leu
            100                 105                 110

Arg Thr Gln Leu Ser Val Arg Val Asn Ala Ile Leu Glu Lys Leu Tyr
        115                 120                 125

Ser Ser Ser Gly Pro Glu Leu Arg Arg Ser Leu Phe Ser Leu Lys Gln
    130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Asp Thr Ile Gln Trp Leu Tyr
        195                 200                 205
```

```
Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Arg Ala Val Asn Ser Val Ala Thr Thr Thr Gly Ala Pro Pro Trp
                245                 250                 255

Ala Asn Leu Val Ser Ile Leu Glu Glu Lys Asn Gly Ala Asp Pro Glu
                260                 265                 270

Leu Leu Val Tyr Thr Val Thr Leu Ile Asn Lys Thr Leu Ala Ala Leu
                275                 280                 285

Pro Asp Gln Asp Ser Phe Tyr Asp Val Thr Asp Ala Leu Glu Gln Gln
290                 295                 300

Gly Met Asp Thr Leu Val Gln Arg His Leu Gly Thr Ala Gly Thr Asp
305                 310                 315                 320

Val Asp Leu Arg Thr Gln Leu Val Leu Tyr Glu Asn Ala Leu Lys Leu
                325                 330                 335

Glu Asp Gly Asp Ile Glu Glu Ala Pro Gly Ala Gly Gly Arg Arg Glu
                340                 345                 350

Arg Arg Lys Pro Ser Ser Glu Glu Gly Lys Arg Ser Arg Arg Ser Leu
                355                 360                 365

Glu Gly Gly Gly Cys Pro Ala Arg Ala Pro Glu Pro Gly Pro Thr Gly
                370                 375                 380

Pro Ala Ser Pro Val Gly Pro Thr Ser Ser Thr Gly Pro Ala Leu Leu
385                 390                 395                 400

Thr Gly Pro Ala Ser Ser Pro Val Gly Pro Pro Ser Gly Leu Gln Ala
                405                 410                 415

Ser Val Asn Leu Phe Pro Thr Ile Ser Val Ala Pro Ser Ala Asp Thr
                420                 425                 430

Ser Ser Glu Arg Ser Ile Tyr Lys Ala Arg Phe Leu Glu Asn Val Ala
                435                 440                 445

Ala Ala Glu Thr Glu Lys Gln Val Ala Leu Ala Gln Gly Arg Ala Glu
450                 455                 460

Thr Leu Ala Gly Ala Met Pro Asn Glu Ala Gly Gly His Pro Asp Ala
465                 470                 475                 480

Arg Gln Leu Trp Asp Ser Pro Glu Thr Ala Pro Ala Ala Arg Thr Pro
                485                 490                 495

Gln Ser Pro Ala Pro Cys Val Leu Leu Arg Ala Gln Arg Ser Leu Ala
                500                 505                 510

Pro Glu Pro Lys Glu Pro Leu Ile Pro Ala Ser Pro Lys Ala Glu Pro
                515                 520                 525

Ile Trp Glu Leu Pro Thr Arg Ala Pro Arg Leu Ser Ile Gly Asp Leu
                530                 535                 540

Asp Phe Ser Asp Leu Gly Glu Asp Glu Asp Gln Asp Met Leu Asn Val
545                 550                 555                 560

Glu Ser Val Glu Ala Gly Lys Asp Ile Pro Ala Pro Ser Pro Pro Leu
                565                 570                 575

Pro Leu Leu Ser Gly Val Pro Pro Pro Leu Pro Pro Pro Pro
                580                 585                 590

Pro Ile Lys Gly Pro Phe Pro Pro Pro Pro Leu Pro Leu Ala Ala
                595                 600                 605

Pro Leu Pro His Ser Val Pro Asp Ser Ser Ala Leu Pro Thr Lys Arg
610                 615                 620
```

-continued

```
Lys Thr Val Lys Leu Phe Trp Arg Asp Val Lys Leu Ala Gly Gly His
625                 630                 635                 640

Gly Val Ser Ala Ser Arg Phe Gly Pro Cys Ala Thr Leu Trp Ala Ser
                645                 650                 655

Leu Asp Pro Val Ser Val Asp Thr Ala Arg Leu Glu His Leu Phe Glu
            660                 665                 670

Ser Arg Ala Lys Glu Val Leu Pro Ser Lys Lys Ala Gly Glu Gly Arg
        675                 680                 685

Arg Thr Met Thr Thr Val Leu Asp Pro Lys Arg Thr Asn Ala Ile Asn
690                 695                 700

Ile Gly Leu Thr Thr Leu Pro Pro Val His Val Ile Lys Ala Ala Leu
705                 710                 715                 720

Leu Asn Phe Asp Glu Phe Ala Val Ser Lys Asp Gly Ile Glu Lys Leu
                725                 730                 735

Leu Thr Met Met Pro Thr Glu Glu Arg Gln Lys Ile Glu Gly Ala
                740                 745                 750

Gln Leu Ala Asn Pro Asp Ile Pro Leu Gly Pro Ala Glu Asn Phe Leu
        755                 760                 765

Met Thr Leu Ala Ser Ile Gly Gly Leu Ala Ala Arg Leu Gln Leu Trp
770                 775                 780

Ala Phe Lys Leu Asp Tyr Asp Ser Met Glu Arg Glu Ile Ala Glu Pro
785                 790                 795                 800

Leu Phe Asp Leu Lys Val Gly Met Glu Gln Leu Val Gln Asn Ala Thr
                805                 810                 815

Phe Arg Cys Ile Leu Ala Thr Leu Leu Ala Val Gly Asn Phe Leu Asn
            820                 825                 830

Gly Ser Gln Ser Ser Gly Phe Glu Leu Ser Tyr Leu Glu Lys Val Ser
        835                 840                 845

Asp Val Lys Asp Thr Val Arg Arg Gln Ser Leu Leu His His Leu Cys
850                 855                 860

Ser Leu Val Leu Gln Thr Arg Pro Glu Ser Ser Asp Leu Tyr Ser Glu
865                 870                 875                 880

Ile Pro Ala Leu Thr Arg Cys Ala Lys Val Asp Phe Glu Gln Leu Thr
                885                 890                 895

Glu Asn Leu Gly Gln Leu Glu Arg Arg Ser Arg Ala Ala Glu Glu Ser
            900                 905                 910

Leu Arg Ser Leu Ala Lys His Glu Leu Ala Pro Ala Leu Arg Ala Arg
        915                 920                 925

Leu Thr His Phe Leu Asp Gln Cys Ala Arg Arg Val Ala Met Leu Arg
930                 935                 940

Ile Val His Arg Arg Val Cys Asn Arg Phe His Ala Phe Leu Leu Tyr
945                 950                 955                 960

Leu Gly Tyr Thr Pro Gln Ala Ala Arg Glu Val Arg Ile Met Gln Phe
                965                 970                 975

Cys His Thr Leu Arg Glu Phe Ala Leu Glu Tyr Arg Thr Cys Arg Glu
            980                 985                 990

Arg Val Leu Gln Gln Gln Lys Gln Ala Thr Tyr Arg Glu Arg Asn
        995                 1000                1005

Lys Thr Arg Gly Arg Met Ile Thr Glu Thr Glu Lys Phe Ser Gly Val
    1010                1015                1020

Ala Gly Glu Ala Pro Ser Asn Pro Ser Val Pro Val Ala Val Ser Ser
1025                1030                1035                1040
```

```
Gly Pro Gly Arg Gly Asp Ala Asp Ser His Ala Ser Met Lys Ser Leu
            1045            1050                1055

Leu Thr Ser Arg Leu Glu Asp Thr Thr His Asn Arg Arg Ser Arg Gly
        1060            1065                1070

Met Val Gln Ser Ser Ser Pro Ile Met Pro Thr Val Gly Pro Ser Thr
        1075            1080                1085

Ala Ser Pro Glu Glu Pro Pro Gly Ser Ser Leu Pro Ser Asp Thr Ser
    1090            1095                1100

Asp Glu Ile Met Asp Leu Leu Val Gln Ser Val Thr Lys Ser Ser Pro
1105            1110            1115                1120

Arg Ala Leu Ala Ala Arg Glu Arg Lys Arg Ser Arg Gly Asn Arg Lys
            1125            1130                1135

Ser Leu Arg Arg Thr Leu Lys Ser Gly Leu Gly Asp Asp Leu Val Gln
            1140            1145                1150

Ala Leu Gly Leu Ser Lys Gly Pro Gly Leu Glu Val
        1155            1160
```

GENE AND USE THEREOF

CROSS-REFERENCES TO RELATED APPLICATIONS

This present application is a 35 U.S.C. §371 national stage of PCT application PCT/JP00/08985, filed Dec. 19, 2000, which in claims foreign priority to Japanese Application Serial Number 36 1679/1999, filed Dec. 20, 1999 and Japanese Application Serial Number 365176/1999, filed Dec. 22, 1999, the disclosures of which are incorporated herein by reference.

FIELD OF THE INVENTION

The present invention relates to a novel gene and use thereof. More specifically, the present invention relates to a novel insulin responsive aminopeptidase binding protein (IRAP-BP) gene and use thereof.

BACKGROUND ART

A blood sugar level is regulated by glucose uptake in the skeletal muscle and adipose tissue through the action of insulin. In diabetes mellitus, this lowered action of insulin results in maintaining a high blood sugar level, which leads to the development of diabetes mellitus. Uptake of glucose in cells requires to be mediated by a membrane protein called a glucose transporter. Currently known glucose transporters are 7 types of GLUT1 through GLUT7 (Bell et al., J. Biol. Chem., 268, 3352–3356, 1993; Olson & Pessin, Annu. Rev. Nutr., 16, 235–256, 1996). Among them, glucose transporter 4 (GLUT4), which expression is noted chiefly in the skeletal muscle and adipose tissues, is associated with the insulin-induced glucose transporting activity (Fukumoto et al., Proc. Natl. Acad. Sci. USA., 85, 5434–5438, 1988; Birnbaum et al., Cell, 57, 305–315, 1989).

GLUT4 is present normally in the intracellular vesicles called GLUT4 vesicles. When blood sugar increases, it is considered that GLUT4 would migrate into cell membranes (translocation) by the action of insulin to promote the glucose uptake (Bell et al., Diabetes Care, 13, 198–208, 1990; Czech et al., Trend. Biochem. Sci., 17, 197–201, 1992).

In order to clarify the molecular mechanism for this translocation of GLUT4 vesicles, it has been attempted to identify not only GLUT4 itself but also other proteins constituting the GLUT4 vesicles. Presently, IRAP (insulin-responsive aminopeptidase; Kandror & Pilch, Proc. Natl. Acad. Sci. USA, 91, 8017–8021, 1994, Kandror et al., J. Biol. Chem. 269, 30777–30780, 1994, Keller et al., J. Biol. Chem., 270, 23612–23618, 1995) is known as the molecule for constituting GLUT4 vesicles, in addition to VAMPs (vesicle-associated membrane proteins; Cain et al., J. Biol. Chem., 267, 11681–11634, 1992), SCAMPs (secretory component-associated membrane proteins; Thoidis et al., J. Biol. Chem., 268, 11691–11696, 1993; Laurie et al., J. Biol. chem., 268, 19110–19117, 1993), phosphatidylinositol 4-kinase (Del Vacchio & Pilch, J. Biol. Chem., 266, 13278–13283, 1991), low molecular weight GTP-bound protein Rab4 (Cormont et al., J. Biol. Chem., 268, 19491–19497, 1993), etc.

IRAP, also called gp160, is a membrane protein of one transmembrane type and localized in the GLUT4 vesicles in cells. In view of the protein structure, IRAP consists of an amino-terminal (N-terminal) 109 amino acid domain in the cytoplasm, followed by a 22 amino acid transmembrane domain and further an extracellular domain composed of a carboxy-terminal (C-terminal) 785 amino acids (Kandror & Pilch, Proc. Natl. Acad. Sci. USA, 91, 8017–8021, 1994; Keller et al., J. Biol. Chem., 270, 23612–23618, 1995). The extracellular domain is a zinc-dependent protease (aminopeptidase) and its activity has been verified (Kandror et al., J. Biol. Chem., 269, 30777–30780, 1994). A peptide corresponding to the N-terminal side domain (cytoplasmic side domain) among these domains is injected into cells to cause translocation of GLUT4 vesicles to the cell surface. It is thus predicted that an IRAP binding protein will be present to retain GLUT4 vesicles within cells (Waters et al., J. Biol. Chem., 272, 23323–23327, 1997).

The cDNA of FHOS gene and the putative amino acid sequence are also known (Westendorf et al., Gene, 232, 173–182, 1999; Genbank Accession No. AF113615). However, it has not been reported that FHOS binds to the molecules constituting GLUT4 vesicles, such as IRAP, etc.

DISCLOSURE OF THE INVENTION

The present invention provides a novel IRAP-BP, its gene, a method for screening a compound capable of reducing a blood sugar level using the same, a compound obtainable by the screening method, and so on.

In order to solve the foregoing problems, the present inventors have made extensive studies and succeeded in cloning a novel IRAP-BP gene from a human muscle skeleton-derived cDNA library, using the yeast two-hybrid method (Fields & Strenglanz, Trends Genet., 10, 286–292, 1994; Brent & Finley, Annu. Rev. Genet., 31, 663–704, 1997). As a result of further investigations, the present inventors have accomplished the present invention.

That is, the present invention relates to the following features.

(1) A protein containing the same or substantially the same amino acid sequence as the amino acid sequence represented by SEQ ID NO:1, or a salt thereof.

(2) The protein or its salt according to (1), wherein substantially the same amino acid sequence is represented by SEQ ID NO:15.

(3) A DNA containing a DNA encoding the protein according to (1).

(4) The DNA according to (3), wherein the DNA encoding the protein according to (1) is a DNA containing the base sequence represented by SEQ ID NO:3 or SEQ ID NO:16.

(5) A recombinant vector containing the DNA according to (2).

(6) A transformant transformed with the recombinant vector according to (5).

(7) A method for manufacturing the protein or its salt according to (1), which comprises culturing the transformant according to (6), producing and accumulating the protein according to (1) and collecting the same.

(8) A pharmaceutical comprising the protein or its salt according to (1) or the DNA according to (2).

(9) The pharmaceutical according to (8), which is a preventive/therapeutic agent for hypoglycemia.

(10) An antibody to the protein or its salt according to (1).

(11) A diagnostic agent comprising the antibody according to (10).

(12) A protein containing the amino acid sequence represented by SEQ ID NO:2 or SEQ ID NO:17, or a salt thereof.

(13) A DNA containing a DNA encoding the protein according to (12).

(14) The DNA according to (13), wherein the DNA encoding the protein according to (12) is a DNA containing the base sequence represented by SEQ ID NO:4 or SEQ ID NO:18.

(15) A recombinant vector containing the DNA according to (13).

(16) A transformant transformed with the recombinant vector according to (15).

(17) A method for manufacturing the protein or its salt according to (12), which comprises culturing the transformant according to (16), producing and accumulating the protein according to (12) and collecting the same.

(18) A pharmaceutical comprising the protein or its salt according to (12) or the DNA according to (13).

(19) The pharmaceutical according to (18), which is a preventive/therapeutic agent for hypoglycemia.

(20) An antibody to the protein or its salt according to (12).

(21) A diagnostic agent comprising the antibody according to (20).

(22) A method for screening a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4, which comprises using a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof.

(23) A method for screening a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4, which comprises using a cell capable of producing a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, or a partial peptide of the protein containing the same or substantially the same amino acid sequence as the amino acid sequence represented by SEQ ID NO:2.

(24) A kit for screening a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4, comprising a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof.

(25) A kit for screening a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4, comprising a cell capable of producing a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, or a partial peptide of the protein containing the same or substantially the same amino acid sequence as the amino acid sequence represented by SEQ ID NO:2.

(26) A compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4, which is obtainable using the screening method according to (22), the screening method according to (23), the screening kit according to (24) or the screening kit according to (25).

(27) A pharmaceutical comprising the compound or its salt according to (26).

(28) A prophylactic/therapeutic agent for hyperglycemia or diabetes mellitus, comprising the compound or its salt according to (26).

(29) A pharmaceutical comprising a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4.

(30) A prophylactic/therapeutic agent for hyperglycemia or diabetes mellitus comprising a compound or its salt that inhibits the binding of a protein containing the same or substantially the same amino acid sequence as the amino acid sequence represented by SEQ ID NO:1, a partial peptide of the protein containing the same or substantially the same amino acid sequence as the amino acid sequence represented by SEQ ID NO:1, a protein containing the same or substantially the same amino acid sequence as the amino acid sequence represented by SEQ ID NO:2, a partial peptide of the protein containing the same or substantially the same amino acid sequence as the amino acid sequence represented by SEQ ID NO:2, or a salt thereof, to insulin-responsive aminopeptidase or glucose transporter 4.

(31) A pharmaceutical comprising a compound or its salt that promotes or suppresses the expression of a protein containing the same or substantially the same amino acid sequence as the amino acid sequence represented by SEQ ID NO:1 or a protein containing the same or substantially the same amino acid sequence as the amino acid sequence represented by SEQ ID NO:2.

(32) A prophylactic/therapeutic agent for hyperglycemia or diabetes mellitus comprising a compound or its salt that suppresses the expression of a protein containing the same or substantially the same amino acid sequence as the amino acid sequence represented by SEQ ID NO:1 or a protein containing the same or substantially the same amino acid sequence as the amino acid sequence represented by SEQ ID NO:2.

(33) A prophylactic/therapeutic agent for hypoglycemia comprising a compound or its salt that promotes the expression of a protein containing the same or substantially the same amino acid sequence as the amino acid sequence represented by SEQ ID NO:1 or a protein containing the same or substantially the same amino acid sequence as the amino acid sequence represented by SEQ ID NO:2.

(34) Use of the protein or its salt according to (1), the DNA according to (3), the protein or its salt according to (12), or the DNA according to (13), for manufacturing the pharmaceutical comprising the protein or its salt according to (1), the DNA according to (3), the protein or its salt according to (12), or the DNA according to (13).

(35) A method for preventing/treating hypoglycemia, which comprises administering the protein or its salt according to (1), the DNA according to (3), the protein or its salt according to (12), or the DNA according to (13) to a mammal.

(36) Use of the compound or its salt according to (26) for manufacturing the pharmaceutical comprising the compound or its salt according to (26).

(37) A method for preventing/treating hyperglycemia or diabetes mellitus, which comprises administering the protein or its salt according to (26) to a mammal.

BRIEF DESCRIPTION OF THE DRAWINGS

FIG. 1 shows the base sequence of human MD36 gene (cDNA) (SEQ ID NO: 3) and its putative amino acid sequence (SEQ ID NO: 1) (continued to FIG. 2).

FIG. 2 shows the base sequence of human MD36 gene (cDNA) (SEQ ID NO: 3) and its putative amino acid sequence (SEQ ID NO: 1) (continued to FIG. 3).

FIG. 3 shows the base sequence of human MD36 gene (cDNA) (SEQ ID NO: 3) and its putative amino acid sequence (SEQ ID NO: 1) (continued to FIG. 4).

FIG. 4 shows the base sequence of human MD36 gene (cDNA) (SEQ ID NO: 3) and its putative amino acid sequence (SEQ ID NO: 1) (continued to FIG. 5).

FIG. 5 shows the base sequence of human MD36 gene (cDNA) (SEQ ID NO: 3) and its putative amino acid sequence (SEQ ID NO: 1).

FIG. 6 shows the base sequence of human FHOS gene (cDNA) (SEQ ID NO: 4) obtained in EXAMPLE 2 and its putative amino acid sequence (SEQ ID NO: 2) (continued to FIG. 7).

FIG. 7 shows the base sequence of human FHOS gene (cDNA) (SEQ ID NO: 4) obtained in EXAMPLE 2 and its putative amino acid sequence (SEQ ID NO: 2) (continued to FIG. 9).

FIG. 8 shows the base sequence of human FHOS gene (cDNA) (SEQ ID NO: 4) obtained in EXAMPLE 2 and its putative amino acid sequence (SEQ ID NO: 2) (continued to FIG. 9).

FIG. 9 shows the base sequence of human FHOS gene (cDNA) (SEQ ID NO: 4) obtained in EXAMPLE 2 and its putative amino acid sequence (SEQ ID NO: 2) (continued to FIG. 10).

FIG. 10 shows the base sequence of human FHOS gene (cDNA) (SEQ ID NO: 4) obtained in EXAMPLE 2 and its putative amino acid sequence (SEQ ID NO: 2).

FIG. 11 shows the base sequence of truncate type human FHOS gene (cDNA) (SEQ ID NO: 6) and its putative amino acid sequence (SEQ ID NO: 5) (continued to FIG. 12).

FIG. 12 shows the base sequence of truncate type human FHOS gene (cDNA) (SEQ ID NO: 6) and its putative amino acid sequence (SEQ ID NO: 5) (continued to FIG. 13).

FIG. 13 shows the base sequence of truncate type human FHOS gene (cDNA) (SEQ ID NO: 6) and its putative amino acid sequence (SEQ ID NO: 5) (continued to FIG. 14).

FIG. 14 shows the base sequence of truncate type human FHOS gene (cDNA) (SEQ ID NO: 6) and its putative amino acid sequence (SEQ ID NO: 5).

Figure 16:
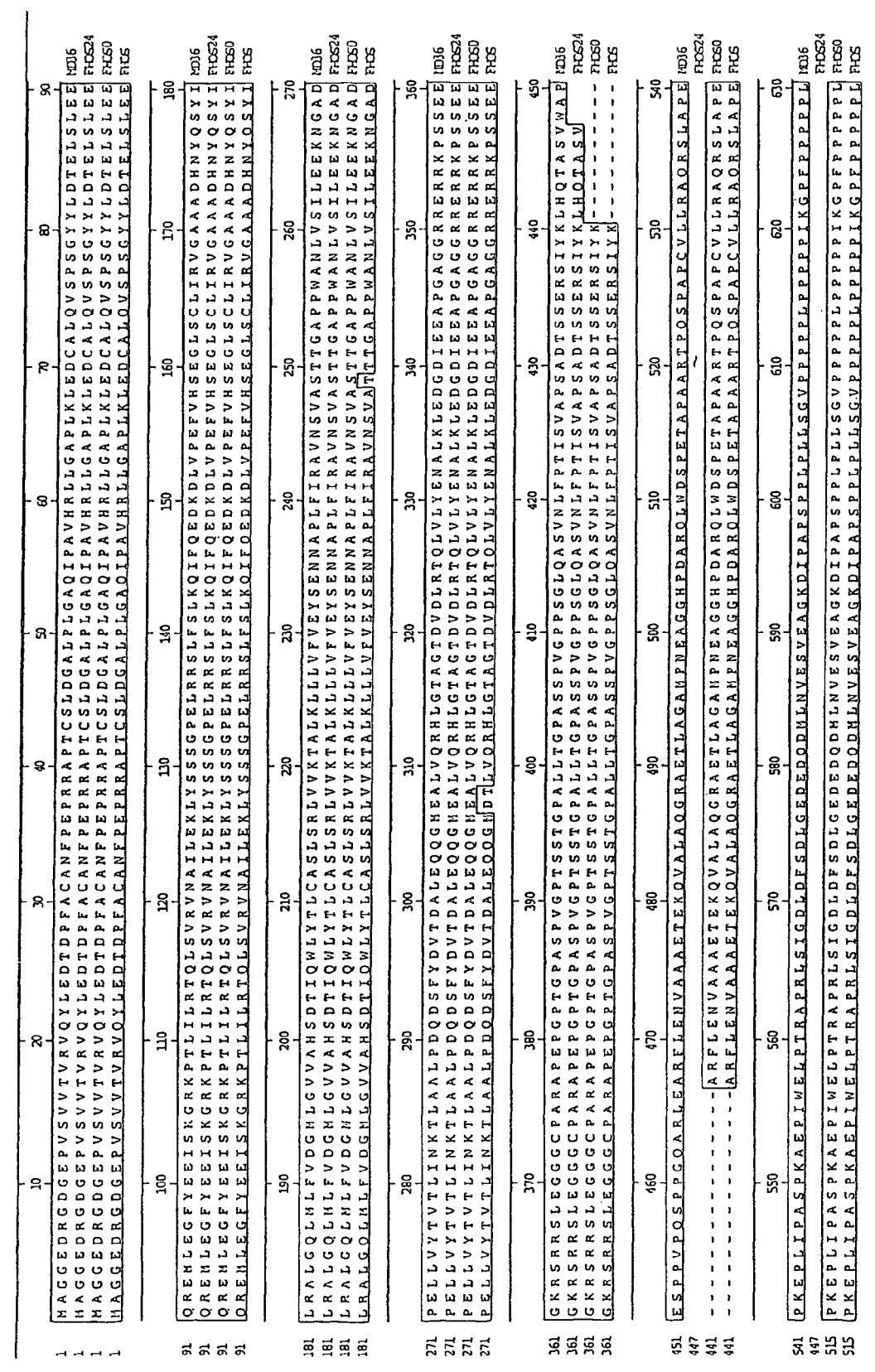

FIG. 16 shows comparison in amino acid sequences between FHOS described in the journal (Westendorf et al., Gene, 232, 173–182, 1999), skeleton muscle-derived MD36 (SEQ ID NO: 1), as well as spleen-derived FHOS and truncate type FHOS obtained in EXAMPLE 2, wherein FHOS (SEQ ID NO: 35), FHOS0 (SEQ ID NO: 2), and FHOS24 (SEQ ID NO: 5) designate FHOS described in the journal supra, FHOS obtained in EXAMPLE 2 and truncate type FHOS, respectively (continued to FIG. 17).

Figure 17:
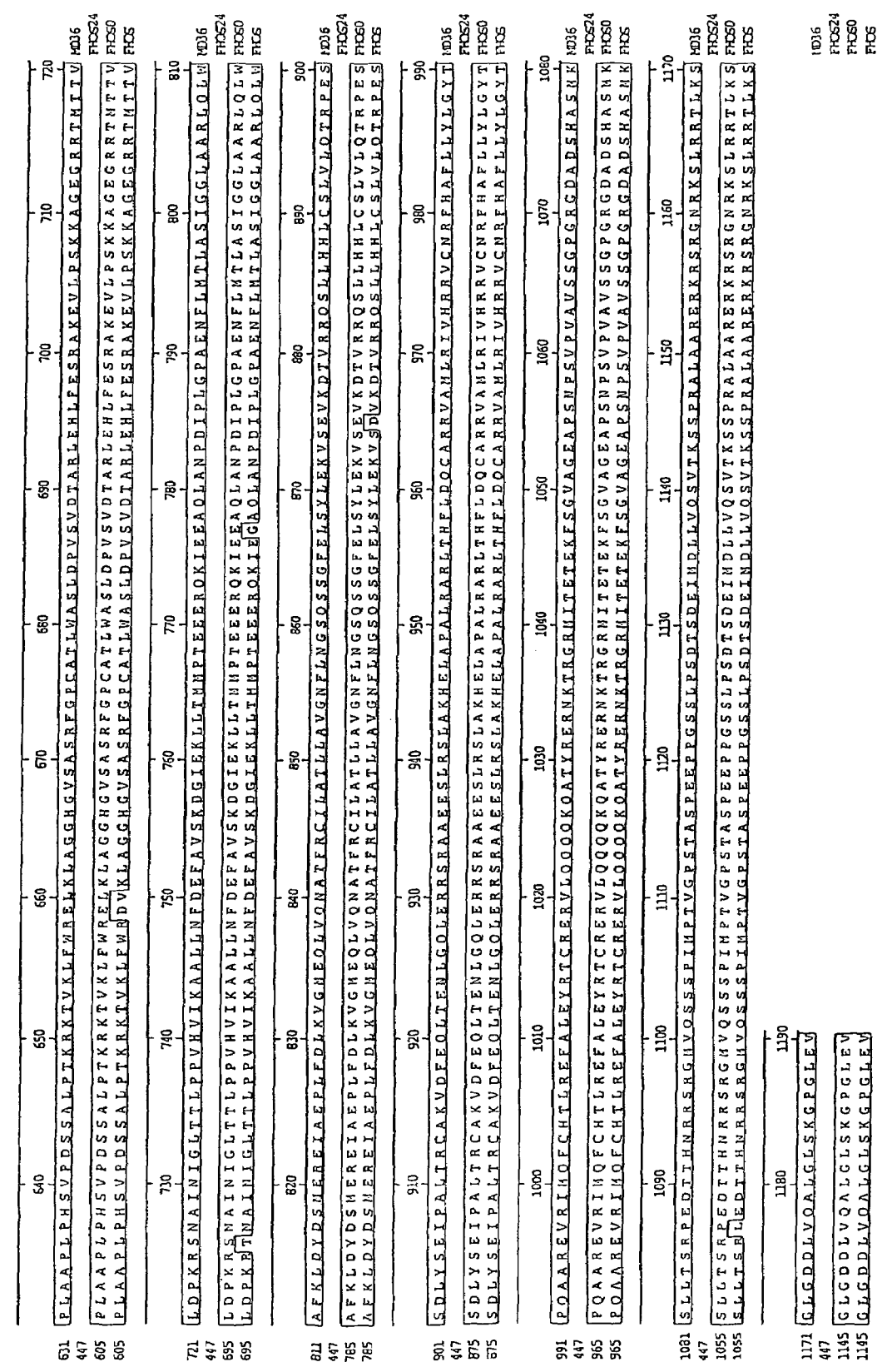

FIG. 17 shows comparison in amino acid sequences between FHOS described in the journal, skeleton muscle-derived MD36 (SEQ ID NO: 1), as well as spleen-derived FHOS obtained in EXAMPLE 2 and truncate type FHOS, wherein FHOS (SEQ ID NO: 35), FHOS0 (SEQ ID NO: 2)

and FHOS24 (SEQ ID NO: 5) designate FHOS described in the journal, FHOS and truncate type FHOS obtained in EXAMPLE 2, respectively.

FIG. 18 shows comparison in protein structure among FHOS, MD36 and truncate type FHOS obtained in EXAMPLE 2, wherein portions shown by box are representative domain structure portions, insert sequences and portions (shaded areas) obtained in EXAMPLE 1.

Figure 19:
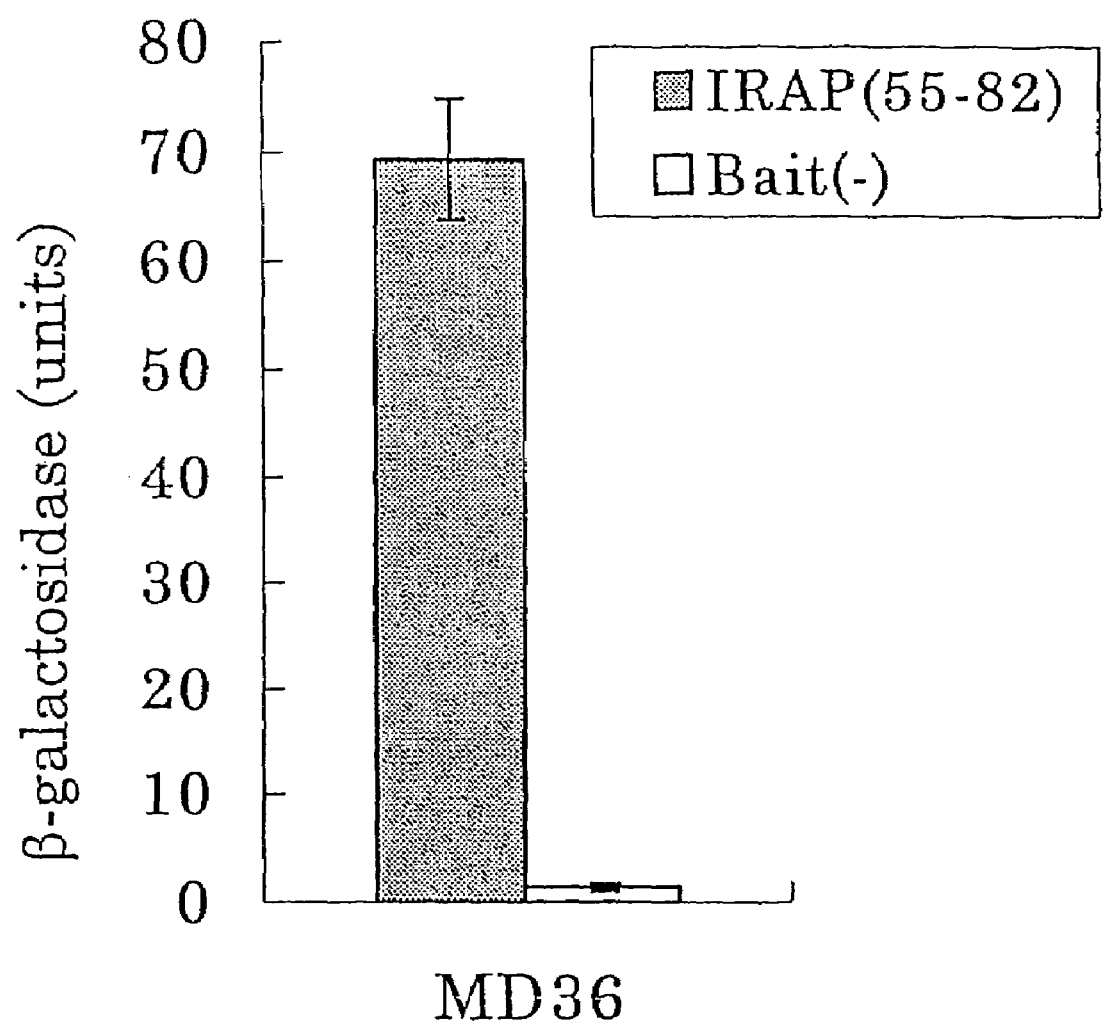

FIG. 19 shows the interaction between IRAP and MD36 by quantification assay of β-galactosidase activity, wherein Bait (−) and IRAP (55–82) designate the bait sequences used, namely, GAL4-BD sequence alone and GAL4-BD fused IRAP (55–82), respectively, and the resulting values are β-galactosidase activity units (mean value±standard deviation).

Figure 20:
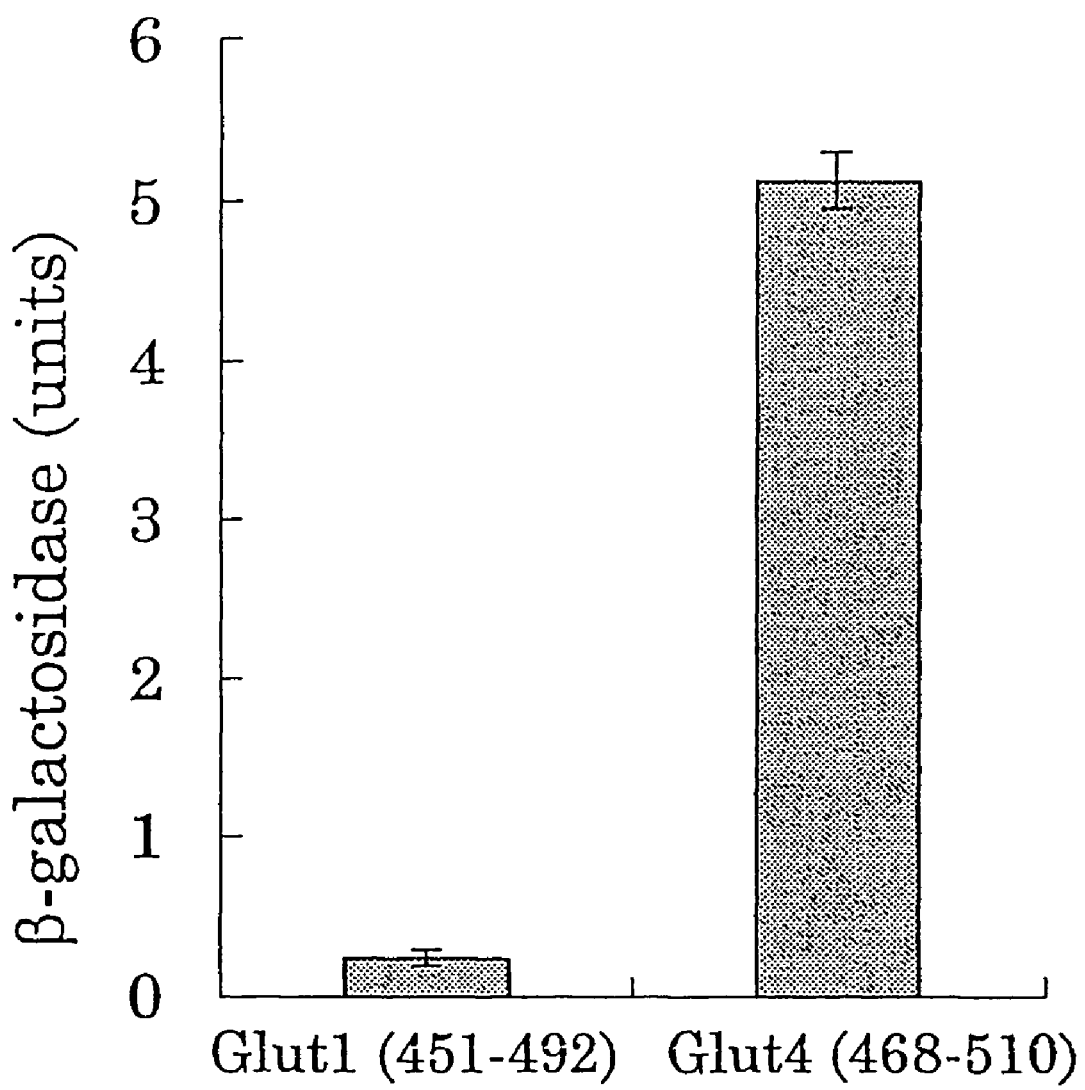

FIG. 20 shows the interaction between glucose transporters and MD36 by quantification assay of β-galactosidase activity, wherein GLUT1 (451–492) and GLUT4 (468–510) designate mouse glucose transporters and their amino acid numbers, respectively, and the resulting values are β-galactosidase activity units (mean value±standard deviation).

Figure 21:
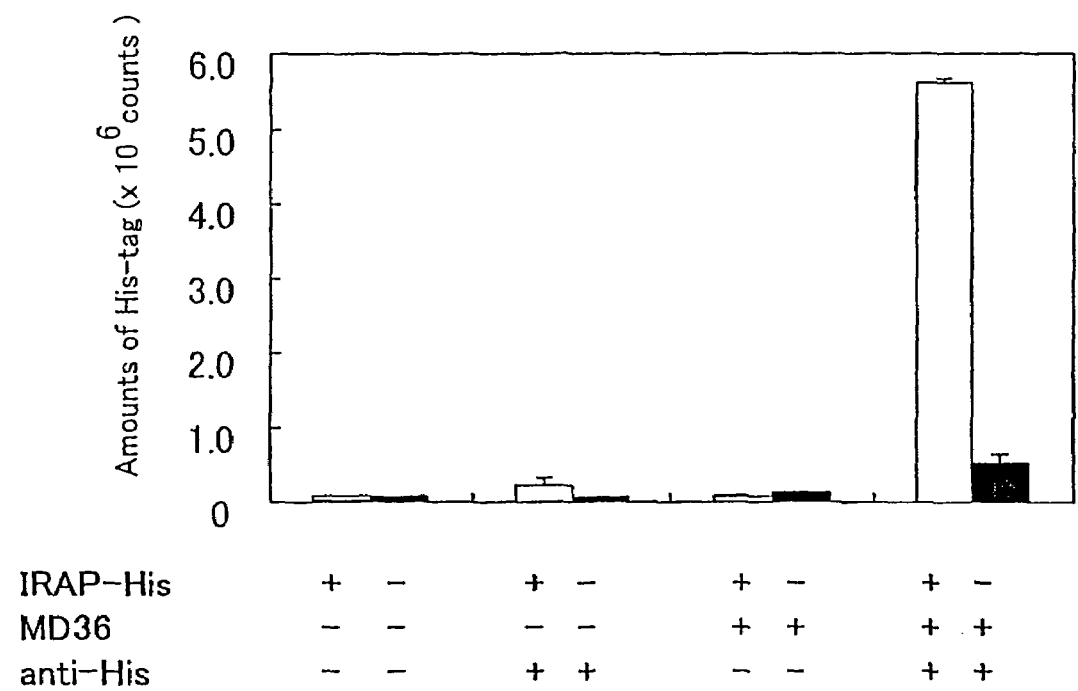

FIG. 21 shows the results of biochemical binding test of human MD36 carried out in EXAMPLE 8. Specifically, the results were obtained by adding IRAP-His (0.1 μg/ml) or anti-Penta-His antibody (diluted to 2000 fold) and both of them to a GST-MD36N4-coated well or a non-coated well, washing the well with TBS-T and then quantitatively assaying the amount of His-Tag remained in the well. In the figure, + designates the added or coated well and − designates the non-added or uncoated well.

Figure 22:
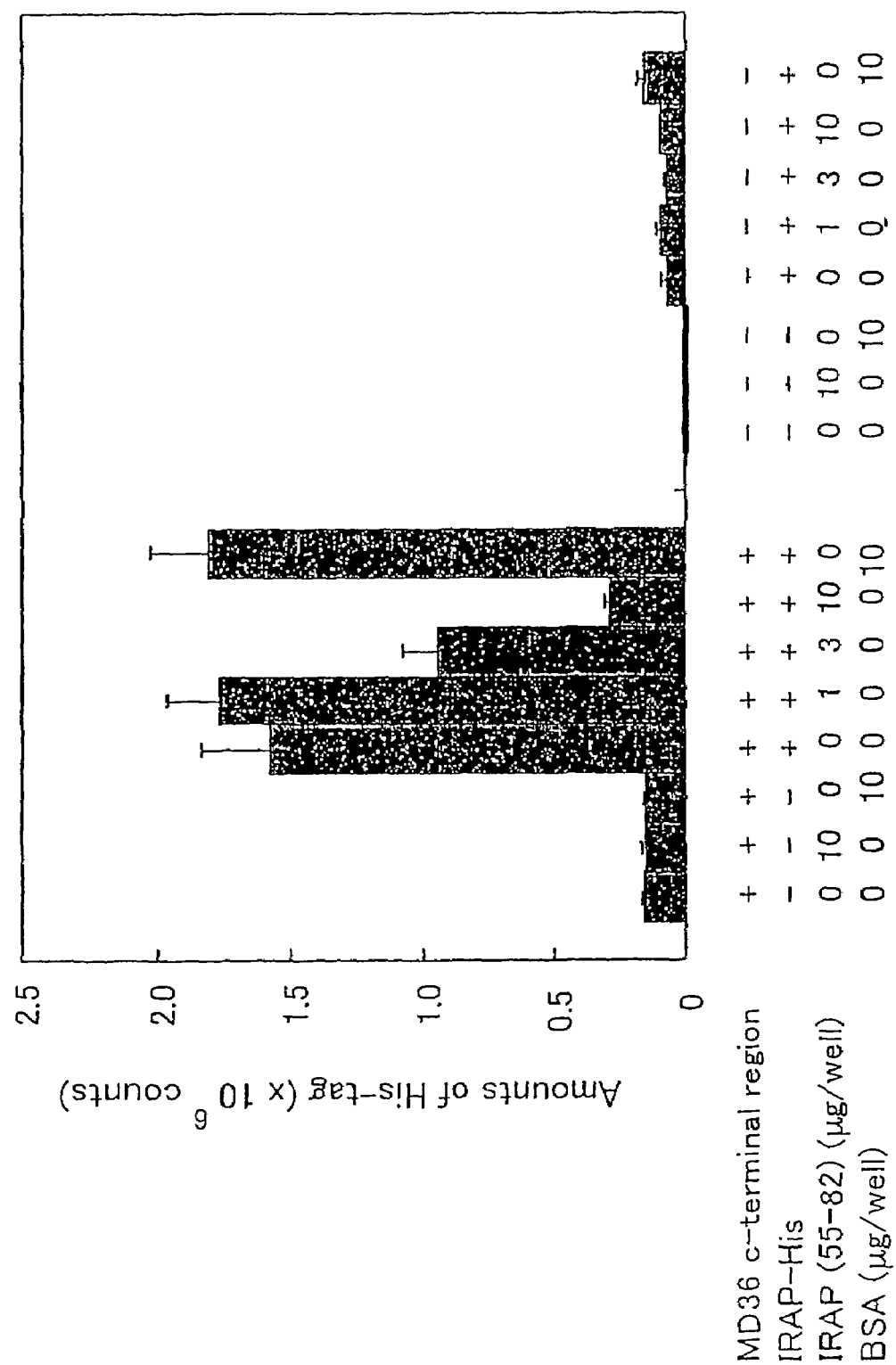

FIG. 22 shows the results of biochemical binding test of human MD36 carried out in EXAMPLE 8. Symbols + and − for the MD36 C-terminal region indicate coating with GST-MD36N4 and no coating, respectively, and + and − for IRAP-His indicate IRAP-His peptide addition and no addition, respectively. The numerical figures for IRAP (55–82) and BSA indicate the respective amounts added (μg/well).

BEST MODE FOR CARRYING OUT THE INVENTION

The protein of the present invention having the same or substantially the same amino acid sequence as the amino acid sequence shown by SEQ ID NO:1 (hereinafter sometimes referred to as the protein of the present invention) may be any protein derived from any cells of warm-blooded animals (e.g., human, guinea pig, rat, mouse, chicken, rabbit, swine, sheep, bovine, monkey, etc.) such as liver cell, splenocyte, nerve cell, glial cell, β cell of pancreas, bone marrow cell, mesangial cell, Langerhans' cell, epidermic cell, epithelial cell, goblet cell, endothelial cell, smooth muscle cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell; or the corresponding precursor cells, stem cells, cancer cells, etc., or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; the proteins may also be synthetic proteins.

The amino acid sequence which has substantially the same amino acid sequence as the amino acid sequence represented by SEQ ID NO:1 includes an amino acid sequence having at least about 98% homology, preferably at least about 99% homology, to the amino acid sequence represented by SEQ ID NO:1.

Preferred examples of the protein which has substantially the same amino acid sequence as the amino acid sequence represented by SEQ ID NO:1 include a protein having substantially the same amino acid sequence as the amino acid sequence represented by SEQ ID NO:1 and having the activity substantially equivalent to that of the amino acid sequence represented by SEQ ID NO:1.

Examples of the substantially equivalent activity include activities of binding to IRAP or GLUT4, etc. The substantially equivalent is used to mean that the nature of these activities is equivalent. Therefore, it is preferred that activities of binding to IRAP or GLUT4, etc., and it is allowable that even differences among levels such as the strength of these activities, molecular weight of the protein and the like, are present.

The protein I of the present invention includes proteins comprising: 1) an amino acid sequence represented by SEQ ID NO:1, of which at least 1 or 2 more (preferably 1 to 25, more preferably 1 to 10 and most preferably several (1 to 5)) amino acids are deleted; 2) an amino acid sequence represented by SEQ ID NO:1, to which at least 1 or 2 more (preferably 1 to 25, more preferably 1 to 10 and most preferably several (1 to 5)) amino acids are added; 3) an amino acid sequence represented by SEQ ID NO:1, into which at least 1 or 2 more (preferably 1 to 25, more preferably 1 to 10 and most preferably several (1 to 5)) amino acids are inserted, 4) an amino acid sequence represented by SEQ ID NO:1, in which at least 1 or 2 more (preferably 1 to 25, more preferably 1 to 10 and most preferably several (1 to 5)) amino acids are substituted by other amino acids; and, 5) proteins or so-called muteins, which have a combination of the above amino acid sequences.

Specific examples of substantially the same amino acid sequence as the amino acid sequence shown by SEQ ID NO:1 are the amino acid sequence shown by SEQ ID NO:15, and the like.

The amino acid sequence which has substantially the same amino acid sequence as the amino acid sequence represented by SEQ ID NO:2 includes an amino acid sequence having at least about 98% homology, preferably at least about 99% homology, to the amino acid sequence represented by SEQ ID NO:2.

Preferred examples of the protein which has substantially the same amino acid sequence as the amino acid sequence represented by SEQ ID NO:2 include a protein having substantially the same amino acid sequence as the amino acid sequence represented by SEQ ID NO:2 and having the activity substantially equivalent to that of the amino acid sequence represented by SEQ ID NO:2.

Examples of the substantially equivalent activity include activities of binding to IRAP or GLUT4, etc. The substantially equivalent is used to mean that the nature of these activities is equivalent. Therefore, it is preferred that activities of binding to IRAP or GLUT4, etc., and it is allowable that even differences among levels such as the strength of these activities, molecular weight of the protein and the like, are present.

The protein II of the present invention includes proteins comprising: 1) an amino acid sequence represented by SEQ ID NO:2, of which at least 1 or 2 more (preferably 1 to 25, more preferably 1 to 10 and most preferably several (1 to 5)) amino acids are deleted; 2) an amino acid sequence represented by SEQ ID NO:2, to which at least 1 or 2 more (preferably 1 to 25, more preferably 1 to 10 and most preferably several (1 to 5)) amino acids are added; 3) an amino acid sequence represented by SEQ ID NO:2, into which at least 1 or 2 more (preferably 1 to 25, more preferably 1 to 10 and most preferably several (1 to 5)) amino acids are inserted, 4) an amino acid sequence represented by SEQ ID NO:2, in which at least 1 or 2 more (preferably 1 to 25, more preferably 1 to 10 and most preferably several (1 to 5)) amino acids are substituted by other amino acids; and, 5) proteins or so-called muteins, which have a combination of the above amino acid sequences.

Specific examples of substantially the same amino acid sequence as the amino acid sequence shown by SEQ ID NO:2 are the amino acid sequence shown by SEQ ID NO:17, and the like.

Throughout the present specification, the proteins are represented in accordance with the conventional way of describing proteins, that is, the N-terminus (amino terminus) at the left hand and the C-terminus (carboxyl terminus) at the right hand. In the protein I or protein II of the present invention including the protein containing the amino acid sequence shown by SEQ ID NO:1 or SEQ ID NO:2, the C-terminus is usually in the form of a carboxyl group (—COOH) or a carboxylate (—COO$^-$) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like.

Where the protein I or protein II of the present invention contains a carboxyl group (or a carboxylate) at the position other than the C-terminus, it may be amidated or esterified and such an amide or ester is also included within the protein I or protein II of the present invention. The ester group may be the same group as that described with respect to the above C-terminal.

Furthermore, examples of the protein I or protein II of the present invention include variants of the above polypeptides, wherein the amino group at the N-terminus (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains.

Specific examples of the protein I of the present invention include a human skeletal muscle-derived protein containing the amino acid sequence represented by SEQ ID NO:1, a mouse-derived protein containing the amino acid sequence represented by SEQ ID NO:15, etc.

Specific examples of the protein II of the present invention include a human spleen-derived protein containing the amino acid sequence represented by SEQ ID NO:2, FHOS protein described in the journal (Westendorf et al., Gene, 232, 173–182, 1999; Genbank Accession No. AF113615), a mouse-derived protein containing the amino acid sequence represented by SEQ ID NO:17, etc.

The partial peptides of the protein I of the present invention (hereinafter sometimes referred to as the partial peptide I of the present invention) may be any partial peptides of the protein I of the present invention described above, preferably those having activities similar to those of the protein I of the present invention described above. For example, there are employed peptides containing at least 20, preferably at least 50, more preferably at least 70, much more preferably at least 100 and most preferably at least 200 amino acid sequences in the amino acid sequences constituting the protein I of the present invention. Particularly preferably, there are employed peptides containing consecutive 200, inclusive, to less than 1190 (more preferably 200, inclusive, to less than 400) amino acid residues from the C terminus of the protein I of the present invention.

The partial peptide I of the present invention may contain an amino acid sequence wherein at least 1 or 2 (preferably 1 to 10, more preferably several (1 to 5)) amino acids are deleted, an amino acid sequence to which at least 1 or 2 (preferably 1 to 10, more preferably several (1 to 5)) amino acids are added, an amino acid sequence wherein at least 1 or 2 (preferably 1 to 10, more preferably several (1 to 5)) amino acids are inserted, or an amino acid sequence wherein at least 1 or 2 (preferably 1 to 10, more preferably several (1 to 5)) amino acids are substituted by other amino acids.

In the partial peptide I of the present invention, the C-terminus is normally a carboxyl group (—COOH) or carboxylate (—COO$^-$) but the C-terminus may be in the form of an amide (—CONH$_2$) or an ester (—COOR), as has been described with the protein I of the present invention.

Where the partial peptide I of the present invention contains a carboxyl group (or a carboxylate) at positions other than the C terminus, peptides wherein the carboxyl group is amidated or esterified are also included within the partial peptide I of the present invention. Examples of the ester are the C-terminal esters described above.

As in the protein I of the present invention described above, the partial peptide I of the present invention further includes conjugated peptides such as those in which the amino group of the N-terminal amino acid residue (e.g., methionine residue) is protected by a protecting group, those in which the N-terminal residue is cleaved in vivo and the produced glutamine residue is pyroglutaminated, those in which substituents on the side chains of amino acids in the molecule are protected by appropriate protecting groups and conjugated proteins such as so-called glycoproteins having sugar chains.

The partial peptide I of the present invention can be employed as an antigen for producing an antibody and also for screening of the compounds that inhibit the binding of the protein I of the present invention to IRAP or GLUT4.

The partial peptides of the protein II of the present invention (hereinafter sometimes referred to as the partial peptide II of the present invention) may be any partial peptides of the protein II of the present invention described above, preferably those having activities similar to those of the protein II of the present invention described above. For example, there are employed peptides containing at least 20, preferably at least 50, more preferably at least 70, much more preferably at least 100 and most preferably at least 200 amino acid sequences in the amino acid sequences constituting the protein II of the present invention. Particularly preferably, there are employed peptides containing consecutive 200, inclusive, to less than 1164 (more preferably 200, inclusive, to less than 400) amino acid residues from the C terminus of the protein I of the present invention.

The partial peptide II of the present invention may contain an amino acid sequence wherein at least 1 or 2 (preferably 1 to 10, more preferably several (1 to 5)) amino acids are deleted, an amino acid sequence to which at least 1 or 2 (preferably 1 to 10, more preferably several (1 to 5)) amino acids are added, an amino acid sequence wherein at least 1 or 2 (preferably 1 to 10, more preferably several (1 to 5)) amino acids are inserted, or an amino acid sequence wherein at least 1 or 2 (preferably 1 to 10, more preferably several (1 to 5)) amino acids are substituted by other amino acids.

In the partial peptide II of the present invention, the C-terminus is normally a carboxyl group (—COOH) or carboxylate (—COO⁻) but the C-terminus may be in the form of an amide (—CONH$_2$) or an ester (—COOR), as has been described with the protein II of the present invention.

Where the partial peptide II of the present invention contains a carboxyl group (or a carboxylate) at positions other than the C terminus, peptides wherein the carboxyl group is amidated or esterified are also included within the partial peptide II of the present invention. Examples of the ester are the C-terminal esters described above.

As in the protein II of the present invention described above, the partial peptide II of the present invention further includes conjugated peptides such as those in which the amino group of the N-terminal amino acid residue (e.g., methionine residue) is protected by a protecting group, those in which the N-terminal residue is cleaved in vivo and the produced glutamine residue is pyroglutaminated, those in which substituents on the side chains of amino acids in the molecule are protected by appropriate protecting groups and conjugated proteins such as so-called glycoproteins having sugar chains.

The partial peptide II of the present invention can be employed as an antigen for producing an antibody and also for screening of the compounds that inhibit the binding of the protein II of the present invention to IRAP or GLUT4.

As salts of the protein I or partial peptide I, or protein II or partial peptide II of the present invention, there are employed salts with physiologically acceptable acids (e.g., inorganic acids or organic acids) or bases (e.g., alkali metal salts), particularly preferred are physiologically acceptable acid addition salts. Examples of such salts are salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein I, partial peptide I, protein II or partial peptide II, or its salts, of the present invention may be manufactured from the warm-blooded animal cells or tissues described above by a publicly known method of purifying proteins, or maybe manufactured by culturing a transformant containing a DNA encoding these proteins or peptides. They may also be manufactured by modifications of peptide synthesis described hereinafter.

Where they are manufactured from mammalian tissues or cells, mammalian tissues or cells are homogenized, then extracted with an acid or the like, and the extract is isolated and purified by a combination of chromatography techniques such as reverse phase chromatography, ion exchange chromatography, and the like.

The protein I, partial peptide I, protein II or partial peptide II of the present invention, amides or salts thereof may be synthesized using commercially available resins normally employed for protein synthesis. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein or peptide according to various condensation methods publicly known in the art. At the end of the reaction, the protein or peptide is excised from the resin and at the same time, the protecting groups are removed. Then, intramolecular disulfide bond-forming reaction is performed in a highly diluted solution to obtain the objective protein, peptide or amides thereof.

For condensation of the protected amino acids described above, a variety of activation reagents for protein synthesis may be used, but carbodiimides are particularly preferably employed. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethyl-benzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the objective protein or peptide of the present invention, for example, the α-carboxyl group of the carboxy terminal amino acid is first protected by amidation; the peptide (protein) chain is then extended from the amino group side to a desired length. Thereafter, a protein or peptide in which only the protecting group of the N-terminal α-amino group has been eliminated from the protein or peptide and a protein or peptide in which only the protecting group of the C-terminal carboxyl group has been eliminated are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the objective esterified protein or peptide of the present invention, for example, the α-carboxyl group of the carboxy terminal amino acid is condensed with a desired alcohol to prepare the amino acid ester, which is followed by procedure similar to the preparation of the amidated protein or peptide above to give the desired esterified protein or peptide.

The partial peptide I or partial peptide II, or its salts, of the present invention can be manufactured by publicly known methods for peptide synthesis, or by cleaving the protein I or protein II of the present invention with an appropriate peptidase. For the methods for peptide synthesis, for example, either solid phase synthesis or liquid phase synthesis may be used. That is, the partial peptide or amino acids that can construct the partial peptide of the present invention are condensed with the remaining part (peptide or amino acid). Where the product contains protecting groups, these protecting groups are removed to give the desired peptide. Publicly known methods for condensation and elimination of the protecting groups are described in 1)–5) below.

1) M. Bodanszky & M. A. Ondetti: Peptide Synthesis, Interscience Publishers, New York (1966)
2) Schroeder & Luebke: The Peptide, Academic Press, New York (1965)
3) Nobuo Izumiya, et al.: Peptide Gosei-no-Kiso to Jikken (Basics and experiments of peptide synthesis), published by Maruzen Co. (1975)
4) Haruaki Yajima & Shunpei Sakakibara: Seikagaku Jikken Koza (Biochemical Experiment) 1, Tanpakushitsu no Kagaku (Chemistry of Proteins) IV, 205 (1977)
5) Haruaki Yajima ed.: Zoku lyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the protein or peptide of the present invention. When the protein or peptide obtained by the above methods is in a free form, the protein or peptide can be converted into an appropriate salt by a publicly known method; when the protein or peptide is obtained in a salt form, it can be converted into a free form or a different salt form by a publicly known method.

The DNA encoding the protein I or protein II of the present invention may be any DNA so long as it contains the base sequence encoding the protein I or protein II of the present invention described above. Such a DNA may also be any one of genomic DNA, genomic DNA library, cDNA derived from the cells/tissues described above, cDNA library derived from the cells/tissues described above and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Specifically, the DNA encoding the protein I of the present invention may be any one of, for example, a DNA containing the base sequence represented by SEQ ID NO:3 (DNA containing the base sequence of base numbers 19–3588 in the base sequence shown by SEQ ID NO:23), a DNA containing the base sequence represented by SEQ ID NO:23, a DNA containing the base sequence represented by SEQ ID NO:16, a DNA containing the base sequence represented by SEQ ID NO:26, or any DNA having a base sequence hybridizable to the base sequence represented by SEQ ID NO:3 (DNA containing the base sequence of base numbers 19–3588 in the base sequence shown by SEQ ID NO:23) under high stringent conditions, a base sequence hybridizable to the base sequence represented by SEQ ID NO:23 under high stringent conditions, a base sequence hybridizable to the base sequence represented by SEQ ID NO:16 under high stringent conditions, or a base sequence hybridizable to the base sequence represented by SEQ ID NO:26 under high stringent conditions, and encoding a protein which has the activities substantially equivalent to those of the protein I of the present invention. The DNA encoding the protein II may be any one of, for example, a DNA containing the base sequence represented by SEQ ID NO:4 (DNA containing the base sequence of base numbers 19–3510 in the base sequence shown by SEQ ID NO:24), a DNA containing the base sequence represented by SEQ ID NO:24, a DNA containing the base sequence represented by SEQ ID NO:18, a DNA containing the base sequence represented by SEQ ID NO:27, or any DNA having a base sequence hybridizable to the base sequence represented by SEQ ID NO: NO:4 (DNA containing the base sequence of base numbers 19–3510 in the base sequence shown by SEQ ID NO:24) under high stringent conditions, a base sequence hybridizable to the base sequence represented by SEQ ID NO:24 under high stringent conditions, a base sequence hybridizable to the base sequence represented by SEQ ID NO:18 under high stringent conditions, or a base sequence hybridizable to the base sequence represented by SEQ ID NO:27 under high stringent conditions, and encoding a protein which has the activities substantially equivalent to those of the protein II.

Specific examples of the DNA that is hybridizable to the DNA containing the base sequence represented by SEQ ID NO:3 (DNA containing the base sequence of base numbers 19–3588 in the base sequence shown by SEQ ID NO:23), the DNA containing the base sequence represented by SEQ ID NO:23, the DNA containing the base sequence represented by SEQ ID NO:16, or the DNA containing the base sequence represented by SEQ ID NO:26, under high stringent conditions, include a DNA having at least about 98% homology and preferably at least about 99% homology, to the base sequence represented by SEQ ID NO:3, the base sequence represented by SEQ ID NO:23, the base sequence represented by SEQ ID NO:16, or the base sequence represented by SEQ ID NO:26.

Specific examples of the DNA that is hybridizable to the DNA containing the base sequence represented by SEQ ID NO:4 (DNA containing the base sequence of base numbers 19–3510 in the base sequence shown by SEQ ID NO:24), the DNA containing the base sequence represented by SEQ ID NO:24, the DNA containing the base sequence represented by SEQ ID NO:18 or the DNA containing the base sequence represented by SEQ ID NO:27, under high stringent conditions, include a DNA having at least about 98% homology and preferably at least about 99% homology, to the base sequence represented by SEQ ID NO:4, the base sequence represented by SEQ ID NO:24, the base sequence represented by SEQ ID NO:18, or the base sequence represented by SEQ ID NO:27.

The hybridization can be carried out by publicly known methods or by a modification thereof, for example, according to the method described in Molecular Cloning, 2nd Ed. (J. Sambrook et al., Cold Spring Harbor Lab. Press, 1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration at about 19 mM at a temperature of about 65° C. are most preferred.

More specifically, for the DNA encoding the protein having the amino acid sequence represented by SEQ ID NO:1, there may be employed DNA having the base sequence represented by SEQ ID NO:3, and the like.

More specifically, a DNA having the base sequence represented by SEQ ID NO:4 or the like is employed as the DNA encoding the protein having the amino acid sequence represented by SEQ ID NO:2.

More specifically, a DNA having the base sequence represented by SEQ ID NO:16 or the like is employed as the DNA encoding the protein having the amino acid sequence represented by SEQ ID NO:15.

More specifically, a DNA having the base sequence represented by SEQ ID NO:18 or the like is employed as the DNA encoding the protein having the amino acid sequence represented by SEQ ID NO:17.

The DNA encoding the partial peptide I or partial peptide II of the present invention may be any DNA so long as it contains the base sequence encoding the partial peptide I or partial peptide II of the present invention described above. Such a DNA may also be any one of genomic DNA, genomic DNA library, cDNA derived from the cells/tissues described above, cDNA library derived from the cells/tissues described above and synthetic DNA.

As the DNA encoding the partial peptide I of the present invention, there may be employed, for example, a DNA containing a part of the base sequence represented by SEQ ID NO:3 or a DNA containing a part of the base sequence represented by SEQ ID NO:16, or a DNA containing a base sequence hybridizable to the base sequence represented by SEQ ID NO:3 or the base sequence represented by SEQ ID NO:16 under high stringent conditions and containing a part of a DNA encoding a protein which has the activities substantially equivalent to those of the protein I of the present invention.

Examples of the DNA hybridizable to the DNA containing the base sequence represented by SEQ ID NO:3 or the base sequence represented by SEQ ID NO:16 are the same as given above.

As the DNA encoding the partial peptide II, there may be employed, for example, a DNA containing a part of the base sequence represented by SEQ ID NO:4, a DNA containing a part of the base sequence represented by SEQ ID NO:18, or any DNA having a base sequence hybridizable to the base sequence represented by SEQ ID NO: NO:4 or the base sequence represented by SEQ ID NO:18 under high stringent conditions and containing a part of a DNA encoding a protein which has the activities substantially equivalent to those of the protein II.

Examples of the DNA hybridizable to the DNA containing the base sequence represented by SEQ ID NO:4 or the base sequence represented by SEQ ID NO:18 are the same as given above.

Methods for the hybridization and the high stringent conditions that can be used are also the same as described above.

For cloning of the DNA encoding the protein I, partial peptide I, protein II or partial peptide II of the present invention (hereinafter sometimes merely referred to as the protein of the present invention), the DNA can be screened either by amplification through PCR using synthetic DNA primers having a partial base sequence of the protein of the present invention, or by hybridization of a DNA inserted into an appropriate vector using a DNA fragment or a synthetic DNA encoding a part of or the entire region of the protein of the present invention. The hybridization maybe carried out by publicly known methods, for example, according to the method described in Molecular Cloning, 2nd Ed. (J. Sambrook et al., Cold Spring Harbor Lab. Press, 1989), etc. A commercially available library may also be used according to the instructions of the attached manufacturer's protocol.

Conversion of the base sequence of DNA can be effected by publicly known methods such as the ODA-LA PCR method, the Gapped duplex method, the Kunkel method, etc. or its modification, by using a publicly known kit available as Mutan™-G (manufactured by Takara Shuzo Co., Ltd., trademark), Mutan™-K (manufactured by Takara Shuzo Co., Ltd., trademark), or the like.

The cloned DNA encoding the protein of the present invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the protein of the present invention can be manufactured, for example, by (a) excising the desired DNA fragment from the DNA encoding the protein of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λPL promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as Neo, G418 resistance), etc. In particular, when dhfr gene is used as the selection marker together with dhfr gene, selection can also be made on thymidine free media.

If necessary, a signal sequence that matches with a host is added to the N-terminus of the protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the protein of the present invention thus constructed, transformants can be manufactured.

Examples of the host, which maybe employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207–21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, Bombyx mori N cell (BmN cell), etc. is used. Examples of the Sf cell which can be used are Sf9 cell (ATCC CRL1711) and Sf21 cell (both cells are described in Vaughn, J. L. et al., In Vivo, 13, 213–217 (1977).

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO (dhfr⁻) cell), mouse L cell, mouse AtT-20, mouse myeloma cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263–267 (1995), published by Shujunsha, or Virology, 52, 456 (1973).

Thus, the transformant transformed with the expression vector containing the DNA encoding the protein of the present invention can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary, the culture maybe aerated or agitated.

Where the bacteria belonging to the genus *Bacillus* are used as the host, the transformant is cultivated generally at about 30° C. to about 40° C. for about 6 hours to about 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the protein of the present invention can be produced in the cell membrane of the transformant, etc.

The protein of the present invention can be separated and purified from the culture described above by the following procedures.

When the protein of the present invention is extracted from the culture or cells, after cultivation the transformant or cell is collected by a publicly known method and suspended in an appropriate buffer. The transformant or cell is then disrupted by publicly known methods such as ultrasonication, a treatment with lysozyme and/or freeze-thaw cycling, followed by centrifugation, filtration, etc. Thus, the crude extract of the protein can be obtained. The buffer used for the procedures may contain a protein modifier such as urea or guanidine hydrochloride, or a surfactant such as Triton X-100™, etc. When the protein or its partial peptide of the present invention is secreted in the culture broth, after completion of the cultivation the supernatant can be separated from the transformant or cell to collect the supernatant by a publicly known method.

The supernatant or the protein of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein of the present invention thus obtained is in a free form, it can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein modifying enzyme so that the protein can be appropriately modified to partially remove a polypeptide. Examples of the protein-modifying enzyme include trypsin, chymotrypsin, arginyl endopeptidase, protein kinase, glycosidase, and the like.

The presence of the thus produced protein of the present invention or salts thereof can be assayed by enzyme immunoassay using a specific antibody, Western blotting, etc.

Antibodies to the protein I, partial peptide I, protein II or partial peptide II, or its salts, of the present invention maybe any of polyclonal antibodies and monoclonal antibodies, as long as they are capable of recognizing the protein I, partial peptide I, protein II or partial peptide II, or its salts, of the present invention.

The antibodies to the protein I, partial peptide I, protein II or partial peptide II, or its salts, of the present invention (hereinafter sometimes merely referred to as the protein of the present invention) may be manufactured by publicly known methods for manufacturing antibodies or antisera, using as antigens the protein of the present invention. As the protein of the present invention used as antigens, any one of the protein I, partial peptide I, protein II or partial peptide II, or its salts, of the present invention described above is usable, and specifically exemplified by, e.g., a partial peptide composed of the amino acid sequence represented by Arg-Glu-Arg-Lys-Arg-Ser-Arg-Gly-Asn-Arg-Lys-Ser-Leu-Arg-Arg (partial amino acid sequence of 1152–1166 from the N terminus of the amino acid sequence shown by SEQ ID NO:1), a partial peptide composed of the amino acid sequence represented by Ala-Val-Gly-Asn-Phe-Leu-Asn-Gly-Ser-Gln-Ser (partial amino acid sequence of 852–862 from the N terminus of the amino acid sequence shown by SEQ ID NO:1), and the like.

[Preparation of Monoclonal Antibody]

(a) Preparation of Monoclonal Antibody-Producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants maybe administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the protein (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Preparation of Polyclonal Antibody]

The polyclonal antibody of the present invention can be manufactured by publicly known methods or modifications thereof. For example, a warm-blooded animal is immunized with an immunogen (protein antigen) per se, or a complex of immunogen and a carrier protein is formed and a warm-blooded animal is immunized with the complex in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group, dithiopyridyl group, or the like are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant maybe administered. The administration is usually made once every 2 to 6 weeks and 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNA having a complementary or substantial complementary base sequence to the DNA coding for the protein I, partial peptide I, protein II or partial peptide II of the present invention (hereinafter these DNAs are sometimes collectively referred to as the DNA of the present invention) can be any antisense DNA so long as it possesses a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon). These antisense DNAs can be synthesized using a publicly known DNA synthesizer, etc.

Also, the antisense DNA is used in the meaning to include, e.g., not only those complementary or substantially complementary to a DNA containing the base sequence shown by SEQ ID NO:3 encoding the protein having the amino acid sequence shown by SEQ ID NO:1 or the base sequence shown by SEQ ID NO:4 encoding the protein having the amino acid sequence shown by SEQ ID NO:2, or to its partial DNA, and having the activity capable of suppressing expression of the DNA; but also those complementary or substantially complementary to a DNA having further upstream base sequence (specifically, the 1–18 base sequence in the base sequence shown by SEQ ID NO:23, the 1–18 base sequence in the base sequence shown by SEQ ID NO:24, etc.) at the 5' end, or further downstream base sequence (specifically, the 3592–3853 base sequence in the amino acid sequence shown by SEQ ID NO:23, the 3514–3775 base sequence in the base sequence shown by SEQ ID NO:24, etc.) at the 3' end, of the DNA containing the base sequence shown by SEQ ID NO:3 encoding the protein having the amino acid sequence shown by SEQ ID NO:1 or the base sequence shown by SEQ ID NO:4 encoding the protein having the amino acid sequence shown by SEQ ID NO:2, or to its partial DNA, and having the activity capable of suppressing expression of the DNA having the base sequence shown by SEQ ID NO:3 encoding the protein having the amino acid sequence shown by SEQ ID NO:1 or the base sequence shown by SEQ ID NO:4 encoding the protein having the amino acid sequence shown by SEQ ID NO:2. Hereinafter the utilities of the protein I, partial peptide I, protein II or partial peptide II, or its salt of the present invention (hereinafter sometimes referred to as the protein of the present invention), the DNA encoding the protein I, partial peptide I, protein II or partial peptide II, or its salt of the present invention (hereinafter sometimes referred to as the DNA of the present invention), the antibody to the DNA encoding the protein I, partial peptide I, protein II or partial peptide II, or its salt of the present invention (hereinafter sometimes referred to as the antibody of the present invention), and the antisense are described.

(1) Prophylactic/Therapeutic Agent for Various Diseases Associated with the Protein of the Present Invention The protein of the present invention binds to IRAP to retain GLUT4 vesicles (vesicles in which proteins such as GLUT4, IRAP, VAMPs, SCAMPs, Rab4, etc. are localized) in cells and prevent blood sugar from taking up into muscle cells and adipocytes, resulting in an elevated blood sugar level. Thus, the protein of the present invention or the DNA of the present invention can be used as pharmaceuticals for the prevention/treatment of various diseases such as hypoglycemia, etc.

When a patient has a reduced level of, or deficient of the protein, etc. of the present invention in his or her body and thus may not maintain homeostasis in the body or may not exhibit the biophylactic mechanism sufficiently or properly, the protein of the present invention can provide its role sufficiently or properly for the patient, (a) by administering the DNA of the present invention to the patient to express the protein of the present invention in the body, (b) by inserting the DNA of the present invention into a cell, expressing the protein of the present invention and then transplanting the cell to the patient, or (c) by administering the protein of the present invention to the patient, etc.

Where the DNA of the present invention is used as the prophylactic/therapeutic agents described above, the DNA per se is administered directly to warm-blooded animal; alternatively, the DNA is inserted into an appropriate vector such as retrovirus vector, adenovirus vector, adenovirus-associated virus vector, etc. and then administered to warm-blooded animal in a conventional manner. The DNA of the present invention may also be administered as intact DNA, or with adjuvants to assist its uptake by gene gun or through a catheter such as a catheter with a hydrogel.

Where the protein of the present invention is used as the aforesaid therapeutic/prophylactic agents, the protein or the protein is advantageously used on a purified level of at least 90%, preferably at least 95%, more preferably at least 98% and most preferably at least 99%.

The protein of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing the protein of the present invention with a physiologically acceptable carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention has been inserted may also be prepared into pharmaceutical preparations in a manner similar to the procedures above. Such preparations are generally used parenterally.

Since the thus obtained pharmaceutical preparation is safe and low toxic, the preparation can be administered to or other warm-blooded animal (e.g., human, rat, mouse, guinea pig, rabbit, chicken, sheep, swine, bovine, horse, cat, dog, monkey, chimpanzee, etc.).

The dose of the protein of the present invention varies depending on target disease, subject to be administered, route for administration, etc.; for example, in oral administration for the treatment of hyperglycemia, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc. but it is advantageous for the treatment of hyperglycemia to administer the active ingredient intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of the Binding Inhibiting Substance

The protein of the present invention binds to the cytoplasmic side domain of IRAP to retain GLUT4 vesicles in the cell and prevent blood sugar uptake into the skeletal muscle cell and adipocyte. Therefore, the compound that inhibits the binding of the protein of the present invention to IRAP, preferably the compound that inhibits the binding of the protein of the present invention to the cytoplasmic side domain of IRAP, promotes blood sugar uptake into the skeletal muscle cell and adipocyte, whereby the blood sugar level can be reduced and thus, the compound is useful as pharmaceuticals for the prevention/treatment of diseases, e.g., hyperglycemia, diabetes mellitus, etc.

As is shown in EXAMPLE 4 later described, the protein of the present invention also binds to the domain (amino acid numbers 468–510 of GLUT4; SEQ ID NO:13) in the cytoplasm to retain GLUT4 vesicles in the cell and prevent blood sugar uptake into the skeletal muscle cell and adipocyte. Therefore, the compound that inhibits the binding of the protein of the present invention to GLUT4, preferably the compound that inhibits the binding of the protein of the present invention to the domain of GLUT4 in the cytoplasm, promotes blood sugar uptake into the skeletal muscle cell and adipocyte, whereby the blood sugar level can be reduced and thus, the compound is useful as pharmaceuticals for the prevention/treatment of diseases, e.g., hyperglycemia, diabetes mellitus, etc., as in the compound that inhibits the binding of the protein of the present invention to IRAP.

For the screening method of the present invention, the protein of the present invention is employed; a peptide corresponding to IRAP or the cytoplasmic side domain of IRAP, or to GLUT4 or the domain of GLUT4 in the cytoplasm may further be employed. Furthermore, a cell (preferably, a transformant (a cell such as yeast, animal cell, etc.) transformed by the DNA encoding the protein of the present invention) capable of producing the protein of the present invention may also be used for the screening method of the present invention. The transformant maybe a transformant transformed by the DNA encoding the protein of the present invention or by the DNA encoding the peptide corresponding to IRAP or the cytoplasmic side domain of IRAP, or a transformant transformed by the DNA encoding the protein of the present invention or by the DNA encoding the peptide corresponding to GLUT4 or the domain of GLUT4 in the cytoplasm.

(2-1) Screening by Binding Test In Vitro

The protein of the present invention is immobilized onto a solid phase (e.g., an EIA plate), using antibodies to the protein of the present invention. Alternatively, the protein of the present invention is fused to Tag protein (e.g., His-Tag, GST (glutathione-S-transferase), etc.) and then immobilized onto a solid phase. In the case that the partial peptide of the present invention is used as the protein of the present invention, preferably a partial peptide (the amino acid numbers 977–1190 in SEQ ID NO:1, the amino acid numbers 951–1164 in SEQ ID NO:2, etc.) having a binding activity to IRAP or GLUT4 is employed. In the immobilization of the protein onto a solid phase, nickel is used for His-Tag and for GST, glutathione is used. Thereto is added a partial peptide (amino acid sequence represented by SEQ ID NO:11 or its partial peptide, preferably the amino acid numbers 55–82 of SEQ ID NO:11) corresponding to IRAP or the cytoplasmic side domain of IRAP, or a partial peptide (SEQ ID NO:13) corresponding to GLUT4 or the domain of GLUT4 in the cytoplasm, which is labeled with biotin, etc. After a test compound is added to the resulting complex, IRAP or an IRAP partial peptide, or GLUT4 or a GLUT4 partial peptide, which is liberated as a result of the binding of the protein of the present invention to IRAP or GLUT4 being inhibited, is detected and quantified using a commercially available kit for detecting the label such as biotin, etc., or a publicly known anti-IRAP antibody or a commercially available anti-GLUT4 antibody. The compounds that release IRAP or an IRAP partial peptide, or GLUT4 or a GLUT4 partial peptide are screened as the compounds that inhibit the binding of the protein of the present invention to IRAP or GLUT4 (hereinafter sometimes merely referred to as the binding inhibitor).

Furthermore, a partial peptide (amino acid sequence represented by SEQ ID NO:11 or its partial peptide, preferably the amino acid numbers 55–82 of SEQ ID NO:11) corresponding to IRAP or the cytoplasmic side domain of IRAP, or a partial peptide (SEQ ID NO:13) corresponding to GLUT4 or the domain of GLUT4 in the cytoplasm, is immobilized onto a solid phase, and the partial peptide is added to the immobilized peptide. In the immobilization of IRAP or an IRAP partial peptide, or GLUT4 or a GLUT4 partial peptide onto a solid phase, the IRAP or IRAP partial peptide, or GLUT4 or GLUT4 partial peptide, which is labeled with, e.g., biotin, and an avidin-labeled solid phase (e.g., a plate) are preferably employed. After a test compound is added to this complex, the protein of the present invention released is detected and quantified using antibodies to the protein of the present invention or antibodies to Tag protein. In this procedure, the protein of the present invention used may be the protein of the present invention fused to Tag protein. In this case, the protein of the present invention released may be detected and quantified by antibodies to the protein of the present invention, or may be detected and quantified by antibodies to Tag protein. The compound that releases the protein of the present invention is screened as the binding inhibitor.

The screened compound can be verified in terms of its inhibition activity by a publicly known method such as the immunoprecipitation method, using an anti-IRAP antibody, anti-GLUT4 antibody, an antibody to the protein of the present invention or an antibody to Tag; etc. In the immunoprecipitation method, the protein of the present invention, IRAP or GLUT4, which is released by the binding of the protein of the present invention to IRAP or GLUT4 being inhibited, is detected by an antibody to the protein of the present invention, an antibody to Tag protein, an antibody to IRAP or an antibody to GLUT4.

(2-2) Screening by the Two-Hybrid Method (2-2-1) Screening by the Yeast Two-Hybrid Method When a DNA encoding the partial peptide corresponding to the cytoplasmic side domain of IRAP described above or the partial peptide corresponding to the domain of GLUT4 in the cytoplasm described above, to which a reporter gene-bound domain has been fused, and a DNA encoding the protein of the present invention, to which a reporter gene transcription active domain, are expressed in yeast (e.g., *Saccharomyces cerevisiae*, preferably *S. cerevisiae* Y190 strain), the phenotypes of β-galactosidase gene and histidine synthetic gene HIS3, which are reporter genes, are expressed. The yeast strain is cultured for a given period of time in the presence of a test compound, and the compounds that reduce the β-galactosidase activity in the yeast strain or can convert the yeast strain into a histidine auxotroph are screened. The yeast strain can be cultured in a manner similar to incubation of the transformant described above, a host to which is yeast. The β-galactosidase activity can be measured according to a publicly known method using as a substrate X-Gal (5-bromo-4-chloro-3-indolyl-β-D-galactopyranoside), ONPG (o-nitrophenyl β-D-galactopyranoside) or CPRG (chlorophenyl red-β-D-galactopyranoside). Expression of the HIS3 phenotype can be measured by culturing the yeast in the minimum medium free of histidine. Among the compounds screened, such compounds that have cytotoxicity and inhibit the activity of the reporter gene product itself by the interaction, etc. with the reporter gene product can be excluded as pseudo-positive compounds.

(2-2-2) Screening by the Animal Cell Two-Hybrid Method

In an animal cell (e.g., a Chinese hamster ovary (CHO) cell), a reporter gene, e.g., chloramphenicol acetyltransferase (CAT) gene or fire fly luciferase gene is introduced. The transcription regulatory region of the reporter gene is designed to induce expression of the reporter gene in an animal cell, by introducing the GAL4-GAL1 transcription regulatory system of the yeast two hybrid system into the animal cell, using as the transcription regulatory region of the reporter gene, e.g., a promoter functioning in an animal cell (e.g., a minimal promoter (TATA box, etc.) derived from adenovirus E1b, etc.) and linked to, e.g., GAL1 transcription active sequence (UAS) at the downstream. When the DNA encoding the partial peptide corresponding to the cytoplasmic side domain of IRAP described above or the partial peptide corresponding to the domain of GLUT4 in the cytoplasm described above, to which the GAL4-DNA-bound domain has been fused, and the DNA encoding the protein of the present invention fused to a DNA encoding, e.g., herpes simplex-derived VP16 protein, are expressed in this transcription regulatory region, the animal cell strain capable of expressing the reporter gene by the action of the two-hybrid is obtained. This cell strain is cultured for a given period of time in the presence of a test compound, the activity of the reporter gene product is measured, and the compounds that reduce the activity are screened. The animal cell strain can be cultured in a manner similar to incubation of the transformant described above, a host to which is an animal cell. The activity of the reporter gene product such as CAT, luciferase, etc. can be assayed using a commercially available kit in accordance with a publicly known method. Among the compounds thus screened, such compounds that have cytotoxicity and inhibit the activity of the reporter gene product itself through the interaction, etc. with the reporter gene product can be excluded as pseudo-positive compounds.

(3) Screening of Compounds that Promote or Suppress

The transcription regulatory region of the DNA of the present invention is cloned, and a reporter gene (e.g., β-galactosidase, fire fly luciferase, chloramphenicol acetyltransferase (CAT), etc.) is fused to the cloned DNA, which is then transfected to an animal cell (e.g., CHO cell). This cell strain is cultured for a given period of time in the presence of a test compound, and the compounds that increase or decrease the production amount of the reporter gene product are screened. The animal cell strain can be cultured in a manner similar to incubation of the transformant described above, a host to which is an animal cell. The increased or decreased production amount of the reporter gene product can be determined, e.g., by assaying the activity of the reporter gene product in the culture solution. Among the compounds thus screened, such compounds that have cytotoxicity and enhance or reduce the activity of the reporter gene product itself by the interaction, etc. with the reporter gene product can be excluded as pseudo-positive compounds.

Examples of test compounds are a peptide, a protein, anon-peptide compound, a synthetic compound, a fermentation product, a cell extract, a vegetable extract, an animal tissue extract and the like. These compounds may be novel compounds or publicly known compounds.

As the compounds that suppress expression of the protein of the present invention, there are compounds that suppress expression of the protein of the present invention obtained by the screening described above, the antisense DNA described above, the compounds that inhibit the promoter activity to the DNA of the present invention later described, and the like.

As the compounds that promote expression of the protein of the present invention, there are compounds that promote expression of the protein of the present invention obtained by the screening described above, the antisense DNA described above, the compounds that promote the promoter activity to the DNA of the present invention later described, and the like.

The screening kit of the present invention comprises the protein of the present invention, and may further contain the peptide corresponding to IRAP or the cytoplasmic side domain or IRAP, or the peptide corresponding to GLUT4 or the domain of GLUT4 in the cytoplasm. Also, the screening kit of the present invention comprises a cell (preferably a transformant (e.g., a cell such as yeast, an animal cell, etc.) transformed by the DNA encoding the protein of the present invention) capable of producing the protein of the present invention. The transformant may be a transformant transformed by a DNA encoding the protein of the present invention and a DNA encoding the peptide corresponding to IRAP or the cytoplasmic side domain of IRAP, or a transformant transformed by a DNA encoding the protein of the present invention and a DNA encoding the peptide corresponding to GLUT4 or the domain of GLUT4 in the cytoplasm.

Examples of the compounds or salts thereof obtainable using the screening method or screening kit of the present invention are the test compounds described above, e.g., compounds selected from peptides, proteins, non-peptide compounds, synthetic compounds, fermentation products, cell extracts, vegetable extracts, animal tissue extracts, blood plasma and the like, and include the compounds that inhibit the binding of the protein of the present invention to IRAP or GLUT4, the compounds that promote or suppress expression of the protein of the present invention, and the like.

As the salts of these compounds, there may be employed similar salts to those of the protein I of the present invention described above.

The compounds that inhibit the binding of the protein of the present invention to IRAP or GLUT4, or the compounds that suppress expression of the protein of the present invention are useful as pharmaceuticals for the prevention/treatment of diseases, e.g., hyperglycemia, diabetes mellitus, etc.

The compounds that promote the protein of the present invention are useful as pharmaceuticals for the prevention/treatment of diseases, e.g., hypoglycemia, etc.

When the compounds or salts thereof obtainable by the screening method or the screening kit of the present invention are used as the prophylactic/therapeutic agents described above, a conventional means may be applied to making pharmaceutical preparations. For example, the compounds or their salts may be prepared into tablets, capsules, elixirs, microcapsules, sterile solutions, suspensions, etc.

Since the thus obtained preparations are all safe and low toxic, they can be administered to, e.g., warm-blooded animal (e.g., human, mouse, rat, rabbit, sheep, swine, bovine, horse, chicken, cat, dog, monkey, chimpanzee, etc.)

The dose of the compound or salts thereof varies depending on activity, target disease, subject to be administered, route for administration, etc.; for example, when the compound that inhibits the binding of the protein of the present invention to IRAP or GLUT4 or the compound that suppresses expression of the protein of the present invention is orally administered for the treatment of diabetes mellitus, the dose is normally about 0.1 to about 100 mg, preferably about 1.0 to about 50 mg, more preferably about 1.0 to about 20 mg per day for adult (as 60 kg body weight). In parenteral administration for the treatment of diabetes mellitus, the single dose varies depending on subject to be administered, target disease, etc. but it is advantageous to administer, for example, the compound that inhibits the binding of the protein of the present invention to IRAP or GLUT4 or the compound that suppresses expression of the protein of the present invention, intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

When the compound that promotes expression of the protein of the present invention is orally administered for the treatment of hypoglycemia, the dose is normally about 0.1 to about 100 mg, preferably about 1.0 to about 50 mg, more preferably about 1.0 to about 20 mg per day for adult (as 60 kg body weight). When the compound that promotes expression of the protein of the present invention is administered to adult (as 60 kg body weight) generally in the form of injection for the treatment of hypoglycemia, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

(4) Quantification of the Protein of the Present Invention

The antibody to the protein of the present invention (hereinafter sometimes merely referred to as the antibody of the present invention) is capable of specifically recognizing the protein of the present invention and thus, can be used for quantification of the protein of the present invention in a test sample fluid, in particular, for a quantification by sandwich immunoassay.

That is, the present invention provides:

(i) a method for quantification of the protein of the present invention in a test sample fluid, which comprises competitively reacting the antibody of the present invention, a test sample fluid and the labeled protein of the present invention, and measuring the ratio of the labeled protein of the present invention bound to said antibody; and, (ii) a method for quantification of the protein of the present invention in a test sample fluid, which comprises reacting the test sample fluid simultaneously or continuously with the antibody of the present invention immobilized on a carrier and a labeled antibody of the present invention, and then measuring the activity of the labeling agent on the insoluble carrier.

In the method (ii) for quantification described above, it is preferred that one antibody is capable of recognizing the N-terminal region of the protein of the present invention (preferably the protein I or protein II of the present invention), while another antibody is capable of reacting with the C-terminal region of the protein of the present invention (preferably the protein I or protein II of the present invention).

The monoclonal antibody to the protein of the present invention may be used to assay the protein of the present invention. Moreover, the protein of the present invention can be detected by means of a tissue staining as well. For these purposes, the antibody molecule per se may be used or F(ab')$_2$, Fab' or Fab fractions of the antibody molecule may also be used.

There is no particular limitation for the assaying method using the antibody to the protein of the present invention; any method may be used so far as it relates to a method in which the amount of antibody, antigen or antibody-antigen complex can be detected by a chemical or a physical means, depending on or corresponding to the amount of antigen (e.g., the amount of the protein) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are [$^{125}$I], [$^{131}$I], [$^3$H], [$^{14}$C], etc. Preferred examples of the enzyme are those that are stable and have a high specific activity, which include β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the protein of the present invention in the test sample fluid can be quantified. The first and second reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the protein of the present invention by the sandwich method according to the present invention, preferred monoclonal antibodies of the present invention used for the first and the second reactions are antibodies, which binding sites to the protein of the present invention are different from one another. Thus, the antibodies used in the first and the second reactions are those wherein, when the antibody used in the second reaction recognizes the C-terminal region of the protein of the present invention, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method and a nephrometry.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the protein of the present invention may be constructed in addition to conditions or operations conventionally used for each of the methods, taking into account the technical consideration of one skilled in the art. For the details of such conventional technical means, a variety of reviews, reference books, etc. may be referred to the following:

For example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121

(Immunochemical Techniques (Part I: Hybridoma Technology and Monoclonal Antibodies)) (published by Academic Press); etc.)

As described above, the protein of the present invention can be quantified with high sensitivity, using the antibody of the present invention.

Furthermore, by quantifying the level of the protein of the present invention using the antibody of the present invention, (1) when an increased level of the protein of the present invention is detected, it can be diagnosed that diseases such as hyperglycemia, diabetes mellitus, etc. are involved or it is highly likely to suffer from these disease in the future; or (2) when a decreased level of the protein of the present invention is detected, it can be diagnosed that a disease such as hypoglycemia, etc. is involved or it is highly likely to suffer from such a disease in the future.

Also, the antibody of the present invention can be employed for detecting the protein of the present invention which may be present in a test sample fluid such as a body fluid, a tissue, etc. The antibody can also be used for preparation of an antibody column for purification of the protein of the present invention, detection of the protein of the present invention in each fraction upon purification, and analysis of the behavior of the protein of the present invention in the cells under investigation.

(5) Gene Diagnostic Agent

The DNA of the present invention, when using the same, e.g., as a probe, can detect an abnormality (gene abnormality) of the DNA or mRNA encoding the protein of the present invention in warm-blooded animal (e.g., human, rat, mouse, guinea pig, rabbit, chicken, sheep, swine, bovine, horse, cat, dog, monkey, chimpanzee, etc.). Therefore, the DNA of the present invention is useful as a gene diagnostic agent for the damage to the DNA or mRNA, its mutation, or its decreased expression, or increased expression or overexpression of the DNA or mRNA.

The gene diagnosis described above using the DNA of the present invention can be performed by, for example, the publicly known Northern hybridization assay, the PCR-SSCP assay (Genomics, 5, 874–879 (1989); Proceedings of the National Academy of Sciences of the United States of America, 86, 2766–2770 (1989)), or the like.

In case that overexpression is detected by, e.g., the Northern hybridization or in case that DNA mutation is detected by the PCR-SSCP method, it can be diagnosed that diseases such as hyperglycemia, diabetes mellitus, or hypoglycemia, etc. are involved or it is highly likely to suffer from these disease in the future.

(6) Pharmaceuticals Comprising Antisense DNA

An antisense DNA that binds to the DNA of the present invention complementarily to inhibit expression of the DNA can prevent the production of the protein of the present invention in vivo, and can thus be used as prophylactic/therapeutic agents for diseases, e.g., hyperglycemia, diabetes mellitus, etc., as in the aforesaid compounds that suppress expression of the protein of the present invention.

In the case that the antisense DNA described above is used as the prophylactic/therapeutic agents above, these agents apply similarly to the various prophylactic/therapeutic agents comprising the antisense DNA described above.

For example, when the antisense DNA is used, the antisense DNA is administered directly, or the antisense DNA is inserted into an appropriate vector such as retrovirus vector, adenovirus vector, adenovirus-associated virus vector, etc. followed by treating in a conventional manner. The antisense DNA may be administered as it stands, or with a physiologically acceptable carrier to assist its uptake by gene gun or through a catheter such as a catheter with a hydrogel.

The dose of the antisense DNA varies depending upon target disease, subject to be administered, route for administration, etc. but when the antisense DNA is intratracheally administered locally as inhalants, the antisense DNA is administered at a daily dose of about 0.1 to about 100 mg for adult (as 60 kg body weight).

In addition, the antisense DNA may also be employed as an oligonucleotide probe for diagnosis to examine the presence of the DNA of the present invention in tissues or cells and the state of its expression.

(7) Pharmaceuticals Comprising the Antibody of the Present Invention

The antibody of the present invention which possesses the effect to neutralize the activities of the protein of the present invention can be used as drugs (prophylactic/therapeutic agents) for diseases such as hyperglycemia, diabetes mellitus, etc.

The prophylactic/therapeutic agents comprising the antibody of the present invention maybe administered orally or parenterally to warm-blooded animals (e.g., human, rat, rabbit, sheep, swine, bovine, cat, dog, monkey, etc.) as a liquid preparation in its original form, or as a pharmaceutical composition in an appropriate drug form. The dose varies depending on subject to be administered, target disease, conditions, route for administration, etc.; for example, when used for the treatment/prevention of adult patient with diabetes mellitus, it is advantageous to administer the antibody of the present invention intravenously normally in the dose of about 0.01 mg to about 20 mg/kg body weight, preferably about 0.1 to about 10 mg/kg body weight, and more preferably about 0.1 to about 5 mg/kg body weigh, per day once to about 5 times a day, preferably once to about 3 times. In parenteral administration in other route and in oral administration, a dose similar to those given above can be administered. Where conditions are serious, the dose may be increased depending on the conditions.

The antibody of the present invention may be administered in itself or as an appropriate pharmaceutical composition. The pharmaceutical composition used for the administration described above contains the antibody of the present invention and a pharmacologically acceptable carrier, diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections. Such injections are prepared by publiucly known methods, e.g., by dissolving, suspending or emulsifying the aforesaid antibody or its salts in a sterile aqueous or oily liquid medium. For the aqueous medium for injection, for example, physiological saline, isotonic solutions containing glucose and other adjuvant, etc. are used. Appropriate dissolution aids, for example, alcohol (e.g. ethanol), polyalcohol (e.g. propylene glycol, polyethylene glycol), nonionic surfactant [e.g. polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate and benzyl alcohol may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components, unless formulation with the antibody causes any adverse interaction.

(8) DNA Transgenic Animal

The present invention provides a non-human mammal bearing DNA encoding the protein of the present invention, which is exogenous (hereinafter abbreviated as the exogenous DNA of the present invention) or its variant DNA (sometimes simply referred to as the exogenous variant DNA of the present invention).

Thus, the present invention provides:

(1) a non-human mammal bearing the exogenous DNA of the present invention or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goat, rabbits, dogs, cats, guinea pigs, hamsters, mice, rats and the like. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal protein of the present invention and e.g., a DNA that expresses a protein to suppress the function of the normal protein of the present invention, or the like, is employed.

The exogenous DNA of the present invention may be any one of those derived from a mammal of the same species as, or a different species from, the animal of interest. In transfecting the DNA of the present invention to the animal of interest, it is generally advantageous to use the DNA as a DNA construct in which the DNA has been ligated downstream a promoter capable of expressing the DNA in the animal cell. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the protein of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and chicken β actin promoters etc., which protein can highly express in the whole body, are preferred.

It is preferred that the vectors described above have a sequence for terminating the transcription of the desired messenger RNA in the DNA transgenic animal (generally termed a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from various mammals (e.g., human, rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can be obtained using complementary DNA prepared by a publicly known method from RNA of human fibroblast origin as a starting material. Alternatively, the translational region for a normal protein translational region obtained by the cell or tissue described above can be made variant by point mutagenesis.

The translational region can be prepared by a conventional DNA engineering technique in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in such a manner that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal of this species that inherits the exogenous DNA of the present invention also has the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

Transfection of the exogenous DNA of the present invention at the fertilized egg cell stage is preserved to be excessively present in all of the germinal and somatic cells of the target mammal. The fact that the exogenous DNA of the present invention is excessively present in the germinal cells of the prepared animal after the DNA transfection means that all of the offspring in the prepared animal bear excessively the exogenous DNA of the present invention in all of the germinal cells and somatic cells thereof. The offspring of the animal of this species that inherits the exogenous DNA of the present invention has excessively the exogenous DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the protein of the present invention by promoting the functions of endogenous normal DNA. Therefore, the animal can be utilized as a pathologic model animal for such a disease. Specifically, using the normal DNA transgenic animal of the present invention, it is possible to elucidate the mechanism of hyperfunction of the protein of the present invention and to determine how to treat these diseases.

Furthermore, since a mammal, to which the exogenous normal DNA of the present invention has been transfected, exhibits a symptom of increasing the protein of the present invention librated, the animal is also usable for the screening test of prophylactic/therapeutic agents for disease associated with the protein of the present invention.

On the other hand, non-human mammal carrying the exogenous abnormal DNA of the present invention can be passaged under normal breeding conditions as the DNA-bearing animal, by confirming the stable retention of the exogenous DNA via crossing. Furthermore, the objective exogenous DNA can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the mammal of interest. The fact that the abnormal DNA of the present invention is present in the germinal cells of the animal after the DNA transfection means that all of the offspring of the prepared animal have the abnormal DNA of the present invention in all of the germinal and somatic cells. The offspring of the animal of this species that inherits the exogenous DNA of the present invention contains the abnormal DNA of the present invention in all of the germinal and somatic cells. A homozygous animal having the introduced DNA on both of the homologous chromosomes can be acquired and then by mating these male and female animals, all the offspring can be bred and passaged to have the DNA.

Since non-human mammal having the abnormal DNA of the present invention may express the abnormal DNA of the present invention at a high level, the animal may eventually be the function inactivation type in adaptability of the protein by inhibiting the function of the endogenous normal DNA, and can thus be utilized as its disease model animal. For example, using the abnormal DNA-transgenic animal of the present invention, it is possible to elucidate the mechanism of the function inactivation type in adaptability of the protein and to study a method for the treatment of this disease.

As a more specific applicability, the transgenic animal of the present invention that has expressed the abnormal DNA of the present invention to a high level is also expected to serve as an experimental model for elucidation of the mechanism of functional inhibition (dominant negative effect) of normal protein by the abnormal protein of the present invention in the function inactive type in adaptability of the protein of the present invention.

A mammal bearing the abnormal exogenous DNA of the present invention is also expected to serve for screening a candidate drug for the treatment of the function inactive type in adaptability of the protein of the present invention, since the protein of the present invention is increased in such an animal in its liberated form.

Other potential applications of two kinds of the transgenic animals described above include:

(1) use as a cell source for tissue culture;

(2) elucidation of the relation to a protein that is specifically expressed or activated by the protein of the present invention, by direct analysis of the DNA or RNA in tissue of the DNA transgenic animal of the present invention or by analysis of the protein tissue expressed by the DNA;

(3) research in the function of cells derived from tissues that are cultured usually only with difficulty, using cells of tissue bearing the DNA cultured by a standard tissue culture technique;

(4) screening for a drug that enhances the functions of cells using the cells described in (3) above; and, (5) isolation and purification of the variant protein of the present invention and preparation of an antibody thereto.

Furthermore, clinical conditions of a disease associated wit the protein of the present invention, including the function inactive type inadaptability of the protein of the present invention can be determined using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a DNA-transfected cell in its liberated form by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the protein of the present invention, and as studies on association with apoptosis, differentiation or propagation or on the mechanism of signal transduction in these properties to inspect any abnormality therein. Thus the DNA transgenic animal of the present invention can provide an effective research material for the protein of the present invention and for elucidating the function and effect thereof.

To develop a therapeutic drug for the treatment of diseases associated with the protein of the present invention, including the function inactive type inadaptability of the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

(9) Knockout Animal

The present invention provides a non-human mammal embryonic stem cell bearing the DNA of the present invention inactivated and a non-human mammal deficient in expressing the DNA of the present invention.

That is, the present invention provides:

(1) a non-human embryonic stem cell in which the DNA of the present invention has been inactivated;

(2) an embryonic stem cell according to (1), wherein the DNA has been inactivated by introducing a reporter gene (e.g., β-galactosidase gene derived from *Escherichia coli*);

(3) an embryonic stem cell according to (1), which is resistant to neomycin;

(4) an embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention has been inactivated;

(7) a non-human mammal according to (5), wherein the DNA has been inactivated by inserting a drug resistant gene (e.g., neomycin resistant gene) or a reporter gene (e.g., β-galactosidase derived from *Escherichia coli*) therein and the reporter gene is capable of being expressed under control of a promoter for the DNA of the present invention;

(8) a non-human mammal according to (6), which is a rodent;

(9) a non-human mammal according to (8), wherein the rodent is mouse; and,

(10) a method for screening a compound or its salt that promotes or inhibits expression the promoter activity for the DNA of the present invention, which comprises administering a test compound to the mammal of (7) and detecting expression of the drug resistant gene or the reporter gene.

The non-human mammal embryonic stem cell in which the DNA of the present invention has been inactivated refers to a non-human mammal embryonic stem cell that suppresses the ability of the non-human mammal to express the DNA by artificially mutating the DNA of the present invention, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention has been inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons to, thus inhibit the synthesis of complete messenger RNA and eventually destroy the gene (hereinafter simply referred to as targeting vector). The thus-obtained ES cells to Southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the BDF1 mouse (F1 hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF1 mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes be identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be sub cultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1–10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that when cells are observed at passage and cells found to be morphologically abnormal in culture, these cells are abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expressing the DNA of the present invention, which are obtainable from the differentiated ES cells of the present invention are useful for studying the functions of the protein of the present invention cytologically or molecular biologically.

The non-human mammal deficient in expressing the DNA of the present invention can be identified from a normal animal by measuring the mRNA amount in the subject animal by a publicly known method, and indirectly comparing the degrees of expression.

As the non-human mammal, the same examples supra apply.

With respect to the non-human mammal deficient in expressing the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The cells in which the DNA of the present invention has been knockout can be identified by the Southern hybridization analysis using as a probe a DNA fragment on or near the DNA of the present invention, or by the PCR analysis using as primers a DNA sequence on the targeting vector and another DNA sequence, which is not included in the targeting vector. When non-human mammalian embryonic stem cells are used, a cell line wherein the DNA of the present invention has been inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the peptide of the present invention. The individuals deficient in homozygous expression of the protein of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention has been knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention has been inactivated is very useful for preparing a non-human mammal deficient in expressing the DNA of the present invention.

Since the non-human mammal, in which the DNA of the present invention has been inactivated, lacks various biological activities derived from the protein of the present invention, such an animal can be a disease model suspected of inactivated biological activities of the protein of the present invention and thus, offers an effective study to investigate causes for and therapy for these diseases.

(10) Method for Screening of Compounds having Therapeutic/Prophylactic Effects for Diseases Caused by Deficiency, Damages, etc. of the DNA of the Present Invention The non-human mammal deficient in expressing the DNA of the present invention can be employed for screening of compounds having prophylactic/therapeutic effects for diseases (e.g., hypoglycemia, etc.) caused by deficiency, damages, etc. of the DNA of the present invention.

That is, the present invention provides a method for screening of a compound having therapeutic/prophylactic effects for diseases caused by deficiency, damages, etc. of the DNA of the present invention, which comprises administering a test compound to the non-human mammal deficient in expressing the DNA of the present invention and observing and measuring a change occurred in the animal.

As the non-human mammal deficient in expressing the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma and the like and these compounds may be novel compounds or publicly known compounds.

Specifically, the non-human mammal deficient in expressing the DNA of the present invention is treated with a test compound, comparison is made with an intact animal for control and a change in each organ, tissue, disease conditions, etc. of the animal is used as an index to assess the prophylactic/therapeutic effects of the test compound.

For treating an animal to be test with a test compound, for example, oral administration, intravenous injection, etc. are applied and the treatment is appropriately selected depending upon conditions of the test animal, properties of the test compound, etc. Further, the dose of a test compound for administration can be appropriately chosen depending on administration route, nature of the test compound and the like.

The compound obtained using the above screening method is a compound selected from the test compounds described above and exhibits prophylactic/therapeutic effects on the diseases (e.g., hypoglycemia, etc.) caused by a decreased expression level of the protein of the present invention, etc. Therefore, the compound can be employed as a safe and low toxic drug for the treatment/prevention of these diseases. Furthermore, compounds derived from such a compound obtained by the screening supra can be likewise employed.

The compound obtained by the screening method above may for its salts. As such salts, there may be employed salts with physiologically acceptable acids (e.g., inorganic acids or organic acids) or bases (e.g., alkali metal salts), with particular preference of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical composition comprising the compound obtained by the above screening method or salts thereof may be manufactured in a manner similar to the method for preparing the composition comprising the protein of the present invention described hereinabove.

Since the pharmaceutical preparation thus obtained is safe and low toxic, it can be administered to human or other warm-blooded animal (e.g., rat, mouse, guinea pig, rabbit, sheep, swine, bovine, horse, cat, dog, monkey, etc.).

The dose of the compound or its salt to be administered varies depending upon particular disease, subject to be administered, route for administration, etc., but when the compound is orally administered for the treatment of, e.g., hypoglycemia, the compound is administered to an adult (as 60 kg body weight) in a dose of about 0.1 to about 100 mg, preferably about 1.0 mg to about 50 mg and more preferably about 1.0 to about 20 mg, per day. The single dose for parenteral administration may vary depending on subject to be administered, target disease, etc., but when the compound is administered generally to an adult (as 60 kg body weight) in the form of an injectable preparation for the treatment of, e.g., hypoglycemia, it is advantageous to administer the composition intravenously in a dose of about 0.01 to about 30 mg, preferably about 0.1 to about 20 mg, more preferably about 0.1 to about 10 mg, per day. As to other animals, the composition can be administered in the above dose with converting it into that for the body weight of 60 kg.

(11) Method for Screening Compounds that Promote or Inhibit the Activity of a Promoter to the DNA of the Present Invention The present invention provides a method for screening compounds or salts thereof that promote or inhibit the activity of a promoter to the DNA of the present invention, which comprises administering a test compound to a non-human mammal deficient in expressing the DNA of the present invention and detecting expression of the reporter gene.

In the screening method supra, the non-human mammal deficient in expressing the DNA of the present invention is selected from the aforesaid non-human mammal deficient in expressing the DNA of the present invention, as an animal in which the DNA of the present invention has been inactivated by introducing a reporter gene and the reporter gene is expressed under control of a promoter to the DNA of the present invention.

The same examples of the test compound apply to those described above.

As the reporter gene, the same examples as described above are also given, and preferred are β-galactosidase (lacZ), soluble alkaline phosphatase gene, luciferase gene and the like.

Since a reporter gene is present under control of a promoter to the DNA of the present invention in the non-human mammal deficient in expressing the DNA of the present invention wherein the DNA of the present invention is substituted with the reporter gene, the activity of the promoter can be detected by tracing expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method supra are the compounds that are selected from the test compounds described above and the compounds that promote or inhibit the promoter activity to the DNA of the present invention.

The compounds obtained by the screening method above may form salts, and as such salts there may be used salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compounds or salts thereof that promote the promoter activity to the DNA of the present invention can promote expression of the protein of the present invention to enhance the activity of the protein. Therefore, they are useful as a safe and low toxic drug for the prevention/treatment of diseases such as hypoglycemia, etc.

On the other hand, the compounds or salts thereof that inhibit the promoter activity to the DNA of the present invention can inhibit expression of the protein of the present invention to inhibit the activity of the protein. Therefore, they are useful as a safe and low toxic drug for the prevention/treatment of diseases such as hyperglycemia, diabetes mellitus, etc.

In addition, compounds induced from the compounds obtained by the screening described above can be used similarly.

A pharmaceutical composition comprising the compounds or salts thereof obtained by the screening method supra may be manufactured as in the composition comprising the protein of the present invention described hereinabove.

Since the pharmaceutical composition thus obtained is safe and low toxic, it can be administered to warm-blooded animal (e.g., human, rat, mouse, guinea pig, rabbit, sheep, swine, bovine, horse, cat, dog, monkey, etc.).

The dose of the compound or its salts may vary depending on target disease, subject to be administered, route for administration, etc.; when the compound that inhibits the promoter activity to the DNA of the present invention is orally administered for the treatment of, e.g., diabetes mellitus, the compound is administered to an adult (as 60 kg body weight) in a dose of about 0.1 to about 100 mg, preferably about 1.0 mg to about 50 mg and more preferably about 1.0 to about 20 mg, per day. For parenteral administration, the single dose may vary depending on subject to be administered, target disease, etc., but when the compound that inhibits the promoter activity to the DNA of the present invention is administered generally to an adult (as 60 kg body weight) in the form of an injectable preparation for the treatment of, e.g., diabetes mellitus, it is advantageous to administer the composition intravenously in a dose of about 0.01 to about 30 mg, preferably about 0.1 to about 20 mg, more preferably about 0.1 to about 10 mg, per day. As to other animals, the composition can be administered in the above dose with converting it into that for the body weight of 60 kg.

On the other hand, when the compound that inhibits the promoter activity to the DNA of the present invention is orally administered for the treatment of, e.g., hypoglycemia, the dose is normally about 0.1 to about 100 mg, preferably about 1.0 to about 50 mg, more preferably about 1.0 to about 20 mg per day for adult (as 60 kg body weight). In parenteral administration, the single dose may vary depending on subject to be administered, target disease, etc. When the compound that inhibits the promoter activity to the DNA of the present invention is administered to an adult (as 60 kg body weight) generally in the form of injection for the treatment of hypoglycemia, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

As stated above, the non-human mammal deficient in expressing the DNA of the present invention is extremely useful for screening the compounds or salts that promotes or inhibit the promoter activity to the DNA of the present invention and can greatly contribute to the elucidation of causes for various diseases suspected of deficiency in expressing the DNA of the present invention and for the development of prophylactic/therapeutic agent for these diseases.

Furthermore, a so-called transgenic animal (gene transferred animal) can be prepared by using a DNA containing a promoter region in the protein of the present invention, ligating genes encoding various proteins at the downstream and injecting the same into oocyte of an animal. It is then possible to synthesize the protein therein specifically and study its activity in vivo. When an appropriate reporter gene is ligated to the promoter region above and a cell line to express the gene is established, the resulting system can be utilized as a search system for a low molecular compound having the action of specifically promoting or suppressing the in vivo productivity of the protein itself of the present invention. By analyzing the promoter region, it is also possible to find a new cis-element and transcription factors linked thereto.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

Substituents, protecting groups and reagents used in this specification are presented as the codes described below.

| | |
|---|---|
| Me | methyl group |
| Et | ethyl group |
| Bu | butyl group |
| Ph | phenyl group |
| TC | thiazolidine-4 (R)-carboxamide group |
| Tos | p-toluenesulfonyl |
| CHO | formyl |
| Bzl | benzyl |
| Cl$_2$-Bzl | 2,6-dichlorobenzyl |
| Bom | benzyloxymethyl |
| Z | benzyloxycarbonyl |
| Cl-Z | 2-chlorobenzyl oxycarbonyl |
| Br-Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

The sequence identification numbers in the sequence listing of the specification indicate the following sequences, respectively.

[SEQ ID NO:1]

This shows the amino acid sequence of human MD36.

[SEQ ID NO:2]

This shows the amino acid sequence of human FHOS.

[SEQ ID NO:3]

This shows the base sequence of human MD36 gene (cDNA).

[SEQ ID NO:4]

This shows the base sequence of human FHOS (cDNA).

[SEQ ID NO:5]

This shows the amino acid sequence of truncate type human FHOS.

[SEQ ID NO:6]

This shows the base sequence of truncate type human FHOS (cDNA).

[SEQ ID NO:7]

This shows the base sequence of primer used in EXAMPLE 2.

[SEQ ID NO:8]

This shows the base sequence of primer used in EXAMPLE 2.

[SEQ ID NO:9]

This shows the base sequence of primer used in EXAMPLE 3.

[SEQ ID NO:10]

This shows the base sequence of primer used in EXAMPLE 3.

[SEQ ID NO:11]

This shows the amino acid sequence of N-terminal 109 amino acid residues of IRAP.

[SEQ ID NO:12]

This shows the base sequence of DNA encoding the amino acid sequence of N-terminal 109 amino acid residues of IRAP.

[SEQ ID NO:13]

This shows the amino acid sequence of 468–510 amino acid residues of GLUT4.

[SEQ ID NO:14]

This shows the base sequence of DNA encoding the amino acid sequence of 468–510 amino acid residues of GLUT4.

[SEQ ID NO:15]

This shows the amino acid sequence of mouse MD36 obtained in EXAMPLE 6 described hereinafter.

[SEQ ID NO:16]

This shows the base sequence of mouse MD36 gene (cDNA) obtained in EXAMPLE 6 described hereinafter.

[SEQ ID NO:17]

This shows the amino acid sequence of mouse FHOS obtained in EXAMPLE 6, which will be later described.
[SEQ ID NO:18]
This shows the base sequence of mouse FHOS gene (cDNA) obtained in EXAMPLE 6, which will be later described.
[SEQ ID NO:19]
This shows the base sequence of primer M-1 used in EXAMPLE 6, which will be later described.
[SEQ ID NO:20]
This shows the base sequence of primer M-5 used in EXAMPLE 6, which will be later described.
[SEQ ID NO:21]
This shows the base sequence of primer MMD-3 used in EXAMPLE 6, which will be later described.
[SEQ ID NO:22]
This shows the base sequence of primer M-3 used in EXAMPLE 6, which will be later described.
[SEQ ID NO:23]
This shows the base sequence containing human MD36 gene (cDNA).
[SEQ ID NO:24]
This shows the base sequence containing human FHOS gene (cDNA).
[SEQ ID NO:25]
This shows the base sequence containing truncate type human FHOS gene (cDNA).
[SEQ ID NO:26]
This shows the base sequence containing mouse MD36 gene (cDNA).
[SEQ ID NO:27]
This shows the base sequence containing mouse FHOS gene (cDNA).
[SEQ ID NO:28]
This shows the amino acid sequence of PFN IIL.
[SEQ ID NO:29]
This shows the base sequence encoding the amino acid sequence represented by SEQ ID NO:28.
[SEQ ID NO:30]
This shows the amino acid sequence of PFN II.
[SEQ ID NO:31]
This shows the base sequence of the primer used in REFERENCE EXAMPLE 1.
[SEQ ID NO:32]
This shows the base sequence of the primer used in REFERENCE EXAMPLE 1.
[SEQ ID NO:33]
This shows the amino acid sequence of MD36 used in EXAMPLE 10, containing from the N terminus to the proline-rich domain.

Transformant *Escherichia coli* DH5α/pTB2077 bearing plasmid pTB2077 obtained in EXAMPLE 2 has been on deposit with the Ministry of International Trade and Industry, Agency of Industrial Science and Technology, National Institute of Bioscience and Human Technology (NIBH) as the Accession Number FERM BP-6969 since Dec. 16, 1999 and with Institute for Fermentation, Osaka (IFO) as the Accession Number IFO 16339 since Nov. 30, 1999.

Transformant *Escherichia coli* DH5α/pTB2078 bearing plasmid pTB2078 obtained in EXAMPLE 2 has been on deposit with the Ministry of International Trade and Industry, Agency of Industrial Science and Technology, National Institute of Bioscience and Human Technology (NIBH) as the Accession Number FERM BP-6970 since Dec. 16, 1999 and with Institute for Fermentation, Osaka (IFO) as the Accession Number IFO 16340 since Nov. 30, 1999.

EXAMPLES

The present invention is described in detail below with reference to EXAMPLES and REFERENCE EXAMPLE, but is not intended to limit thereto. The gene manipulation procedures using *Escherichia coli* were performed according to the methods described in the Molecular Cloning.

Example 1

Cloning of cDNA Encoding the IRAP-Bound Protein by the Yeast Two-Hybrid Method

Cloning of cDNA encoding the protein bound to insulin responsive aminopeptidase (IRAP) was carried out by the yeast two-hybrid method. The yeast two-hybrid method was conducted basically using the MATCHMAKER™ two-hybrid system manufactured by Clontech, Inc.

A DNA fragment (hereinafter sometimes referred to as "IRAP (55–82)") encoding the polypeptide of 55–82 amino acid residues in IRAP (Keller et al., J. Biol. Chem., 270, 23612–23618, 1995; amino acid numbers 55–82 in SEQ ID NO:11) was chemically synthesized, and inserted into plasmid pGBT9 (manufactured by CLONTECH, INC.) capable of expressing GAL4-DNA-bound domain (GAL4-BD) under control of ADH1 promoter to be in a correct translational frame, which was made bait vector pBait-2. As the cDNA library to be screened, human skeletal muscle-derived cDNA library manufactured by Clontech, Inc. was employed. This library is constructed to express the library cDNA in yeast, in the form fused to GAL4 transcription activated domain (GAL4-AD) under control of ADH1 promoter. *Saccharomyces cerevisiae* Y190 was used as host yeast. This yeast strain bears on its chromosome β-galactosidase (LacZ) and histidine synthesis gene (HIS3) as reporter genes under control of the TATA box and UAS (upstream activating sequences) of GAL1.

The transformant yeast having the two plasmids by introducing pBait-2 (TRP1 marker) and human muscle skeleton-derived library plasmid (LEU2 marker) in *S. cerevisiae* Y190, and expressing HIS3, which is one of the reporter genes of the two-hybrid, was selected in SD medium as the minimum medium supplemented with 60 mM 3-aminotriazole but with none of Trp, Leu and His. The selected transformants were transferred onto nylon membrane by the replica method and frozen/thawed by liquid nitrogen to homogenate the yeast cell walls, followed by staining with X-Gal (5-bromo-4-chloro-β-galactoside). Strains that exhibited the β-galactosidase activity were made primary candidates. More than $10^7$ library cDNAs were screened by the procedures described above to acquire 12 clones as the candidate genes. From these yeasts, the cell extract was prepared using Zymolyase (manufactured by Seikagaku Corp.) and leucine auxotrophic *Escherichia coli* HB101 was transformed using the DNA fraction.

The transformed *E. coli* was smeared on leucine-free M9 medium and *E. coli* strains bearing the library plasmid (LEU2 marker) were screened and the plasmid was extracted therefrom. Using the extracted library plasmid and pBait-2 as IRAP bait vector, *S. Cerevisiae* was transformed again and the histidine auxotrophy and the β-galactosidase activity of the transformants obtained were examined to acquire 5 clones showing reproducibility. From these clones, a clone (MD36 strain) showing the most potential β-galactosidase activity was selected. The cDNA fragment obtained by the yeast two-hybrid method was 679 bp having the 2995–3674 base numbers shown in FIGS. 1–5 (SEQ ID NO:3)

Example 2

Cloning of Full-Length cDNA of Human MD36

In order to find the entire structure of this cDNA, cloning of the full-length sequence was conducted by plaque hybridization and polymerase chain reaction (PCR). Human skeletal muscle-derived cDNA library (manufactured by Clontech, Inc.; TripleEx vector) was screened by plaque hybridization. In the probing region, the 0.68 kb fragment (SEQ ID NO:3, base numbers 2995–3674) of human MD36 was used. By screening of this phage library cDNA clone of about 1.8 kb (SEQ ID NO:3, base numbers 2015–3853) was obtained from the 3' end of human MD36 cDNA.

Next, cloning by PCR was attempted. The sequence of the 3' end of human MD36 cDNA almost coincided (blastn; score (bits)=3540, E value=0.0) with the sequence of human spleen-derived FHOS cDNA (Westendorf et al., Gene, 232, 173–182, 1999; Genbank Accession No. AF113615). Based on the sequence of FHOS registered in Genbank database, the following 2 primers for PCR were synthesized.

(1)  5'-TGAGCCGGCCGCAGAGCCATGG-3'   (SEQ ID NO:7)

(2)  5'-TGCTCCGTGCGTTCAAGGAGCTCAC-3'   (SEQ ID NO:8)

Using these primers, PCR was carried out. Human skeletal muscle-derived and human spleen-derived cDNAs (Clontech, #7413-1 and #7412-1) were used as the templates. The reaction was carried out at 98° C. for 20 seconds, at 65° C. for 40 seconds and at 72° C. for 3.5 minutes, for 35 cycles. The fragment of about 3.7 kb obtained from each of the tissue-derived cDNAs by PCR was subjected to TA cloning and then base sequence determination. The portions of base sequence substitution arising from the misreading by Taq polymerase were identified by comparing each one of the PCR products to the base sequences of at least 3 clones, and swapped by exchanging a part of the clone free of variation to the DNA fragment. Phage library-derived cDNA fragment that was unlikely to cause variation was used for about 1.8 kb of the 3' end.

By the base sequence determination, the full-length cDNA derived from human skeletal muscle was found to have the sequence of 78 bp in the reported sequence of FHOS cDNA inserted in all of them obtained (FIGS. 1 through 5, SEQ ID NO:3). The sequence corresponding to the insert is the base numbers 1339–1417 in FIGS. 1 to 5 (SEQ ID NO:3). That is, 26 amino acids have been inserted between 440 Lys and 441 Ala in FHOS described in the literature (FIGS. 16 and 17). On the other hand, the human spleen-derived full-length cDNA almost coincided with the reported FHOS but variation accompanied by substitution of some amino acids was noted (SEQ ID NO:2, SEQ ID NO:4, FIGS. 6 through 10, FIGS. 16–17). From human spleen, a novel splicing variant containing a further 24 bp insert was found, but because of the variant containing a termination codon in the inserted sequence, its translational polypeptide terminated in the form added with 7 amino acids after 440 Lys of FHOS described in the literature. The variant was identified to be truncate type (SEQ ID NO:5, SEQ ID NO:6, FIGS. 11 through 14) containing no C terminus, which was obtained by the yeast two-hybrid method described in EXAMPLE 1.

Distribution of the inserted sequence in each of human tissues was examined by PCR using human tissue-derived cDNAs as templates. MTC panels (Clontech; #K1420-1, #K1421-1) were used as cDNAs in human tissues. Primers used are:

5'-CCTACCATCTCTGTGGCACCCTCAGCT-3'   (SEQ ID NO:9)

5'-TTGGGGCTTGCTGGTATCAGTGGCTCC-3'   (SEQ ID NO:10)

Using these primers, PCR was carried out and the PCR product was subjected to TA cloning and then base sequence determination. This PCR was set forth to detect a band of 310 bp in FHOS.

Using the two primers (SEQ ID NO:9 and SEQ ID NO:10) described above, PCR was carried out on cDNAs derived from human tissues. In all tissues other than skeletal muscle, the FHOS-derived 310 bp band and the 334 bp band containing the 24 bp insert sequence were clearly detected. On the other hand, the human MD36-derived PCR product (388 bp) containing the 78 bp insert sequence was detected mainly in the skeletal muscle and only slightly in the heart.

Figure 15:
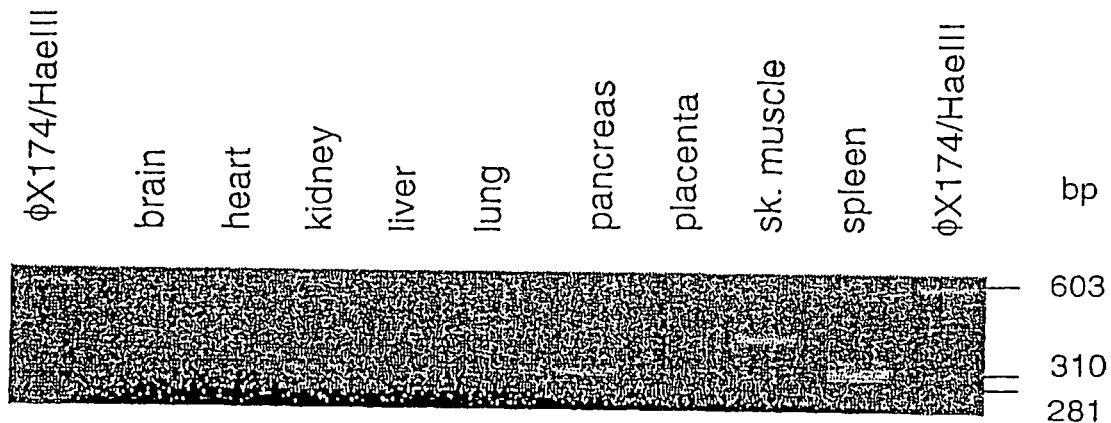

That is, it was verified that the 78 bp insert sequence was specific to skeletal muscle in the organs examined and splicing variants containing no 78 bp insert sequence were barely present in the skeletal muscle (FIG. 15). Based on the foregoing, it is considered that the cDNA fragment of 679 bp obtained in EXAMPLE 1 would be a part of human MD36 cDNA having the 78 bp insert sequence.

Comparison between the amino acid sequences encoding the publicly known FHOS and the 3 cDNAs obtained above is shown in FIGS. 16 and 17. In the total 1164 amino acids, 9 amino acids were different between the FHOS described in the literature and the FHOS obtained in EXAMPLE 2 (249 Thr, 307 Asp, 308 Thr, 633 Asp, 634 Val, 700 Thr, 751 Gly, 849 Asp and 1061 Leu in the FHOS described in the literature are Ser, Glu, Ala, Glu, Leu, Ser, Glu, Glu and Pro, respectively, in the FHOS obtained in EXAMPLE 2).

A plasmid formed by inserting the obtained human FHOS cDNA (SEQ ID NO:4, FIGS. 6 through 10) between SpeI site and XhoI site of pBluescriptII KS+ (manufactured by Stratagene, Inc.) and a plasmid formed similarly by inserting the human MD36 cDNA (SEQ ID NO:3, FIGS. 1 through 5) between SpeI site and XhoI site of pBluescriptII KS+ were named pTB2077 and pTB2078, respectively. In pTB2078, one base substitution due to the PCR remains (1677 G is replaced by A) but this is not accompanied by any variation of amino acids to be translated.

Comparison in protein structure between the human FHOS, human MD36 and truncate type FHOS obtained above is shown in FIG. 18.

Example 3

Verification of the Binding Activity by Quantification Assay for β-Galactosidase Activity In order to verify the binding of human MD36 to IRAP quantitatively, the β-galactosidase activity was assayed using CPRG (chlorophenol red-β-D-galactopyranoside) as substrate.

Yeast bearing both bait and prey sought to detect the interactions therebetween was subjected to liquid culture. After the cells were recovered, the cell walls were disrupted by freezing/thawing with liquid nitrogen. After CRPG was added to a suspension of the disrupted cells, absorbance of these samples at 578 nm was measured in terms of the β-galactosidase activity. In the unit of β-galactosidase, the enzyme activity that one yeast cell is capable of hydrolyzing 1 μmol of CPRG into chlorophenol red and D-galactoside was made 1 unit. IRAP (55–82) was used as the bait sequence and as the prey sequence, the sequence (679 bp corresponding to the base numbers 2995–3674 in SEQ ID NO:3) directly isolated from human MD36 cDNA sequence by the yeast two-hybrid method was used. In addition, vector pGBT9 that expresses bait sequence-unfused GAL4-BD was used as a negative control. Using plasmids having these sequences, *S. Cerevisiae* Y190 was transformed and the β-galactosidase activity of the reconstructed yeast transformants was assayed. The transformant bearing MD36 cDNA exhibited about 70 units of the β-galactosidase activity when IRAP (55–82) was its bait. On the other hand, the binding activity was scarcely noted with the protein bearing GAL4-BD alone but no bait sequence (FIG. 19). In the experiment using the strain bearing no human MD36 cDNA that is the prey sequence, the β-galactosidase activity was less than the detectable limit.

Example 4

Study on the Interaction between Human MD36 and Glucose Transporter

It is known that GLUT4 vesicles are translocated to the cell surface by a polypeptide of the carboxy-terminal (C-terminal) part, which is the cytoplasmic domain of GLUT4 (Lee & Jung, J. Biol. Chem., 272, 21497–21531, 1997). If the anchor protein of GLUT4 vesicles is only one, there is a possibility that the protein bound to IRAP localized in GLUT4 vesicles would bind to GLUT4 as well. This hypothesis was checked by the yeast two-hybrid method.

As the bait sequence, the C-terminal cytoplasmic domain (amino acid numbers 468–510; SEQ ID NO:13 and SEQ ID NO:14) of mouse GLUT4 was used. For control, similar procedures were performed using the C-terminal cytoplasmic domain (amino acid numbers 451–492) of mouse GLUT1, which is the other protein of glucose transporters. These sequences were isolated from the respective cDNAs by PCR using pfu polymerase (manufactured by Stratagene, Inc.) and constructed to be expressed as the fusion proteins in the GAL4-BD sequence of pGBT9 (manufactured by Clontech, Inc.). On the other hand, human MD36 cDNA (base numbers 2995–3674 in SEQ ID NO:3) fused to GAL4-AD was used as the prey sequence. *S. Cerevisiae* Y190 was transformed by these plasmids, and the binding activity of MD36 to each of the glucose transporters was assayed in terms of the β-galactosidase activity. As illustrated in FIG. 20, it was revealed that human MD36 bound to GLUT4 but on the other hand, scarcely bound to GLUT1.

Example 5

Distribution of Human MD36 mRNA Expressed in Human Tissues

The distribution of human MD36 mRNA expressed in human tissues was detected by Northern blotting. That is, using as a probe human MD36 cDNA (base numbers 2995–3674 in SEQ ID NO:3), Northern blotting was carried out for poly(A)$^+$ RNA of human tissues. The product manufactured by Clontech, Inc., on which mRNA of human tissues has been transferred, was used as nylon membrane. The probes and conditions for hybridization are the same as those for screening of lambda phage library, described in EXAMPLE 2. Human MD36 cDNA probes labeled with $^{32}$P were hybridized under high stringent conditions, washed and then detected with an image analyzer BAS2000II (manufactured by Fuji Film Co., Ltd.). It was noted that human MD36 mRNA was strongly expressed in the skeletal muscle.

Example 6

Cloning of Mouse MD36 cDNA

By homology search on the human MD36 cDNA sequence (SEQ ID NO:3, FIGS. 1 through 5) to the published EST sequence, a plurality of mouse ESTs were found to be sequences highly homologous mainly to the 3' end of human MD36 cDNA sequence. Genbank EST; D76497 and Genbank EST; AA109839 were chosen from them and used to design PCR primers. The primers used for cloning of this 3'-end have the following sequences.

```
EST:   D76947-derived sequence (sense)
                                      (SEQ ID NO:19)
M-1:   5'-GAGTTTGCTGTCAGCAAAGATGGCATTGAG-3'

EST:   AA109839-derived sequence (antisense)
                                      (SEQ ID NO:20)
M-5:   5'-TTGCTTAGTCCCAGTGCCTGCACCAGGTCATCTCC-3'
```

M-1 is the partial base sequence corresponding to 2314–2343 from the 5' end of SEQ ID NO:16 (base sequence of mouse MD36 DNA), and M-5 is a complementary base sequence to the partial base sequence corresponding to 3583–3617 from the 5' end of SEQ ID NO:16 (base sequence of mouse MD36 DNA). Using primers M-1 and M-5, PCR was performed using mouse skeletal muscle cDNA (CLONTECH) as a template to obtain the DNA fragment of about 1.3 kb having homology to human MD36.

Since the sequence at the 5' end was still unclear in the experiment described above, further search was made on the Celera's mouse genome sequence database to find any fragment having homology to the 5' end of human MD36. Sequence CMGD: 90000308913152 was detected as the homology sequence. The ATG part, which is the initiation codon in human MD36, coincided also with this Celera sequence, and the termination codon with the frame being adjusted was present further upstream the same. Using the part around this termination codon as primers, PCR was performed on the base sequences of the mouse partial cDNA previously obtained. The primers used for cloning of this 5' end part have the following sequences.

```
Celera:  CMGD; 90000308913152-derived sequence
         (sense)
                                      (SEQ ID NO:21)
MMD-3:   5'-TGAAGTTGCAGCATTTGCAGGGGACAC-3'

EST:     D76947-derived sequence (antisense)
                                      (SEQ ID NO:22)
M-3:     5'-agctgggcttcctcaatcttctgccgctct-3'
```

MMD-3 is the partial base sequence corresponding to 1–27 from the 5' end of SEQ ID NO:16 (base sequence of mouse MD36 DNA), and M-3 is a complementary base sequence to the partial base sequence corresponding to 2373–2402 from the 5' end of SEQ ID NO:16 (base sequence of mouse MD36 DNA). Using primers MMD-3 and M-3, PCR was performed using mouse skeletal muscle cDNA (CLONTECH) as a template to obtain two DNA fragments of about 2.4 kb having homology to human MD36. In the two sequences, the sequence represented by SEQ ID NO:16 (base sequence of mouse MD36 DNA) and the 78 bp base sequence from 1393 "C" to 1470 "A" of this sequence were lacking (mouse FHOS DNA; SEQ ID NO:18). Indicating by the code of amino acids, 445 Leu to 470 Glu from the N terminus of mouse MD36 (SEQ ID NO:15) were lacking in mouse FHOS (mouse FHOS amino acids; SEQ ID NO:17). Since this deficiency site coincided with the splicing variant site in human FHOS and human MD36, the shorter sequence (SEQ ID NO:17) was considered to be the mouse counterpart coincident with human FHOS (SEQ ID NO:2). The two 5'-end fragments obtained by PCR of MMD-3 and M-3 completely coincided with the 3'-end fragments previously obtained by PCR of M-1 and M-5 in the overlapping sequence between the primers M-1 and M-3. It is thus considered that these PCR fragments separately obtained would be derived from common mRNAs, respectively, in both mouse FHOS type and mouse MD36 type.

Furthermore, those from the primer M5 to the termination codon were coincident in a plurality of mouse ESTs. These ESTs are Genbank ESTs AA109839, AA089340, AW540395 and AW412412. Accordingly, the common sequence (5'-AGCTCCTGGTCTAGAGGTGTGA-3') (SEQ ID NO: 34) in the ESTs was considered to be a consensus sequence from the primer M5 to the termination codon. The homology in amino acid sequence between human and mouse was 86.8% between human FHOS (SEQ ID NO: 2) and mouse FHOS (SEQ ID NO: 17), which had no insert sequence, and 86.7% between human MD36 (SEQ ID NO: 1) and mouse MD36 (SEQ ID NO: 18), which had the insert sequence of 78 bp.

Example 7

Distribution of Mouse MD36 in Tissues

Using as a probe the PCR fragment obtained using the primers M1 and M5 described in EXAMPLE 6, Northern blotting was carried out. Mouse MD was strongly expressed in the lung and in the skeletal muscle.

Example 8

Biochemical Binding Test of Human MD36

In order to detect by a different method from EXAMPLES 3 and 4 that IRAP and human MD36 exhibits the interaction on a protein level, the following biochemical binding test was conducted.

The C terminal part (partial peptide encoded by the partial base sequence of 2995–3674 from the 5' end in SEQ ID NO:2) of SEQ ID NO:1 (full-length cDNA of MD36) was used as human MD36. This DNA fragment was inserted into pGEX expression vector (Amersham Pharmacia) to construct expression plasmid pGEX-MD36N4 capable of expressing the human MD36 partial protein in the form fused to GST (glutathione S-transferase) protein (GST-MD36N4 protein) under control of tac promoter. However, the protease recognition site in these junctions was removed by applying PCR. Using pGEX-MD36N4, E. coli BL21 was transformed and the transformants were cultured in LB medium in a conventional manner while inducing expression by IPTG. After culture, the cells collected were disrupted by sonication followed by centrifugation of the cell homogenate. As a result, most of the GST-MD36N4 protein were present in the insoluble fraction. This insoluble fraction was redissolved in phosphate buffered saline (PBS) containing 8M urea and 5 mM DTT. By dialyzing the solution to PBS containing 0.5 M arginine hydrochloride, refolding of the protein was effected. Turning to IRAP, the sequence (SEQ ID NO:11), which was the cytoplasmic domain, was inserted into pET21 (Novagen, Inc.) to construct plasmid pET21-IRAP (1–109) capable of expressing the same linked to His-tag under control of T7 promoter, the plasmid was expressed in E. coli in a conventional manner, and the recombinant protein was purified. Hereinafter this recombinant protein is referred to as IRAP-His.

Protein-protein binding test was carried out by the procedure shown below. GST-MD364N (10 μg/ml) dissolved in sodium carbonate buffer solution (25 mM $Na_2CO_3$, 25 mM $NaHCO_3$, pH 9.6) was charged in a 96-well EIA plate and allowed to stand overnight at 4° C. to bind GST-MD364N to the plate surface. After the plate was rinsed 3 times with Tris buffered solution (20 mM Tris-HCl (pH 8.0), 150 mM NaCl, hereinafter referred to as TBS) supplemented with 0.05% Tween 20 (hereinafter referred to as TBS-T), PBS supplemented with 3% bovine serum albumin (BSA) was added thereto and the plate was allowed to stand for an hour at room temperature for blocking. Furthermore, IRAP-His (1.0 μg/ml in TBS) was added to the human MD36-coated wells, which was allowed to stand for 2 hours at room temperature to effect binding. After the wells were again rinsed 3 times with TBS-T, the IRAP-His protein remained in the wells was quantitatively assayed using anti-Penta-His antibody (Qiagen, Inc.). Detection was made using HRP-anti-mouse IgG goat antibody and the ECL system (NEN Life Science, Inc.). IRAP-His (1.0 μg/ml) or anti-Penta-His antibody (diluted to 2000 fold) and both were added to the GST-MD364N-coated or uncoated wells, and after washing with TBS-T, the amount of His-Tag remained in the wells was quantified. His-Tag was markedly detected only when IRAP-His and anti-Penta-His antibody were both added to the human MD36-coated wells, and the background detected under conditions otherwise was very low (FIG. 21). It was further verified if these bindings were inhibited by the IRAP peptide without His-tag. For the binding inhibition test, the biotinylated amino acid number 55–82 of IRAP (IRAP (55–82); a peptide composed of the partial amino acid sequence of 55–82 from the N terminus of SEQ ID NO:11) was chemically synthesized and used for the test. As shown in FIG. 22, the binding of IRAP-His to GST-MD364N was inhibited by adding IRAP (55–82), dependently on its concentration. The foregoing test revealed the specificity of binding IRAP to human MD36 in this system.

Example 9

Screening of a Compound that Inhibits the Binding

Following the procedure of EXAMPLE 8 (biochemical binding test of human MD36), a compound that inhibits the binding of IRAP to human MD36 was screened. At the stage of this procedure where IRAP-His was added, a library compound (dimethylsulfoxide (DMSO) solution) was added in a final concentration of 1 μM, the binding test was carried out, and the compounds with a reduced amount of His-Tag remained on the plate were selected. As a result, the two specimens shown by [Compound 1] and [Compound 2] below exhibited binding inhibition. The $IC_{50}$ value was calculated from a ratio of the measurement value when added with the compound to the measurement value when added with no compound (added with DMSO only) after subtracting the background as the value when added with no IRAP-His from the respective values.

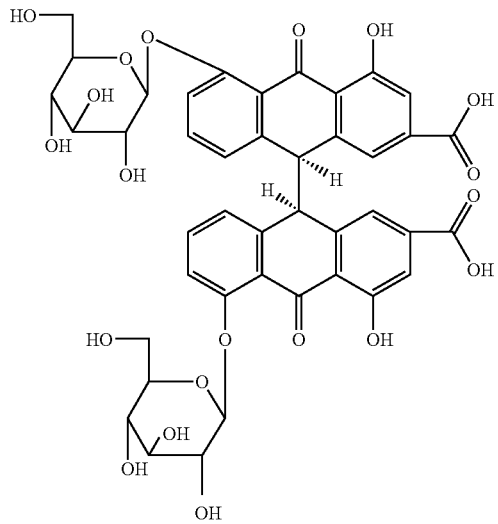

[Compound 1]

IC$_{50}$: 0.21 μM

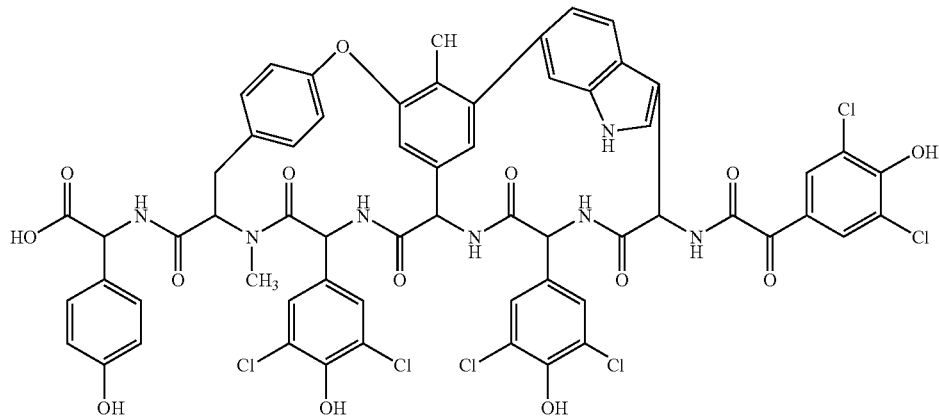

[Compound 2]

IC$_{50}$: 0.24 μM

Reference Example 1

Cloning of Profilin IIL (Protein Having Amino Acids Shown by SEQ ID NO:28, DNA (SEQ ID NO:29) Encoding the Protein)

Profilin IIL was obtained by polymerase chain reaction (PCR) through amplification of profilin II (Genbank accession #L10678; SEQ ID NO:30) between the initiation codon and the termination codon. The primers used for PCR are shown below.

```
                              (27-mer, SEQ ID NO:31)
    (1)   5'-ATGGCCGGTTGGCAGAGCTACGTGGAT-3'

(30-mer, SEQ ID NO:32)
    (2)   5'-TTACACATCAGACCTCCTCAGGTATAAAGC-3'
```

Using as a template human skeletal muscle-derived cDNA and as a enzyme Pfu polymerase (STRATAGENE), the reaction was carried out at 95° C. for 30 seconds, at 65° C. for 45 seconds and at 72° C. for 60 seconds, for 35 cycles. As a result of PCR, the DNA fragment of 745 bp was found, in addition to the DNA fragment of 423 bp or profilin II, and named profilin IIL. The base sequence for cDNA of profilin IIL is shown by SEQ ID NO:29, and the amino acid sequence of profilin II is shown by SEQ ID NO:28.

Tissue distribution of profilin IIL was examined in human MTC-panel by PCR using these primers. Expression of profilin IIL was observed in the brain, skeletal muscle, pancreas, placenta and heart.

Example 10

Study on the Protein-Protein Interaction Between MD36 (Protein Having the Amino Acid Sequence Shown by SEQ ID NO:1) and the Profilin Family The protein-protein interaction between MD36 and the profilin family was detected by the yeast two-hybrid system. Based on pGBT9 (CLONTECH), expression plasmids were constructed to express the coding regions of profiling I (Evangelista et al., Science, 276, 118–122, 1997; Imamura et al., EMBO J., 16, 2745–2755, 1997; Tanaka, Biochem. Biophys. Res. Commun., 267, 479–481, 2000), profilin II (Schluter et al., Biohim. Biophys. Acta, 1359, 97–109, 1997), and profiling IIL in the form fused to yeast GAL4-DNA-binding domain protein under control of yeast ADH1 promoter. These plasmids were named pG-PFNI, pG-PFNII and pG-PFNIII, respectively (yeast selection marker was TRP1). On the other hand, expression plasmids that express the full-length sequence (SEQ ID NO:1) of MD36, which is IRAP-BP protein, or the coding region from this N-terminus to the sequence (SEQ ID NO:33) including the proline-rich domain in the form fused to yeast GLUT4-transcription activated domain protein under control of yeast ADH1 promoter was constructed based on pACT2 (CLONTECH), and named pACT-MD36 and pACT-MD36NT, respectively (yeast selection marker was LEU2). pG-PFNI, pG-PFNII, pG-PFNIII or, pGBT9 for control was co-transfected to yeast *Saccharomyces cerevisiae* Y190 together with pACT-MD36 or pACT-MD36NT, and yeast strains bearing plasmids from the two were selected on SD medium free of tryptophan and leucine. *S. cerevisiae* Y190 is originally a histidine auxotrophic strain but when the introduced proteins on the plasmids show the interactions, reporter gene HIS3 is expressed and the strain becomes capable of growing on a histidine-free plate. The yeast strain acquired was spread on tryptophan, leucine and histidine-free SD medium supplemented with 40 mM 3-amino-1,2,4-triazole. The yeast did not grow with any combination of profilin I/MD36, profilin I/MD36NT, profilin II/MD36 and profilin II/MD36NT, as in the control experiment using pGBT9. Growth of the yeast was noted only with the combinations of profilin IIL/MD36, profilin IIL/MD36NT. These results revealed that MD36 bound specifically to profilin IIL of the profiling family.

INDUSTRIAL APPLICABILITY

The protein I of the present invention is expressed strongly in the skeletal muscle and the protein II of the present invention is expressed in the spleen, etc.

The protein of the present invention binds to IRAP to enhance a blood sugar level, and is thus useful as a prophylactic/therapeutic agent for hypoglycemia.

The protein of the present invention can also be used for the screening method which involves inhibiting the binding of the protein of the present invention to IRAP or GLUT4. The compound that inhibits the binding of the protein of the present invention to IRAP or GLUT4 is useful as a prophylactic/therapeutic agent for diseases such as hyperglycemia, diabetes mellitus, etc.

The invention claimed is:

1. An isolated protein containing the amino acid sequence represented by SEQ ID NO: 1 and having an activity of binding to IRAP or GLUT4, or a salt thereof.

2. An isolated protein containing the amino acid sequence represented by SEQ ID NO: 15, or a salt thereof.

3. A pharmaceutical comprising the protein or its salt according to claim 1 or 2.

4. The pharmaceutical according to claim 3, which is a preventive/therapeutic agent for hypoglycemia.

5. A method of using the protein or its salt according to claim 1 or 2, for manufacturing the pharmaceutical comprising the protein or its salt according to claim 1 or 2.

* * * * *

UNITED STATES PATENT AND TRADEMARK OFFICE
CERTIFICATE OF CORRECTION

| | | |
|---|---|---|
| PATENT NO. | : 7,064,106 B2 | Page 1 of 1 |
| APPLICATION NO. | : 10/168067 | |
| DATED | : June 20, 2006 | |
| INVENTOR(S) | : Hideaki Tojo et al. | |

It is certified that error appears in the above-identified patent and that said Letters Patent is hereby corrected as shown below:

Delete Line [*] Notice: "THIS PATENT IS SUBJECT TO A TERMINAL DISCLAIMER."

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,064,106 B2 Page 1 of 1
APPLICATION NO. : 10/168067
DATED : June 20, 2006
INVENTOR(S) : Hideaki Tojo et al.

It is certified that error appears in the above-identified patent and that said Letters Patent is hereby corrected as shown below:

Title Page, Item (73) Assignee: Delete "TAKEDA CHEMICAL INDUSTRIES, LTD." and insert -- TAKEDA PHARMACEUTICAL COMPANY, LTD. --.

Signed and Sealed this

Nineteenth Day of February, 2008

JON W. DUDAS
*Director of the United States Patent and Trademark Office*